United States Patent [19]

Stembridge et al.

[11] Patent Number: 4,944,336
[45] Date of Patent: * Jul. 31, 1990

[54] AUTOMATIC CONTROL SYSTEM FOR FILLING BEVERAGE CONTAINERS

[75] Inventors: William F. Stembridge, College Park, Ga.; James C. Sturrock, Espanola, N. Mex.; W. Frank Stembridge, East Point, Ga.

[73] Assignee: The Coca-Cola Company, Atlanta, Ga.

[ * ] Notice: The portion of the term of this patent subsequent to Oct. 25, 2005 has been disclaimed.

[21] Appl. No.: 274,091

[22] Filed: Nov. 21, 1988

Related U.S. Application Data

[63] Continuation-in-part of Ser. No. 48,111, May 8, 1987, which is a continuation-in-part of Ser. No. 684,215, Dec. 20, 1984, abandoned, which is a continuation-in-part of Ser. No. 629,397, Jul. 10, 1984, abandoned.

[51] Int. Cl.$^5$ .................... B65B 3/04; H04R 17/00
[52] U.S. Cl. ............................ 141/95; 141/1; 141/198; 73/290 R; 73/294; 73/624; 367/908; 367/150; 367/162; 367/165; 367/176
[58] Field of Search ............... 141/947, 96, 198; 73/624, 290 V, 294, 290 R; 181/124; 367/150, 162, 165, 173, 176, 908

[56] References Cited

U.S. PATENT DOCUMENTS

| | | | |
|---|---|---|---|
| 4,228,530 | 10/1980 | Bergey | 367/908 X |
| 4,264,788 | 4/1981 | Keidel et al. | 367/908 X |
| 4,313,343 | 2/1982 | Kobayashi et al. | 73/290 V |
| 4,437,497 | 3/1984 | Enander | 141/1 |
| 4,437,499 | 3/1984 | Devale | 141/95 |
| 4,458,735 | 7/1984 | Houman | 141/95 |
| 4,559,979 | 12/1985 | Koblasz et al. | 141/9 |
| 4,572,253 | 2/1986 | Farmer et al. | 141/95 |
| 4,780,861 | 10/1988 | Stembridge et al. | 367/150 |
| 4,798,232 | 1/1989 | Stembridge et al. | 141/1 |
| 4,817,689 | 4/1989 | Stembridge et al. | 141/198 |

Primary Examiner—Ernest G. Cusick
Attorney, Agent, or Firm—Thomas R. Boston; W. Dexter Brooks

[57] ABSTRACT

An automatic, ultrasonic system for controlling the filling of different sizes of beverage container which may or may not contain various quantities of ice. The system includes a housing, a front and a rear pair of separate transmitter and receiver crystals mounted in the housing with a lens on the lower surface of each crystal. Each crystal is located within a separate non-ferrous metal tube. Polyurethane foam fills the space within the housing and the tubes.

3 Claims, 95 Drawing Sheets

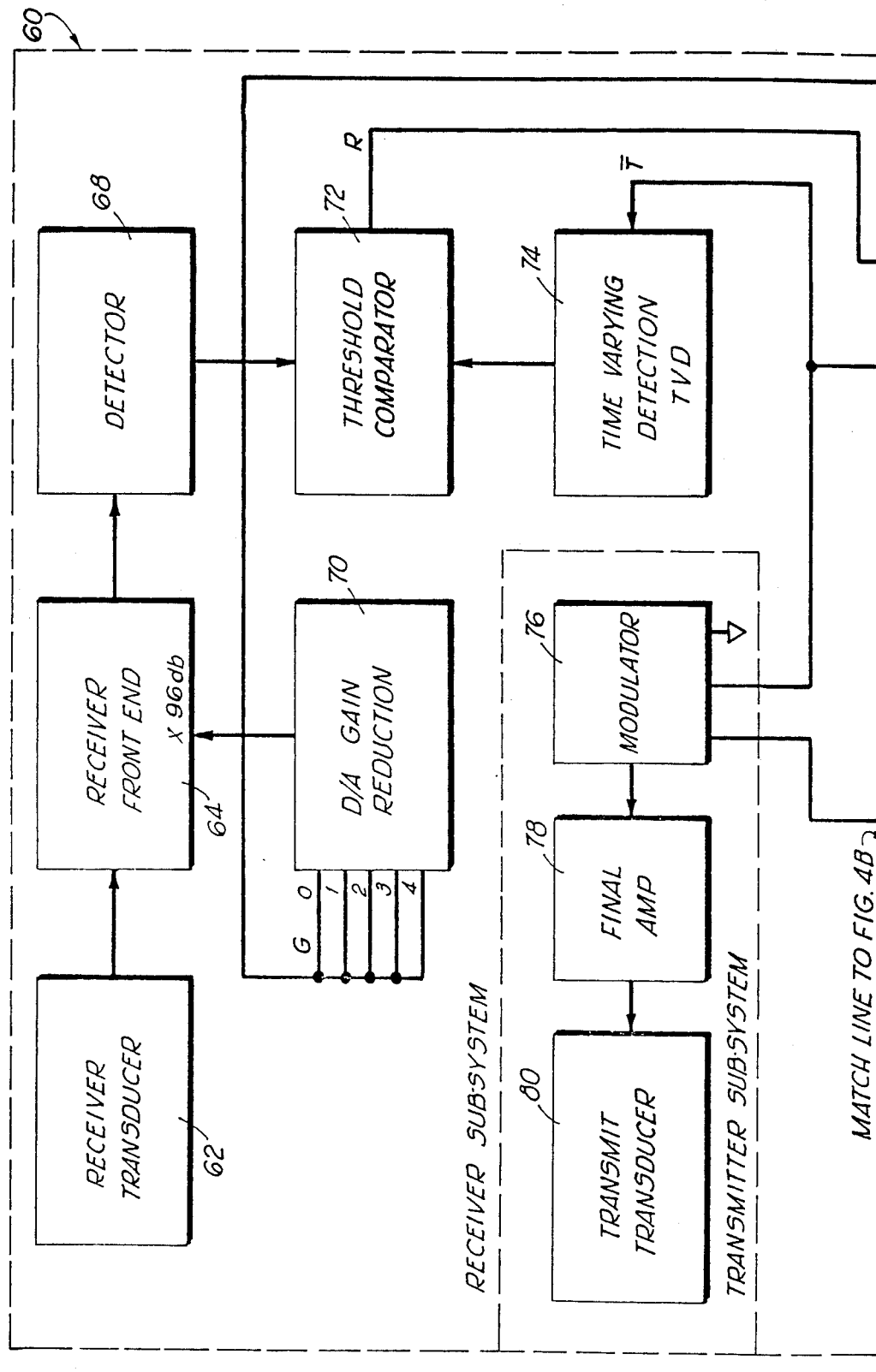

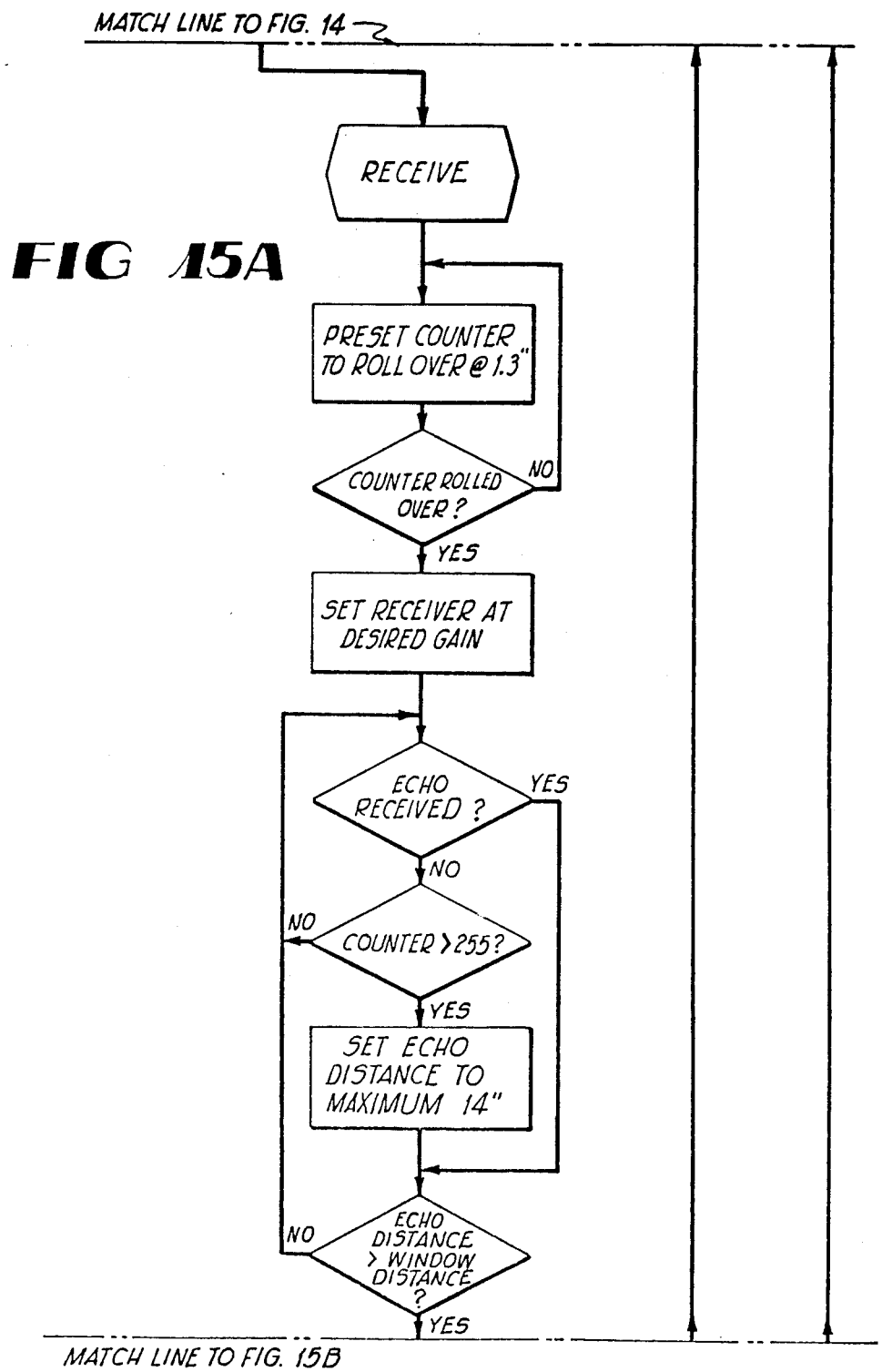

MATCH LINE TO FIG. 15A

FIG 15B

- COUNTER > 225 ? → NO (loop back)
- YES → STORE ECHO IN SAMPLE STORAGE
- LAST SAMPLE? → NO (loop back to top) / YES
- SET SAMPLE POINTER TO BEGINNING OF SAMPLE STORAGE
- SET INDEXING POINTER TO SAMPLE POINTER
- GET VALUE AT SAMPLE POINTER (X1)
- INCREMENT INDEXING POINTER
- LAST SAMPLE? → YES → INCREMENT SAMPLE POINTER → LAST SAMPLE? → YES (to top) / NO (loop back)
- NO → GET VALUE AT INDEXING POINTER (X2)

MATCH LINE TO FIG 15C

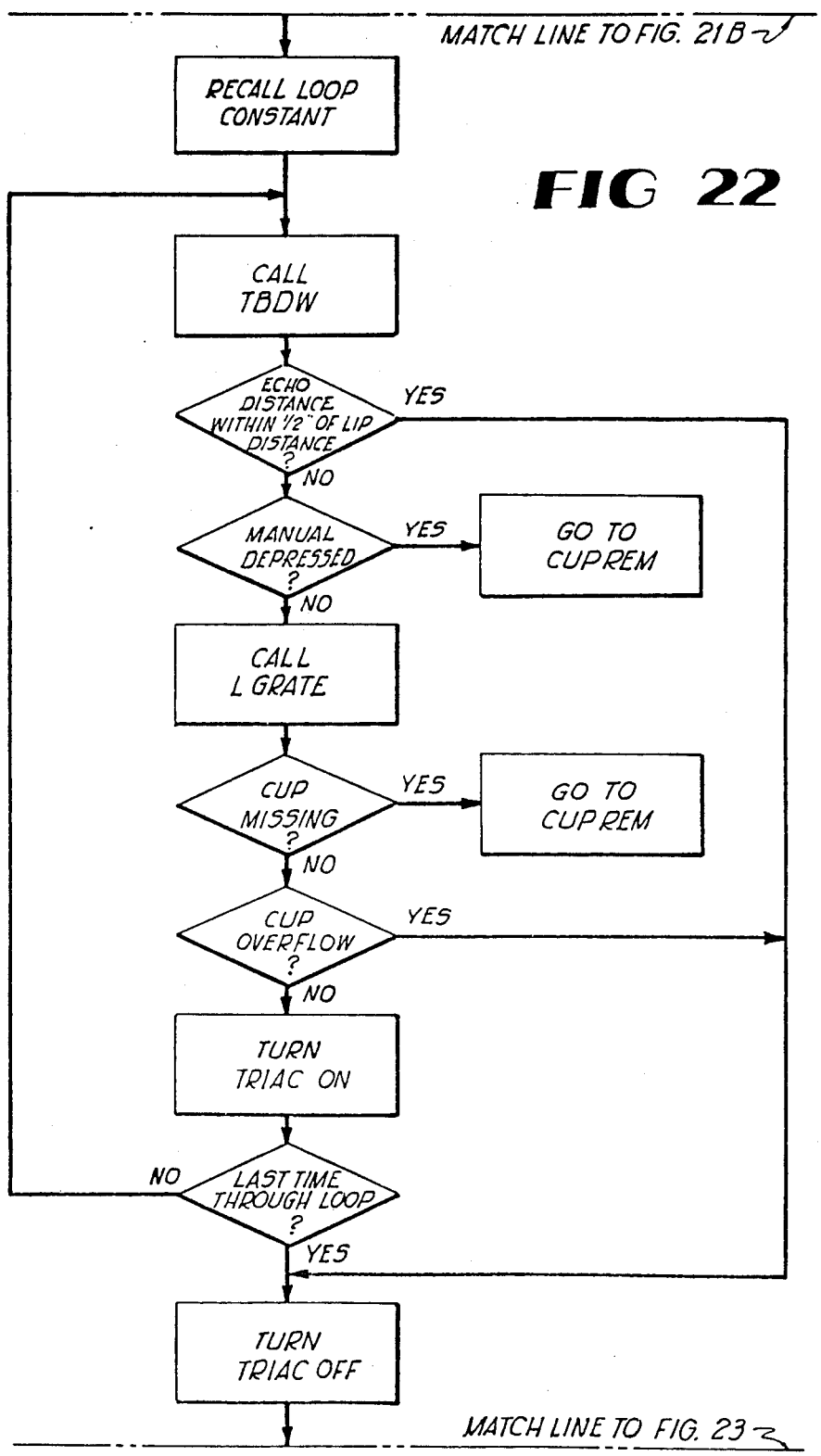

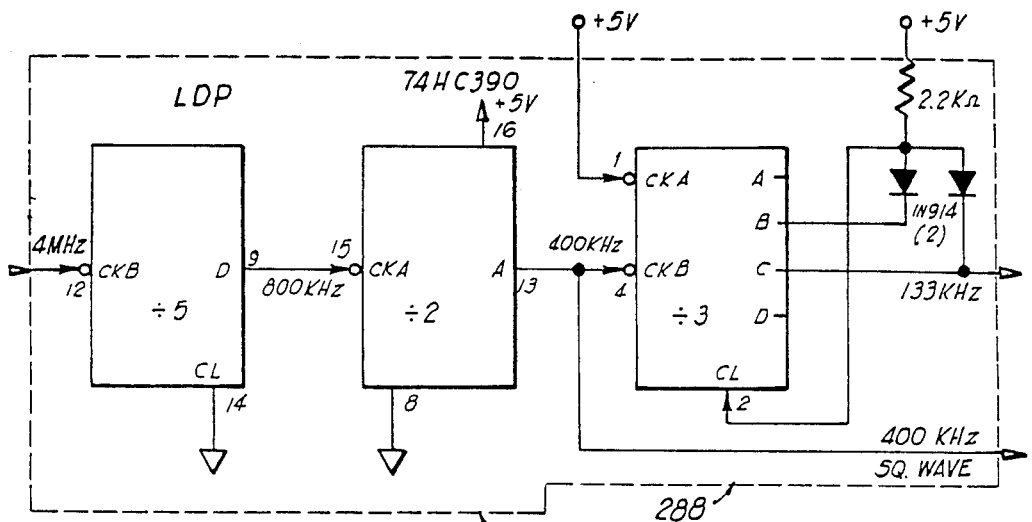
FIG 37
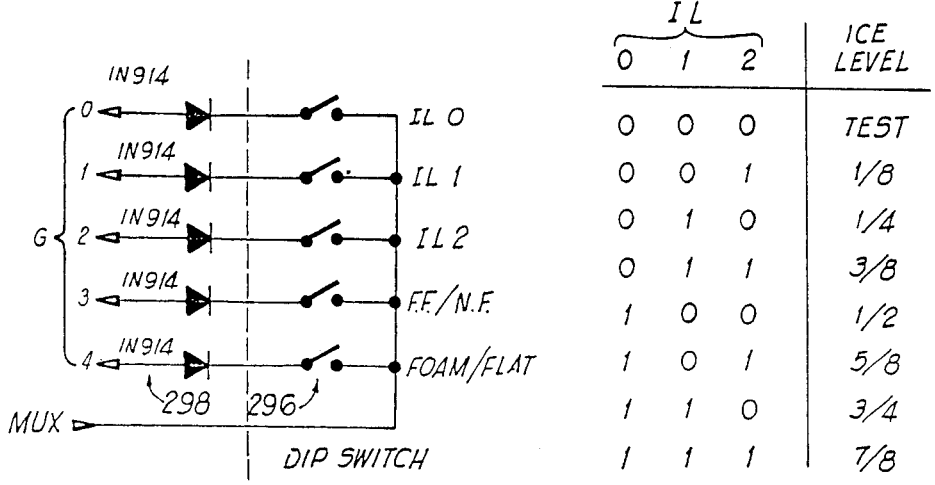
FIG 38A  FIG 38B
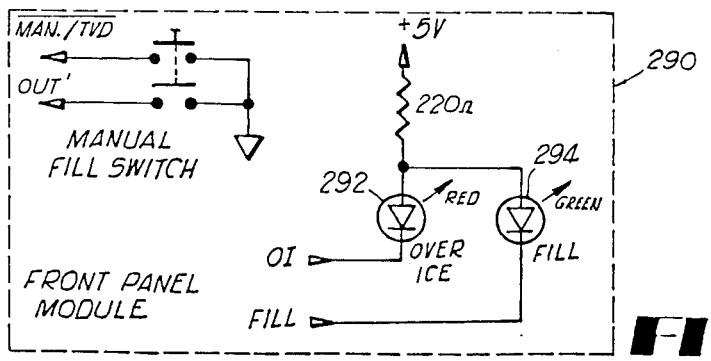
FIG 39

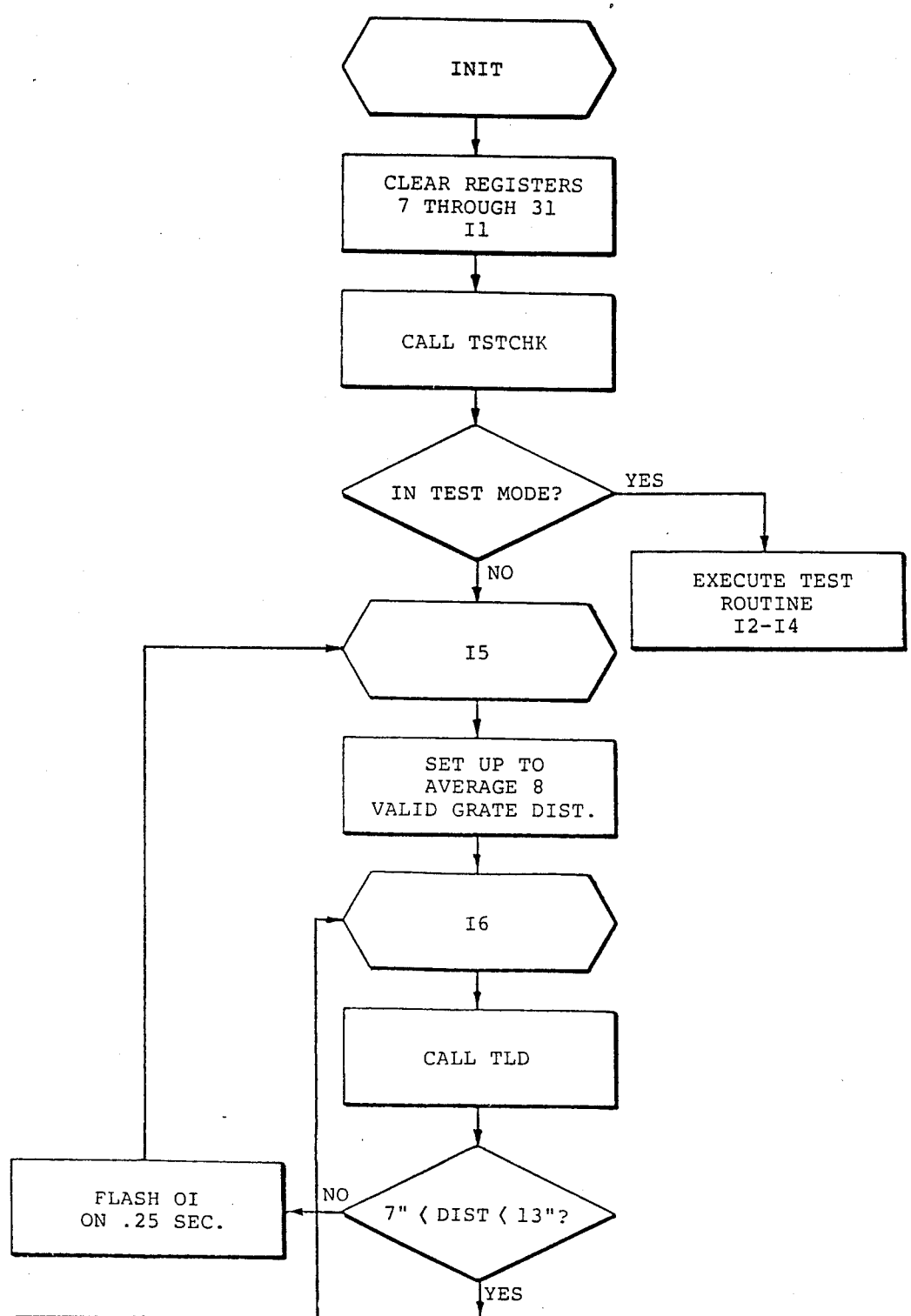
FIG 45A    MATCH LINE TO FIG. 45B

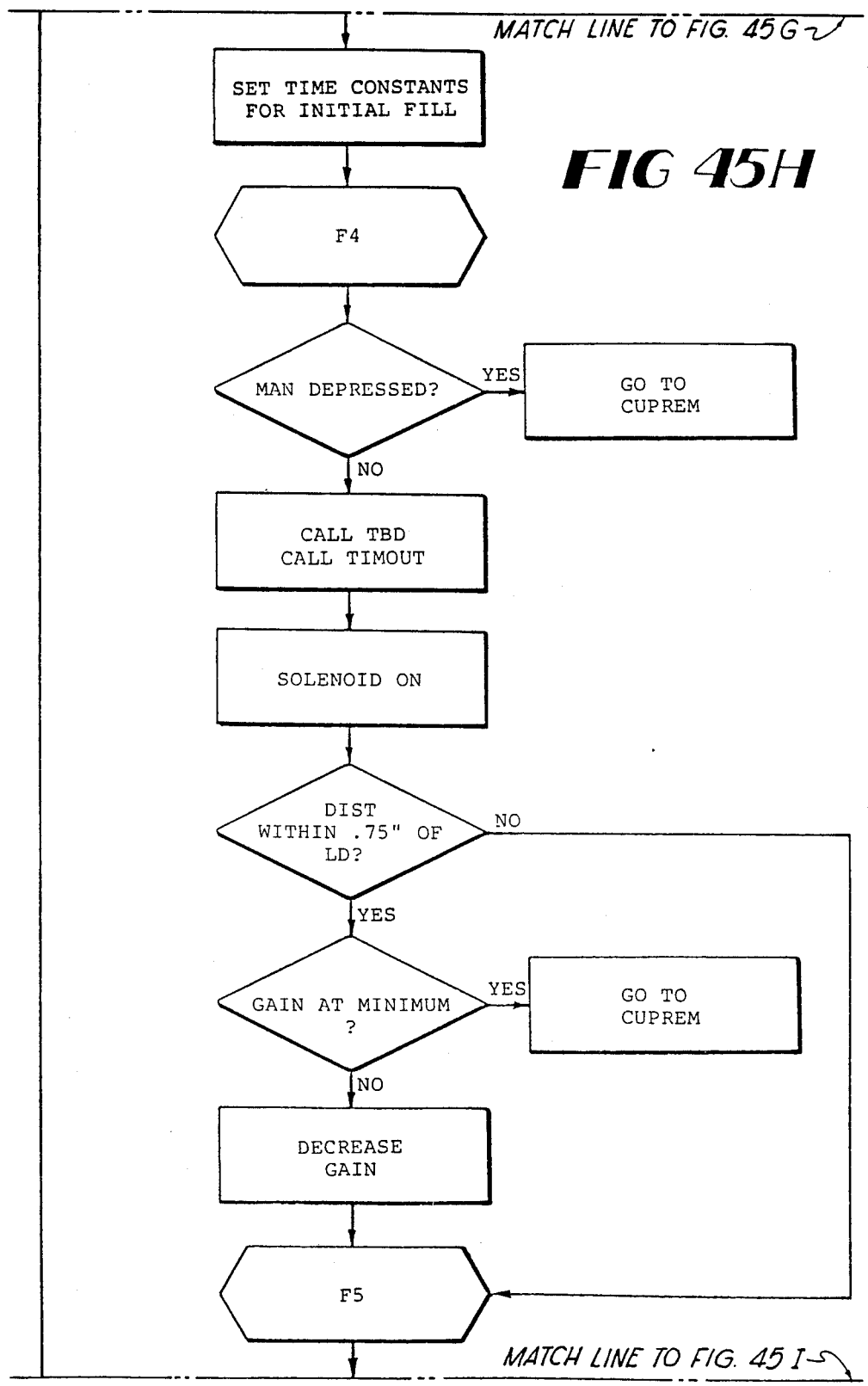

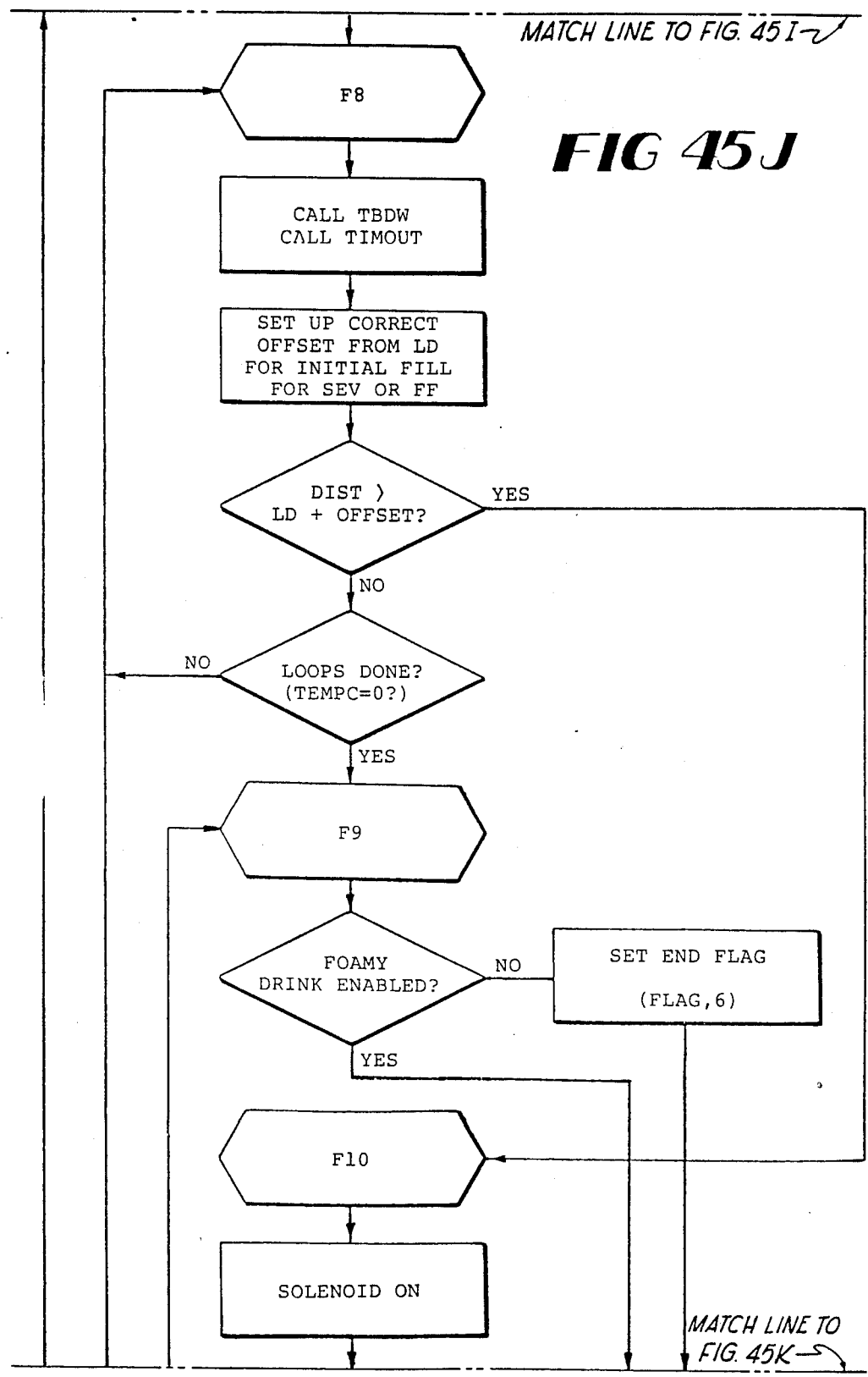

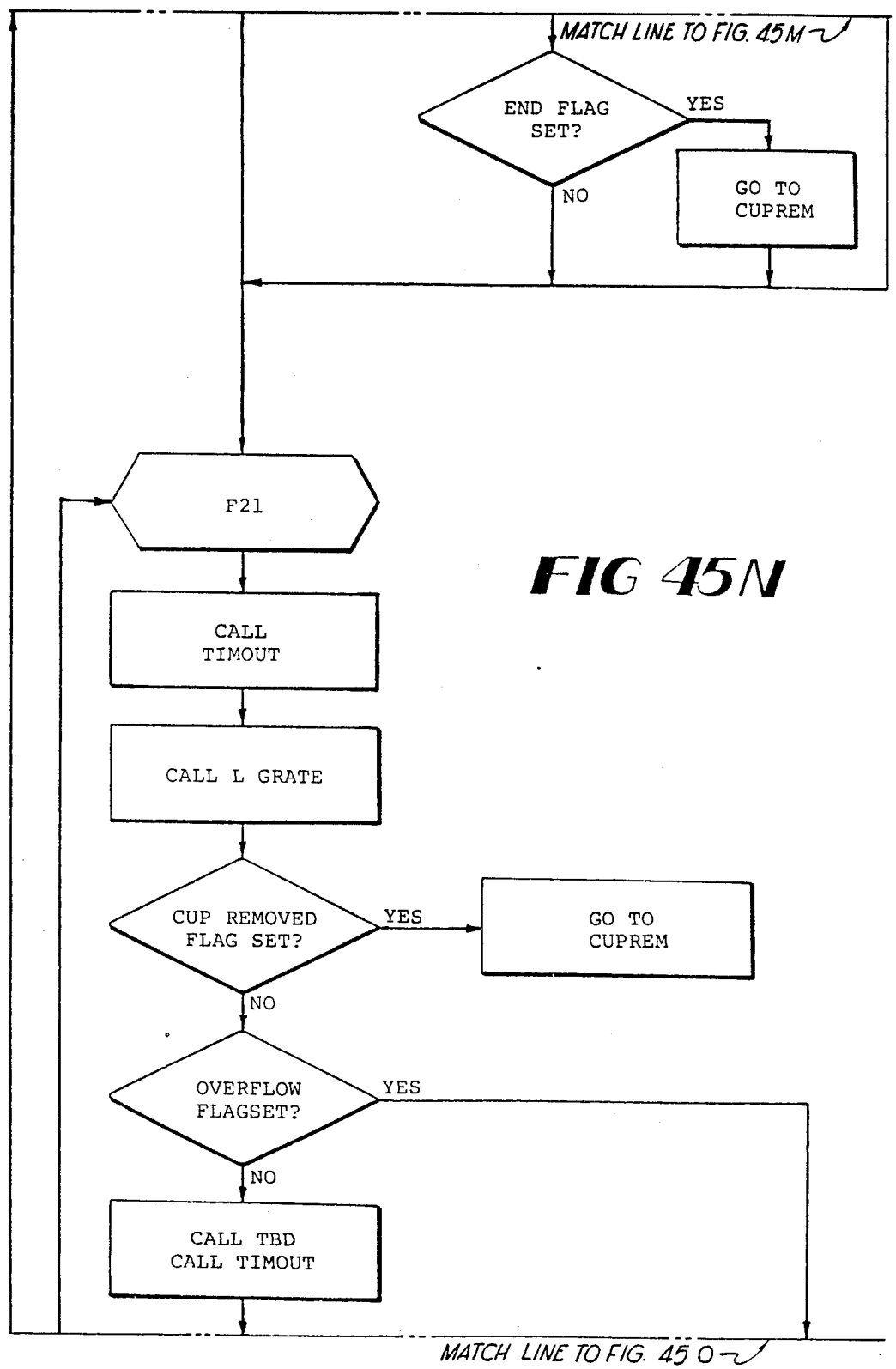

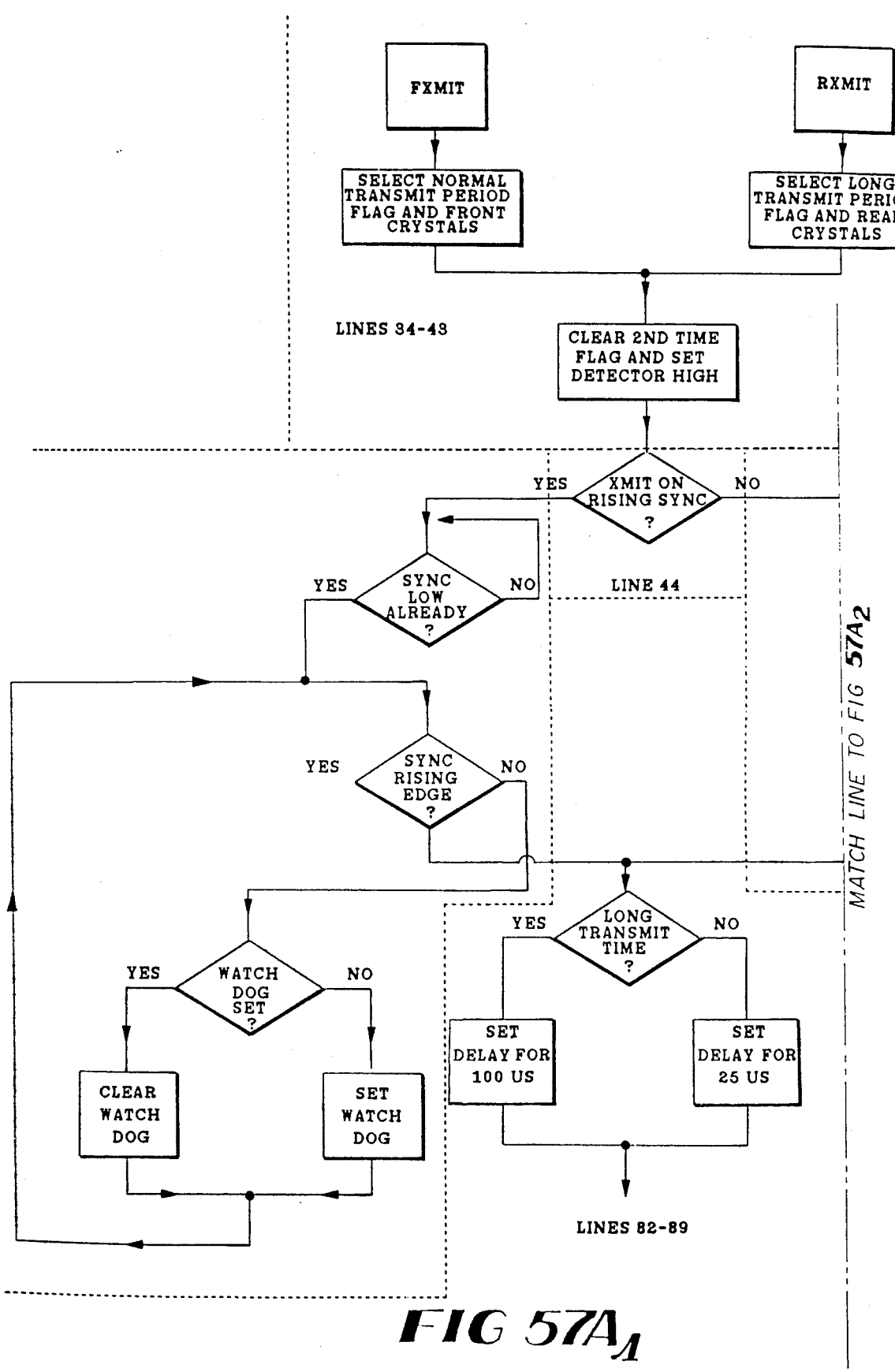
FIG 57A₁

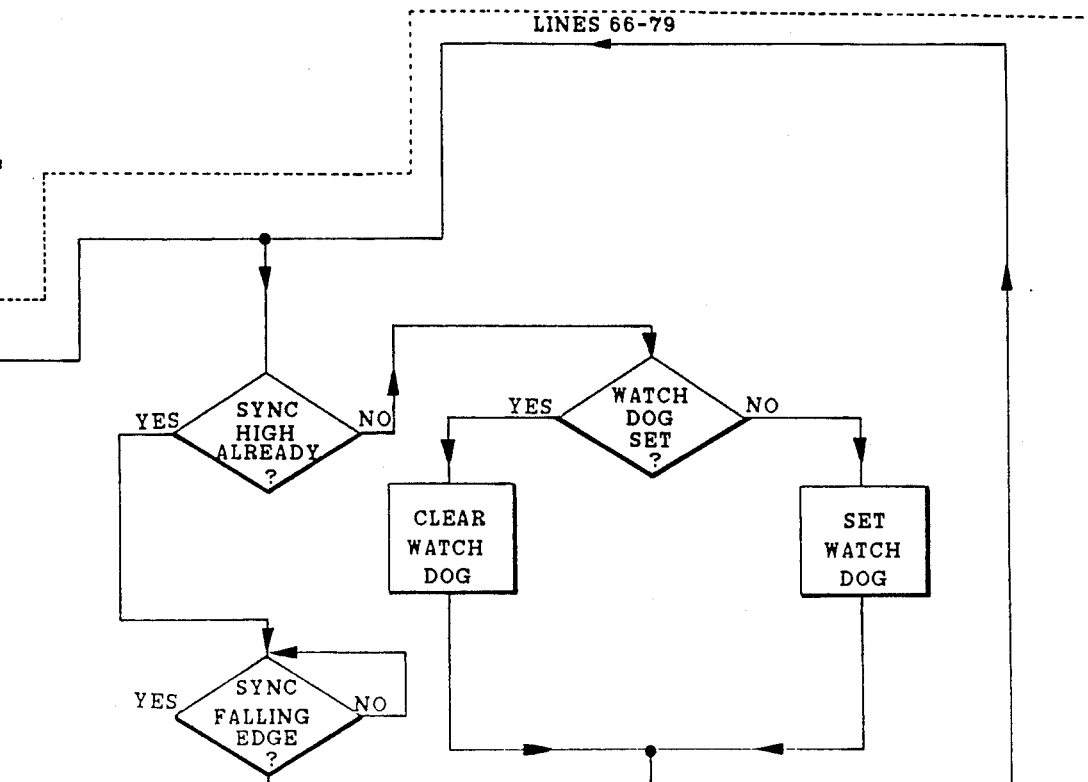
FIG 57A₂

LINES 83-88

LINES 94-99

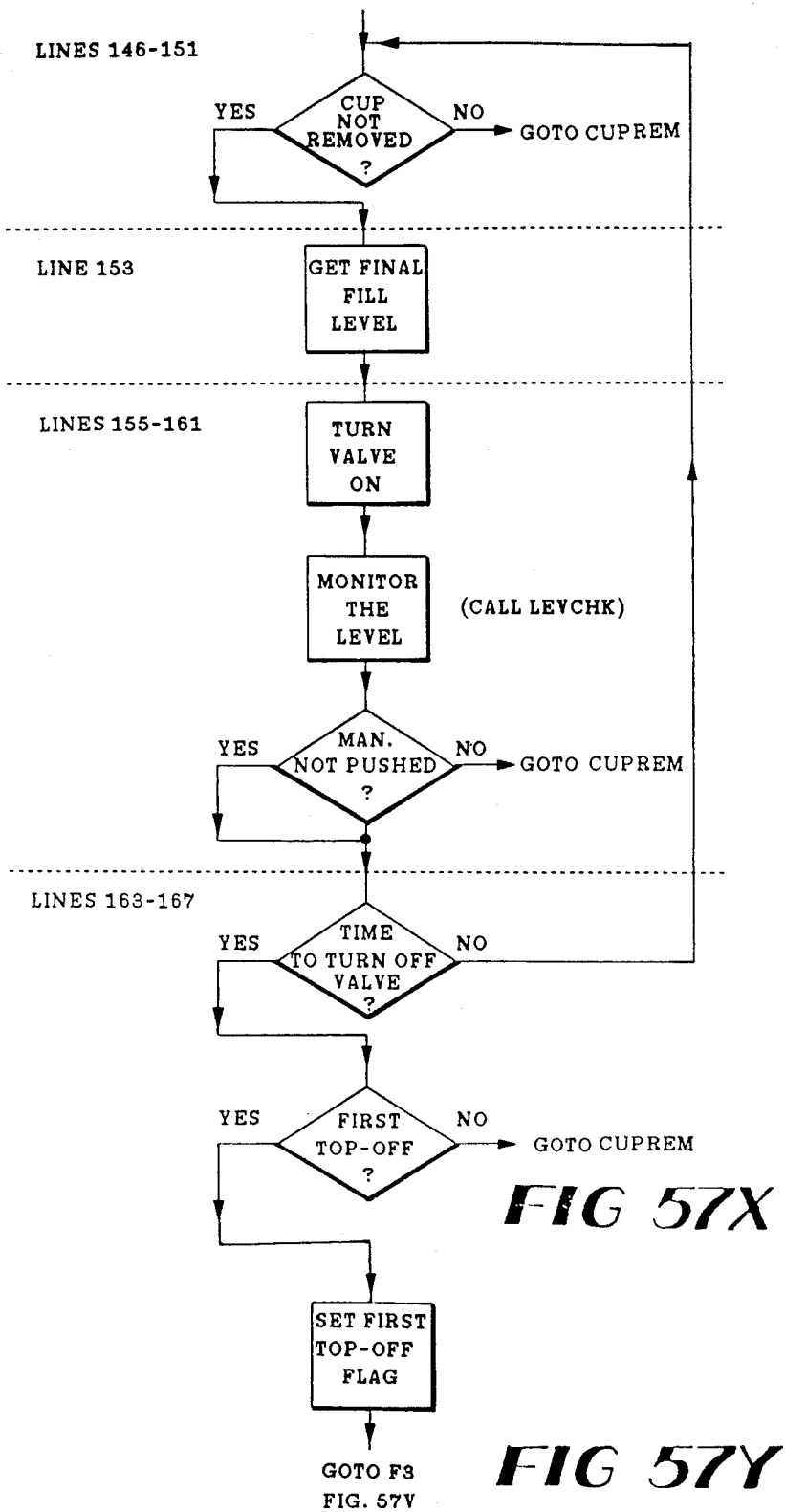

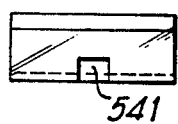
FIG 58A
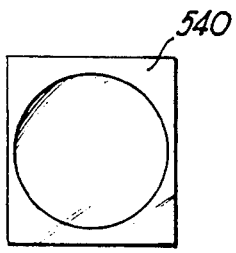 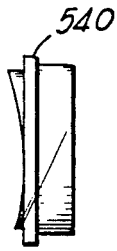 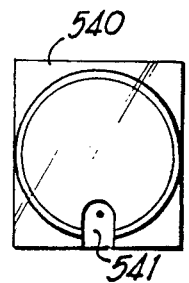
FIG 58B  FIG 58C  FIG 58D
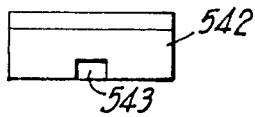
FIG 59A
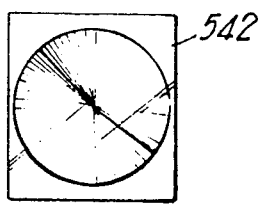 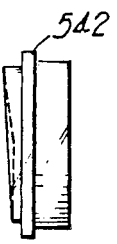 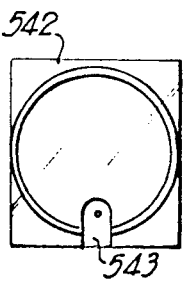
FIG 59B  FIG 59C  FIG 59D

AUTOMATIC CONTROL SYSTEM FOR FILLING BEVERAGE CONTAINERS

CROSS-REFERENCE TO RELATED APPLICATION

This application is a continuation-in-part of prior application Ser. No. 048,111, filed May 8, 1987, having the same title as this case, which was a continuation-in-part of prior copending patent application Ser. No. 684,215, filed Dec. 20, 1984, having the same title as this case, and now abandoned which application was in turn a continuation-in-part of prior application Ser. No. 629,397, filed July 10, 1984 and entitled Ultrasonic System for Automatically Filling Beverage Cups, and now abandoned

BACKGROUND OF THE INVENTION

1. Field of the Invention

This invention relates to beverage dispensing and more particularly to an ultrasonic system for automatically controlling the filling of beverage containers, such as with post-mix carbonated soft drinks.

2. Description of the Prior Art

Heretofore, attempts have been made to provide apparatus to automatically fill beverage containers, such as cups, in response to the proper positioning of a cup under a nozzle of a dispensing valve assembly of a beverage dispenser. Such apparatus used, for example, liquid level detectors such as either conductive or capacitive electrical probes to measure the liquid level.

It is also known to measure various liquid levels within containers using ultrasonic energy and associated circuitry.

SUMMARY OF THE INVENTION

An automatic system for controlling the filling of different sizes of beverage containers or cups, which cups may contain various quantities of ice, with a beverage which may or may not foam during filling. The system includes a transducer assembly and a control module, both preferably connected to a beverage dispenser valve assembly. The transducer assembly is mounted adjacent to the nozzle and uses a first crystal to transmit ultrasonic energy (ultrasound wave energy) and a second crystal to receive reflected ultrasonic energy. Both crystals have lenses for providing coupling of the beam between the crystal and the air, and for either producing a shaped beam (the transmitter crystal) or for receiving a beam from a defined area (the receiver crystal). The control module includes a microcomputer and associated circuitry for controlling the filling operation, including determining that a cup is present below the nozzle of the valve assembly, determining that the cup does not have too much ice, filling the cup, waiting for any foaming to subside, topping off the cup to completely fill it, and producing a signal to an operator that the filling is completed.

The control system can use a single pair of crystals (one transmitter end one receiver) or two pairs. In the embodiment using two pairs, one pair looks at just the grate and cup lip and the other pair looks at just the rising liquid level, end each pair employs a different beam shape.

The control system includes at least one ultrasonic transmitter, at least one separate ultrasonic receiver, and control circuit means for generating signals corresponding to the travel time of the ultrasonic energy and for using such signals to automatically detect the presence of a cup and to fill it.

It is an object of the present invention to provide a system to automatically control the filling of beverage cups.

It is another object to provide a bi-static. ultrasonic system to automatically fill beverage cups.

It is a further object to provide such a system that employs signals received from the grate, the cup lip, and the liquid level in the cup.

It is another object to provide a high resolution bi-static ultrasonic filling system in which the container and liquid level are in air and are very close to the crystals.

It is another object to provide such an ultrasonic system in which the receiver gain is maintained at a constant gain during each transmission period for the separate receiver crystal, but the detection level or scheme is changed; in particular the detection scheme is turned down very low until the transmitted beam is about one-half inch below the nozzle, and then the detection scheme is turned on at a constant ramp to compensate for signal loss.

It is still another object to lens the crystals using ABS or polycarbonate plastic.

It is another object of the present invention to provide an ultrasonic system for automatically controlling the filling of a beverage cup, which system: (1) uses a frequency of about 400 KHz, (2) uses a bi-static transducer system, (3) looks at the leading edge of the reflected ultrasonic energy pulses rather than at the trailing edge, (4) masks the cup lip during certain routines, (5) lenses the transducer, (6) uses a lens material that both shapes the ultrasonic beam and also couples it to the air, (7) uses a timed fill for the initial fill because of cup vibration and therefore lip vibration, (8) uses a low gain to see the liquid level (which is a better reflector than the lip) but not the lip during certain parts of the routine, (9) looks above the lip (the LGRATE subroutine) and shut off the filling if a signal above the lip (showing overfilling) is received, and (10) measures the filling time and shuts off the filling if the fill time exceeds a maximum time period (to prevent continued filling of a cup with a hole in it, for example).

It is another object of the present invention to provide a system for use on adjacent beverage dispensing valve assemblies to automatically control the filling of beverage cups from such valve assemblies without interference therebetween.

It is a still further object of the present invention to allow placement of ultrasonically controlled valve assemblies in close proximity to each other without interference therebetween.

It is a further object of this invention to prevent unwanted interference from adjacent ultrasonically controlled valve assemblies by synchronizing the operation of adjacent valve assemblies to different half cycles of the a.c. power supply.

It is another object of this invention to use four crystals in an automatic, ultrasonic, filling system, divided into pairs, each having a separate transmitter and receiver.

It is a further object of this invention to employ channelizer tubes to help minimize side lobes.

It is another object of this invention to provide two separate transmitter circuits, one for each of two separate transmitter crystals, and to also provide different transmit periods therefor.

It is a further object of this invention to provide an automatic ultrasonic control system for a beverage dispenser using two transmitter-receiver pairs, and to use different beam shapes with each pair, and to have each pair look at different areas.

BRIEF DESCRIPTION OF THE DRAWINGS

The present invention will be more fully understood from the detailed description below when read in connection with the accompanying drawings wherein like reference numerals refer to like elements and wherein:

FIGS. 4A and 4B are a master block diagram of the automatic control system of one embodiment of the present invention;

FIGS. 14-26 are flow charts illustrating the main routine and the sub-routines of the software for operating the microcomputer 66 in the block diagram of FIG. 4;

FIG. 37 is a schematic circuit diagram of the frequency divider of FIG. 31;

FIG. 38A is a schematic circuit diagram of the dip switch of FIG. 31 and FIG. 38B is a table showing how to set the switches for a desired ice level;

FIG. 39 is a schematic circuit diagram of the front panel module with the manual fill switch and the over-ice and filling indicator lights;

FIGS. 58A-58D are edge, front, side and rear views respectively of the rear lenses; and FIGS. 59A-59D are edge, front, side and rear views respectively of the front lenses.

DETAILED DESCRIPTION OF THE PREFERRED EMBODIMENTS

With reference now to the drawings, a first embodiment of the present invention will first be described with reference to FIGS. 1-26, and then a second embodiment will be described with reference to FIGS. 27-46.

Figure 1:
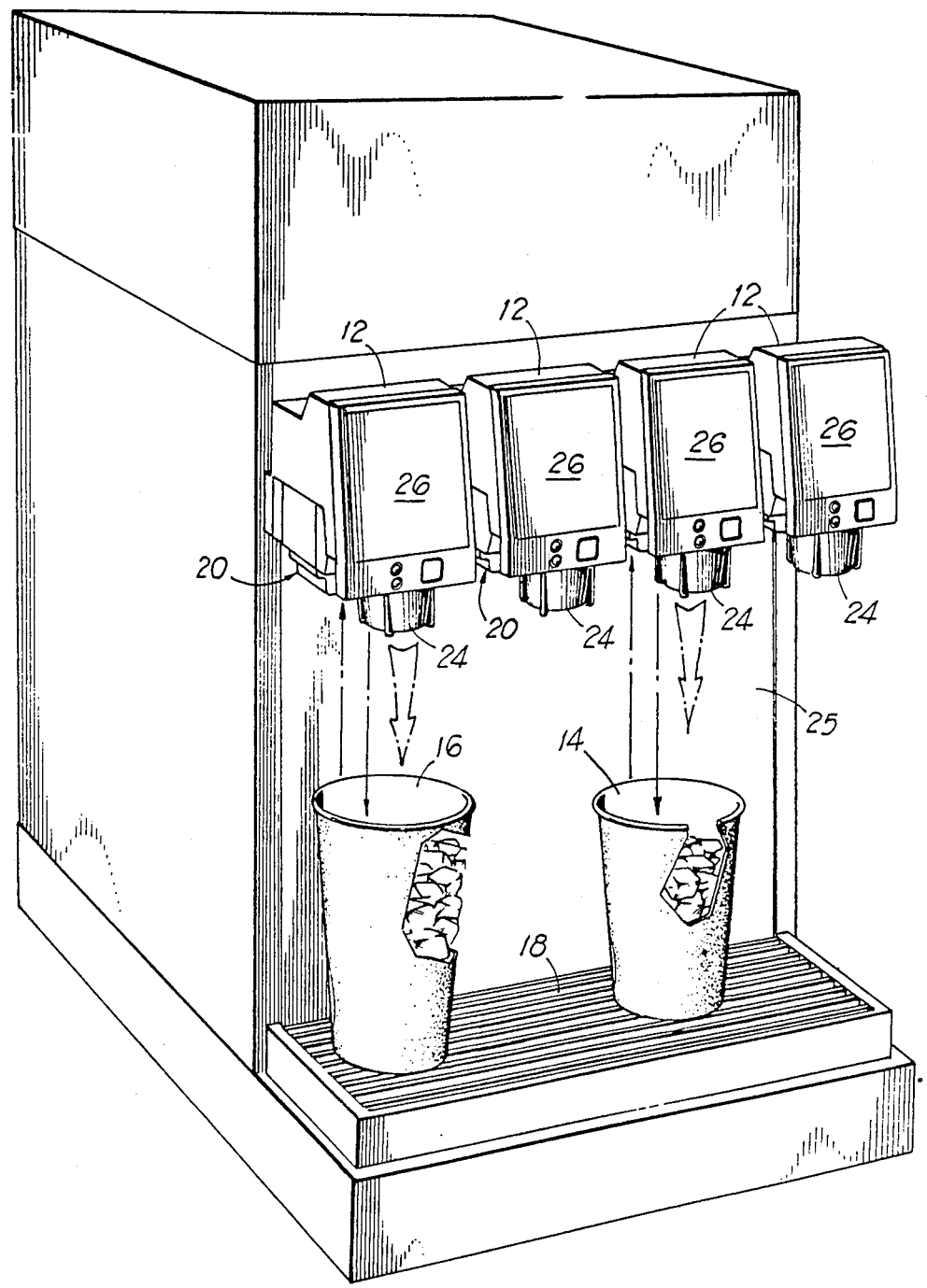
FIG. 1 is a perspective view of a beverage dispenser having four valve assemblies each using the automatic filling system of the present invention.

FIG. 1 shows post-mix beverage dispenser 10 having four identical beverage dispensing valve assemblies 12, each of which has been modified to include the automatic filling apparatus of one embodiment of the present invention in place of the usual cup actuated mechanical lever that normally extends below each valve assembly 12 for operating the two solenoids of the valve assembly (one being for syrup and one being for carbonated water). Each of the valve assemblies 12 is used for dispensing soft drink beverages (usually a different beverage from each valve assembly) into various sizes of cups 14 and 16, supported on a cup supporting surface or grate 18. One particular beverage dispenser 10 and one particular valve assembly 12 is shown, however, any valve assemblies and any beverage dispenser can be used. Beverage dispensers and beverage dispensing valve assemblies, such as those shown at 10 and 12 respectively in FIG. 1, are well-known and thus no detailed description thereof is needed.

Figure 2:
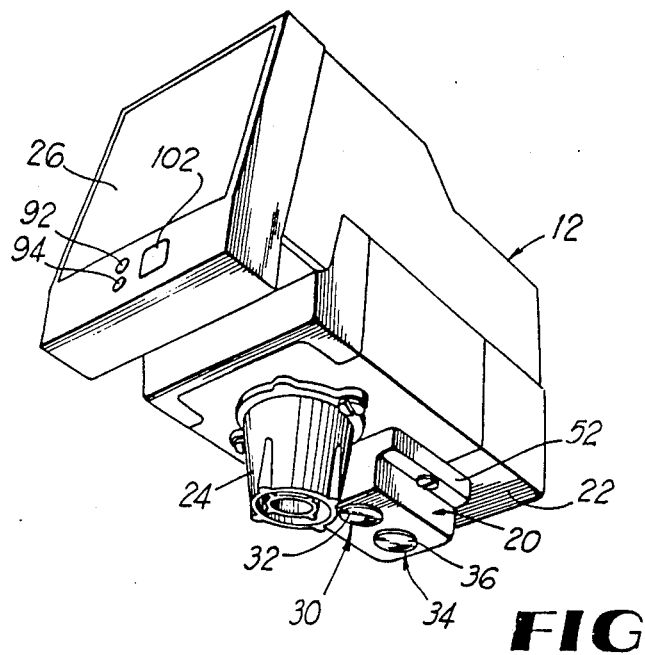
FIG. 2 is a perspective view of one of the valve assemblies of FIG. 1.

With reference to FIGS. 1 and 2, the automatic filling apparatus of the first embodiment of the present invention includes a transducer assembly 20 located on the bottom surface 22 of the valve assembly 12 and behind the nozzle 24, and a control module 26 attached to the front of the valve assembly 12.

Figure 3:
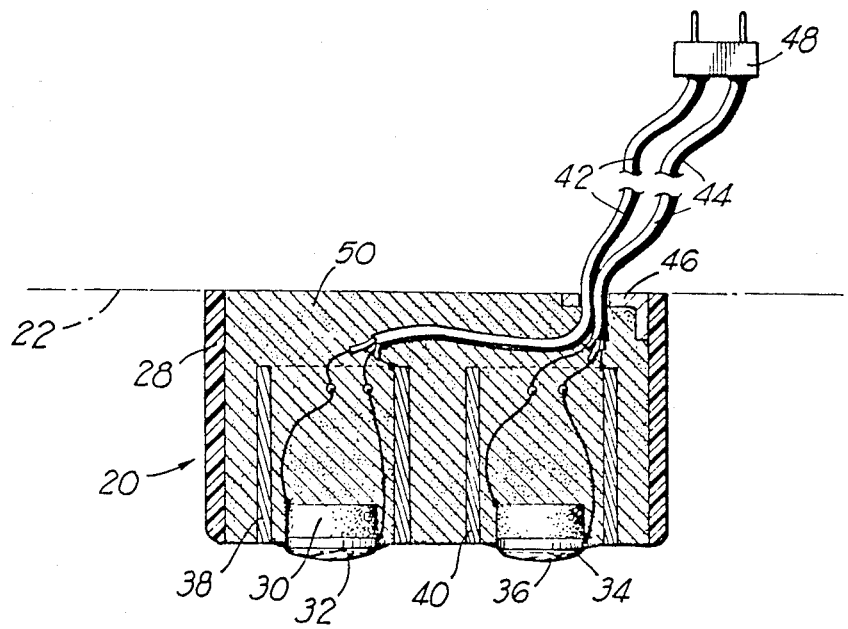
FIG. 3 is a cross-sectional side view of the transducer assembly shown in FIG. 2.

The transducer assembly 20 is best shown in FIG. 3 and includes a plastic housing 28 in which is contained a transmitter crystal 30 having a plastic lens 32, and a receiver crystal 34 having plastic lens 36. The transmitter and receiver crystals are located inside of brass tubes 38 and 40, respectively. A pair of shielded cables 42 and 44 are connected by a clamp 46 to the housing 28. Each cable has a shield wire connected to a respective one of the brass tubes and also a pair of wires connected to a respective one of the crystals at opposite locations thereon, as shown in FIG. 3. Each of the crystals has a metal plating on each of its upper and lower surfaces. The wire connections to the crystals include a pair of 34 gauge wires soldered one each to one of the metal platings on the crystal and then in turn soldered to two 22 gauge wires in the cables 42 and 44. The cables 42 and 44 are about six inches long and terminate in a single MTA connector 48, for connection to the control module 26. All of the space within the housing 28 is filled with urethane foam 50.

The crystals 30 and 34 are preferably PZT-4 ceramic crystals (a generic trade designation for a particular crystal material), which are a combination of lead titanate and lead zirconate. Each of the crystals 30 and 34 is attached to its respective lens 32 and 36 preferably by using about ½ drop of glue such as that sold under the trademark Eastman 910. The plastic lens is preferably made of ABS, polycarbonate, acrylic or polystyrene plastic.

The plastic housing 28 has a pair of flanges (flange 52 is shown in FIG. 2) each having a screw hole for attaching the transducer assembly 20 to the valve assembly 12.

The brass tubes 38 and 40 have the functions of electrically shielding or isolating the crystals, of sound isolating the crystals, and of mechanically holding the crystals (along with the urethane foam which is poured into a mold or fixture used to hold all of the elements of the assembly 20 in place, and which is then allowed to harden).

The selection of the most desirable frequency to use was made as follows. Regarding the upper limit, the attenuation of ultrasonic sound in the air becomes too great to use for more than a few inches at above approximately 600 KHz. In addition, it was desired to avoid the 455 KHz broadcast band IF frequency, and the 550 KHz to 1.65 MHz AM broadcast band. By staying away from FCC assigned frequencies, and by using a transmission that is not too strong in relation to radio stations, interference on radio receivers that are operated in close proximity to the automatic control system of the present invention is precluded.

Regarding the lower limit, because the beam pattern is constricted by the close proximity of other valve assemblies, a 2 inch spread at 14 inches at the 3 db point was assumed for the beam pattern. This 2 inch spread yields an angle of approximately 8 degrees total. Due to the spacing considerations, a ½ inch diameter crystal was selected. A 400 KHz frequency was selected as the preferred frequency. Other frequencies in the range of 200 KHz to 450 KHz could alternatively be used.

Regarding the beam shape, at 14 inches the total maximum beam pattern needs to be less than 3 inches wide at the limits of detectability ($-40$ db) in the side to side direction, and approximately 3 inches front to back at the $-3$ db points. The gain at these points would need to be as flat as reasonable. The crystal pattern was chosen empirically as the one giving the best level gain from front to back with the crystals 30 and 34 aligned from front to back between the nozzle 24 and the splash plate 25. The resulting overall gain pattern with a 3 db gain at 12 inches had a resulting spread sideways of 3.5 degrees, and a resulting spread front to rear of 12 degrees.

To achieve the desired beam pattern, it was necessary to lens the crystals. A 2 inch concave radius produced the 8 degrees to 3.5 degrees narrowing from side to side, and a 4 inch convex radius produced the 8 degrees to 12 degrees spreading from front to rear which formed a fan shaped beam pattern with an elongated footprint having a width of approximately ¾ inch and having a length of about 2½ inches at 3 db gain and 12 inches away from the transducer assembly 20. This beam shape footprint has its long dimension extending front to back relative to the dispenser.

Coupling from the crystals 30 and 34 to the air was calculated as follows:

Characteristic impedance of PZT-4 is equal to $66 \times 10E6$ rayls (E=exponent throughout the following description).

Transmitted power is (Tp)

$$Tp = \frac{(N2/N1)}{(N2/N1) + 1} \times Pc$$

N2 = The characteristic impedance of air.
N1 = The characteristic impedance of PZT-4.
Pc = Power output of crystal.
Tp = $12.6 \times 10E-6$ for 1 watt in, or 0.00126% goes to the air.

If a third material is introduced between the air and the material we get the following equation:

$$Tp = \frac{4(N3/N1)}{((N3/N1) + 1)} \times \frac{(N2/N3)}{((N2/N3) + 1)} \times Pc =$$

$$\frac{4(N2/N1)}{((N2/N1) + 1) + (N2/N3) + (N3/N1)} \times Pc$$

Most materials of interest for the third material have characteristic impedances between $0.1 \times 10E6$ to $10 \times 10E6$ rayls.
For a $0.1 \times 10E6$, Tp = $25 \times 10E-6$
For $10 \times 10E6$, Tp = $22 \times 10E-6$
Thus, for any lossless material used as a coupling to air with a characteristic impedance between $0.1 \times 10E6$ to $10 \times 10E6$ rayls, the resulting input power is at least doubled and the energy transmitted to the air varies by only 10%. The preferred lens material is one of the plastics such as acrylic or ABS. The lens should:

(1) be a plastic for production,
(2) have a ½" diameter and be approximately 0.08 thick,
(3) have a concave radius of 2" in one axis and a convex radius of 4" in the other axis, and (4) be cemented to the crystal face with about ½ drop of glue (preferably that sold under the trademark Eastman 910, or equivalent).

Regarding the lens mount, to diminish acoustic coupling between the receiver and transmitter, the lenses are mounted in polyurethane foam. A brass tube surrounds each crystal and its inner foam mount which provides electrical shielding and is soldered to the shield of the cable wiring to the crystals. The crystals are left floating, i.e., both electrodes are at a potential not referenced to ground. This gives greater electrical isolation in the receiver since it does not pick up ground referenced noise. The brass tubes are held in place by the polyurethane foam to the desired package shape. The lenses protrude from the bottom surface foam package.

Regarding the crystal shape and material, the transmitter crystal is preferably ½" OD×0.200" for a series resonance of 400 KHz. PZT-4 material was chosen for the crystals 30 and 34 as the best compromise in strength, efficiency, and ease of workability. The receiver crystal is preferably ½" OD×0.190" for a parallel resonance of 400 KHz, and is also made of PZT-4 material.

Regarding the electrical wiring, a twisted shielded pair of 22 gauge stranded wire is used. The wire shielding is soldered to the brass tubes 38 and 40. The brass tubes are isolated from each other electrically. A pair of 34 gauge solid wires is soldered across the metal plated crystal faces and is then soldered to the 22 gauge lead wires. All wiring is foamed in place. The black wire of the twisted pair is attached to the outside crystal face which is marked with a small dot.

Figure 4B:
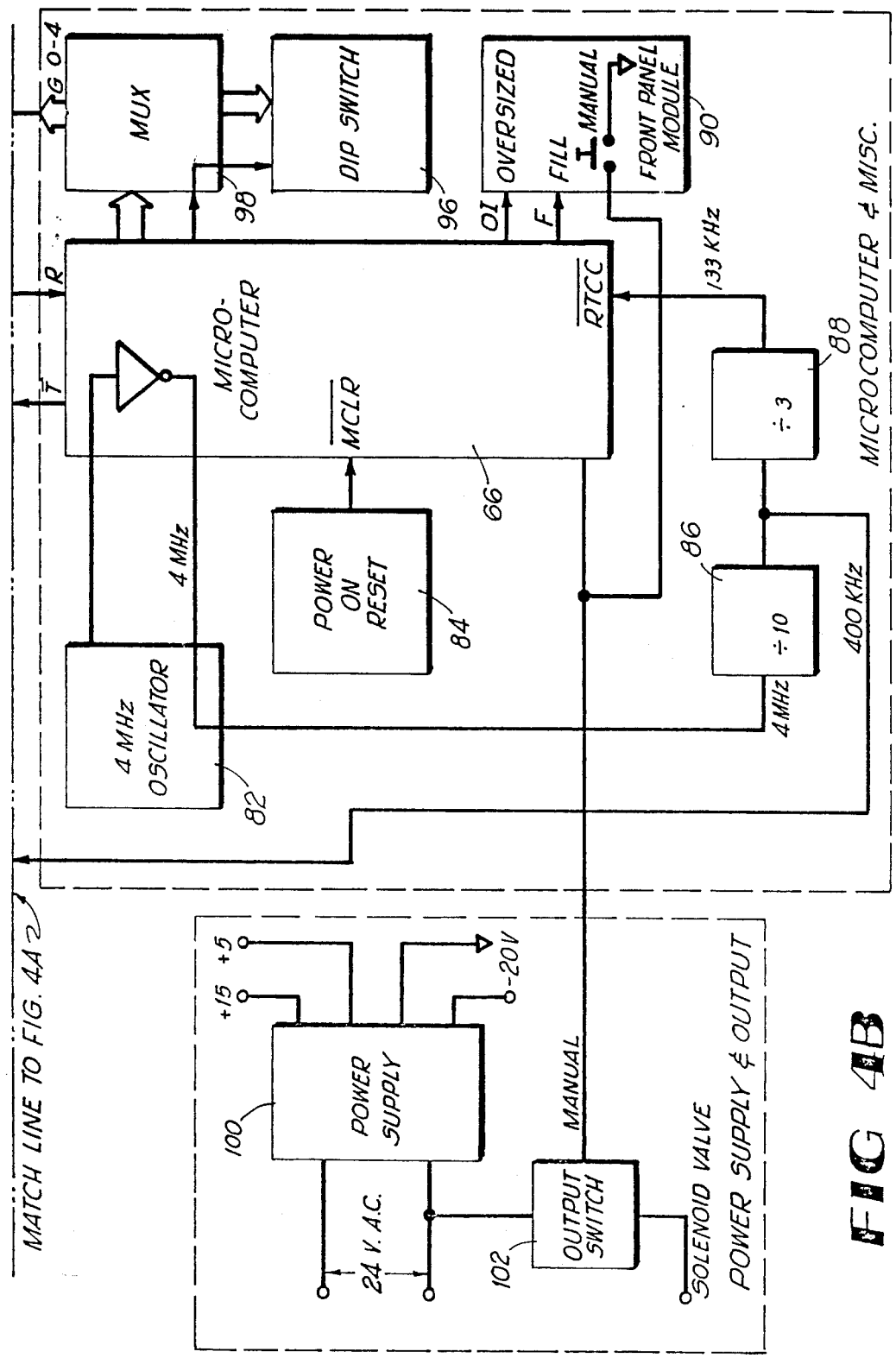
Figure 5:
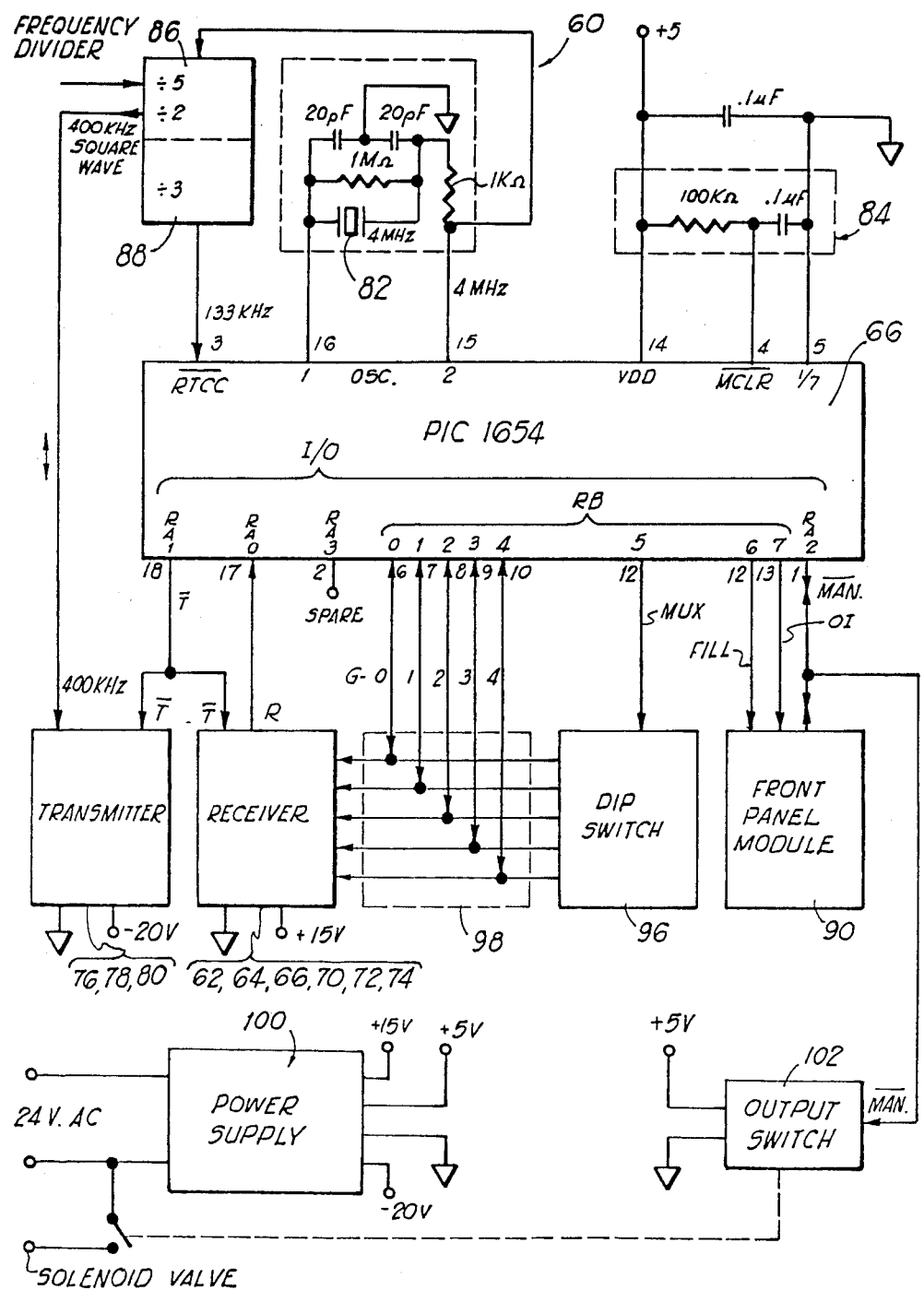
FIG. 5 is a microprocessor block diagram.
Figure 6:
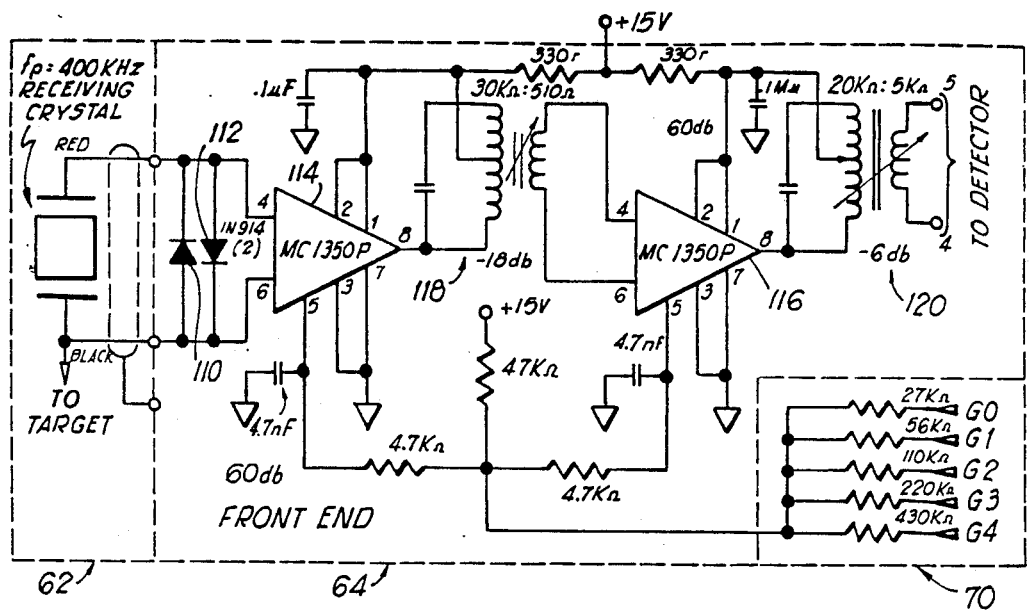
FIG. 6 is a schematic circuit diagram of part of the receiver subassembly including the receiver, the receiver front end, and the D/A gain reduction of FIG. 4.
Figure 7:
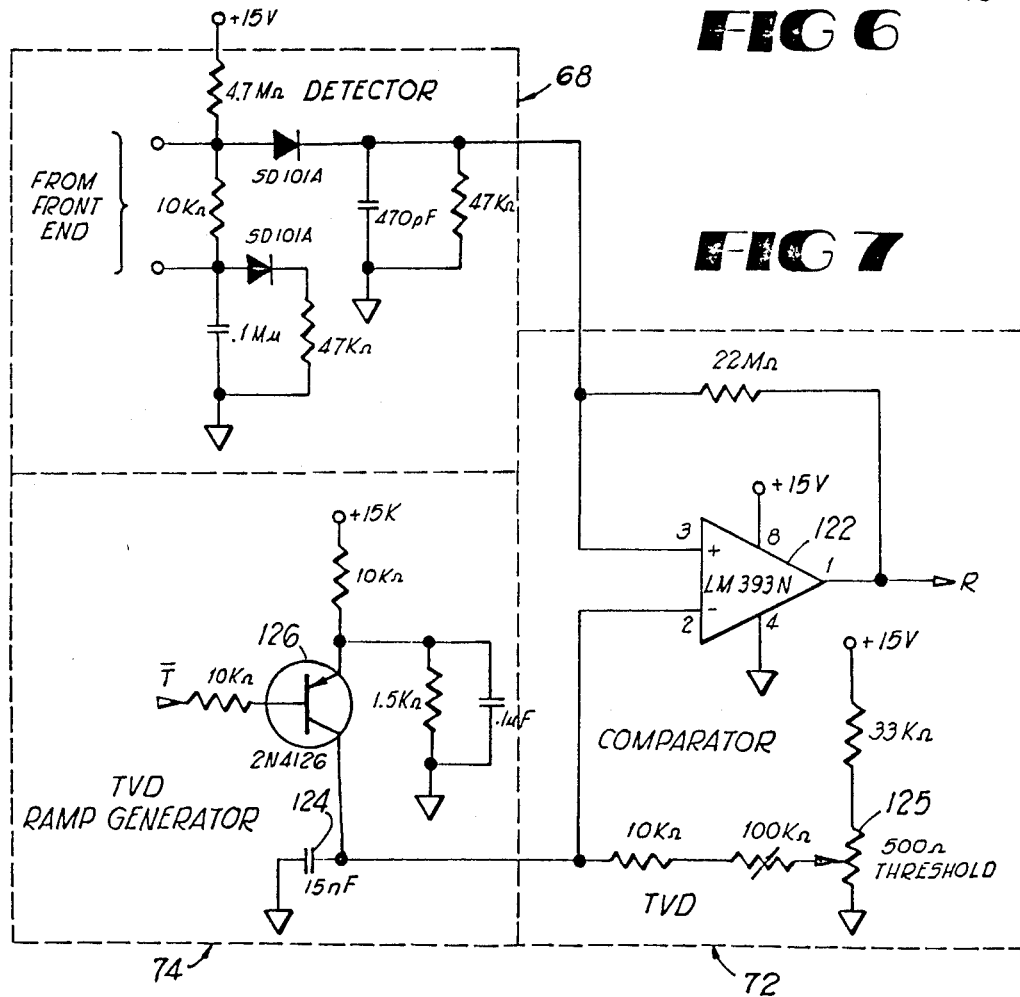
FIG. 7 is a schematic circuit diagram of another part of the receiver subassembly including the detector threshold comparator and the time varying detection generator of FIG. 4.
Figure 8:
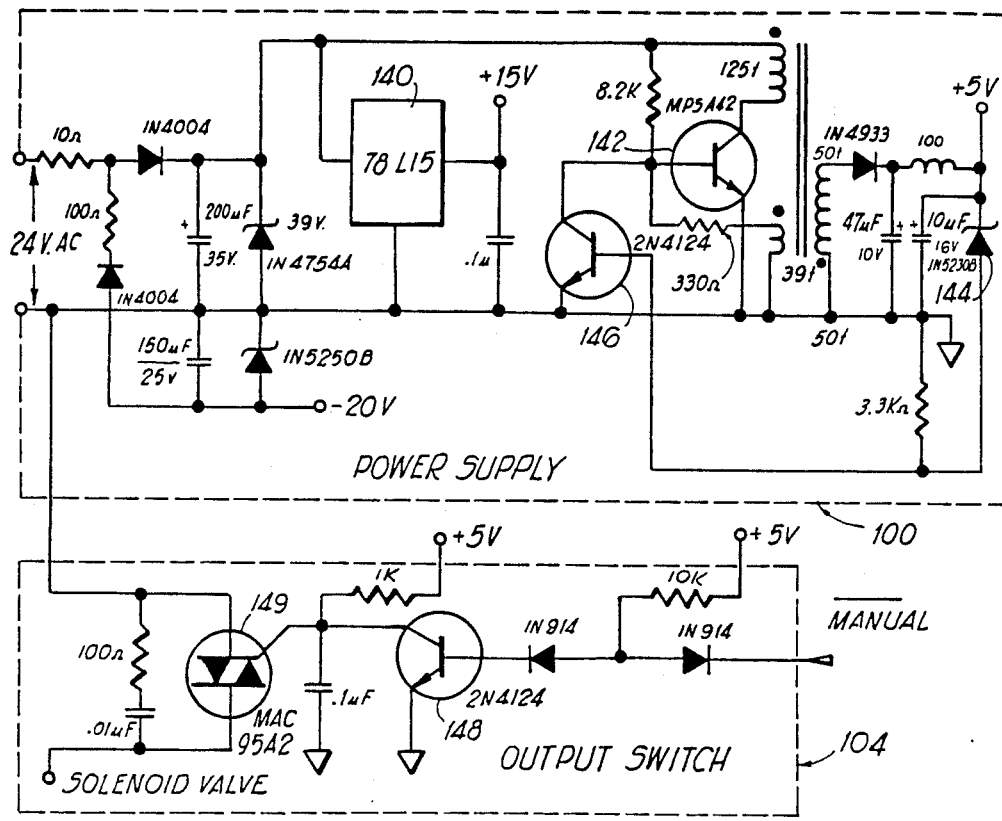
FIG. 8 is a schematic circuit diagram of the power supply and output switch of FIG. 4.
Figure 9:
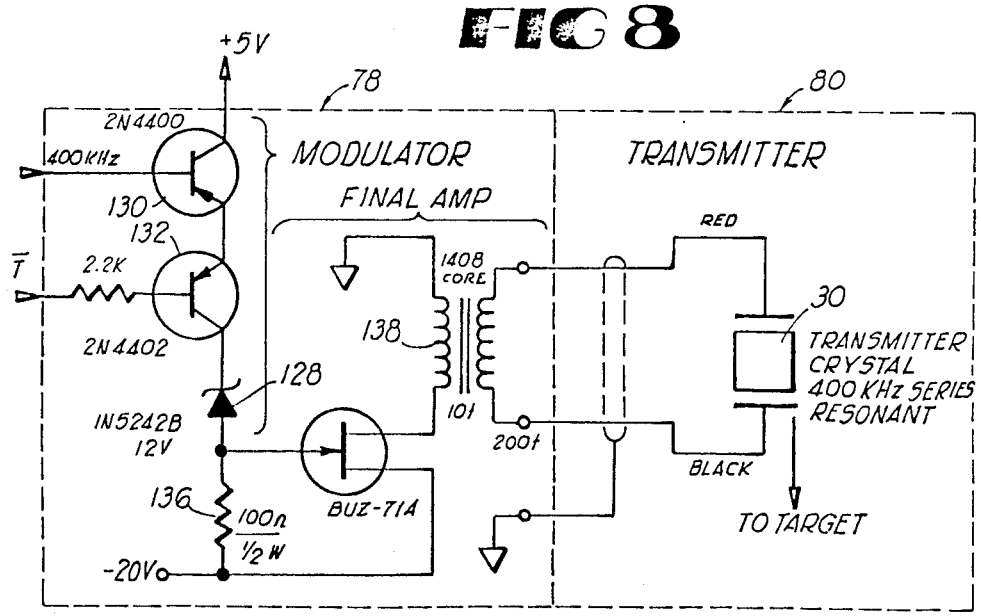
FIG. 9 is a schematic circuit diagram of the transmitter subsystem of FIG. 4.
Figure 10:
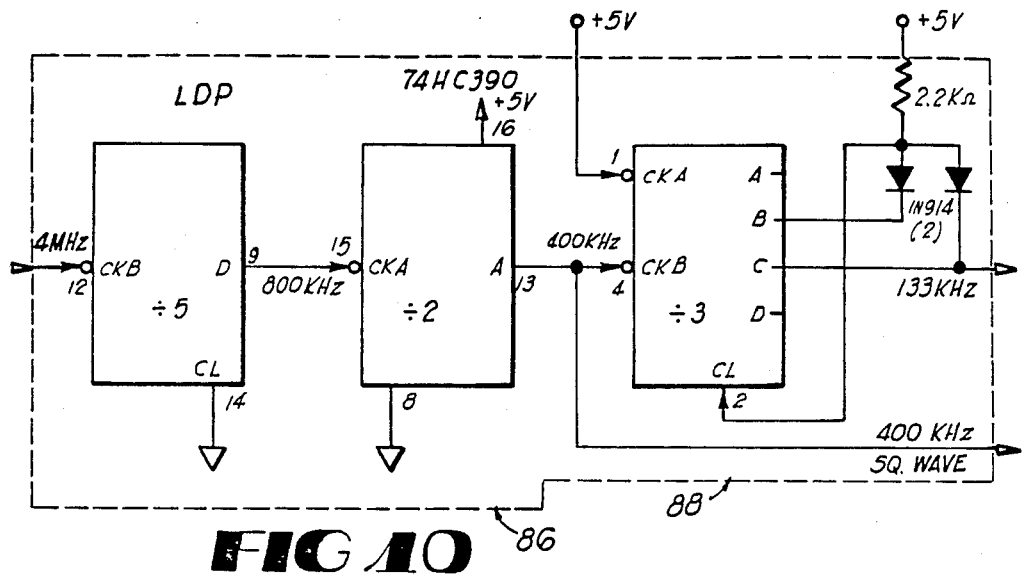
FIG. 10 is a schematic circuit diagram of the frequency divider of FIG. 4.

The control module 26 houses the control circuit board to which the crystals 30 and 34 are connected by the cables 42 and 44 and the connector 48. FIGS. 4A and 4B together provide a master block diagram of the control circuit 60. The control circuit will now be described with reference to FIGS. 4-12.

The receiver transducer 62 (FIGS. 4, 5, and 6) is a 400 Khz, ½ inch diameter parallel resonant piezo-electric crystal 34 made of PZT-4 material. The crystal is coupled to the air by means of a plastic lens 36 which is shaped to receive the beam pattern. The transducer assembly 20 incorporates a brass tube 40 that is ⅝ inch in diameter and is used for electrical isolation. The crystal 34 is mounted such that it is centered in the tube with the lens 36 exposed at one end of the tube. The tube assembly is foamed with polyurethane for acoustic isolation.

The receiver section 64 (FIGS. 4, 5 and 6) has a total gain of 96 db and is comprised of two protective diodes 110 and 112 and two MC1350P IF amplifiers 114 and 116 that are interconnected through a tuned transformer 118 with another tuned transformer 120 to interconnect the second amplifier 116 to the detector 68. These amplifiers 114 and 116 have provisions for gain control from Pin 5 and are used in this application by the microcomputer 66.

The detector circuit 68 (FIGS. 4, 5 and 7) changes the 400 Khz from the receiver 64 to a DC Analog signal. This detector is special in that it can not only detect the envelope of the pulse but since it is a DC coupled detector, it has no offset shift due to pulse width variations. By having a balanced detector system, the temperature drift is very low.

The receiver gain reduction 70 (FIGS. 4, 5, and 6) is comprised of five resistors that form a binary weighted current sinking "D to A" converter that is driven by the microcomputer 66, which allows for thirty-two stages of gain level control.

The threshold comparator 72 (FIGS. 4, 5, and 7) is comprised of an LM393N comparator 122 and is used in conjunction with the time varying detection to convert the analog receiver signal to a digital signal which is then fed to the microcomputer 66. Within this circuit is a means for adjusting the slope of the time varying detector using a 100K potentiometer and a means of adjusting the threshold detector using a 500 ohm potentiometer 125.

The time varying detection generator 74 (FIGS. 4, 5, and 7) uses the gate signal that the microcomputer 66 sends to the transmitter, and charges a 15 Nanofarad capacitor 124 to two volts, which sets the peak level of the time varying detector wave form. This circuit is comprised of a 2N4126 switching transistor 126 and the power supply to support that circuit.

The modulator 76 (FIGS. 4, 5, and 9) is comprised of a 12 volt Zener diode 128 and two transistors 130 and 132 that perform an (Anding) function for the transmitter gate signal (T) and the 400 KHz signal from the oscillator. This (Anded) signal is then level shifted through the 12 volt Zener diode 128 and the 2N4402 transistor 132 to the gate of the final amplifier 78.

The final amplifier 78 (FIGS. 4, 5, and 9) is comprised of a BUZ-71A MOS-FET 134, a resistor 136 and a transformer 138. The resistor discharges the gate source capacitor of the MOS-FET 134. The MOS-FET 134 switches the output transformer 138 to the minus 20 volt supply in response to the gate drive signal. The transformer 138 steps the voltage up to the transmitting crystal 30 to approximately 2000 volts.

The transmit transducer 80 (FIGS. 4, 5, and 9) is comprised of a 400 KHz ½ inch diameter series resonant piezo-electric crystal 30 made of PZT-4 material much the same as the receiver crystal 34 with the exception of the thickness. The crystal 30 is coupled to the air by means of a plastic lens 32 which is also shaped to form the beam pattern. The assembly of the transmit transducer 80 is exactly the same as for the receiver as described above.

The microcomputer 66 (FIGS. 4 and 5) is a General Instruments Pic-1654 and contains the intelligence and control functions of the entire system. It communicates to the rest of the system through twelve I/O pins. It also contains the oscillator circuit, the master clear circuit, and the real time clock counter input.

The crystal 82 (FIGS. 4 and 5) and components of the 4 MHz crystal comprises passive components that form the feedback network for the oscillator in the Pic-1654.

The power-on reset circuit 84 (FIGS. 4 and 5) forms a 10 millisecond reset pulse to the microcomputer 66 at POWER-ON that allows the 4 MHz oscillator crystal 82 to start and the microcomputer 66 to become initialized.

A divide by ten counter 86 (FIGS. 4, 5, and 10) converts the 4 MHz computer clock to a 400 KHz square wave signal to operate the transmitter.

The divide by three counter 88 (FIGS. 4, 5 and 10) converts the 400 KHz signal to a 133 KHz signal that is applied to the microcomputer 66 as the real time clock counter input. Number thirteen and number fourteen are encompassed within the same IC (74HC390) divider chip which has a divide by ten and a divide by three circuit.

The front panel module 90 (FIGS. 4, 5, and 12) consists of two LED indicators 92 and 94. One is an "Over-Ice/Cup Remove" (FIGS. 4, 5, and 12) red indicator 92 and the other is a green "Fill" LED 94, indicating that the cup can be filled or is being filled. This indicator 94 remains "on" steady when a cup is okay until filling starts. In the event that there is too much ice in the cup, or that the cup is not recognized as a cup, the red indicator light 92 will flash on and off.

Figures 11A, 11B:
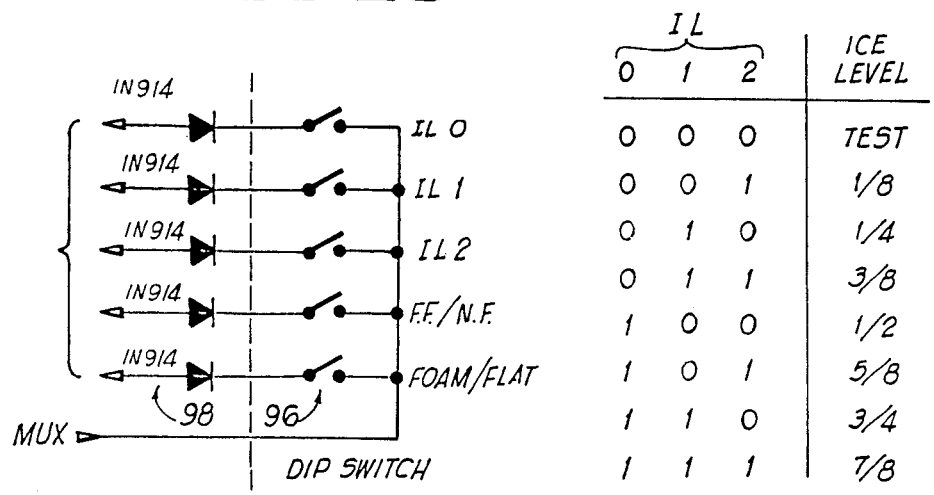
FIG. 11A is a schematic circuit diagram of the dip switch of FIG. 4.
FIG. 11B is a table showing how to set the switches for a desired ice level.
Figure 12:
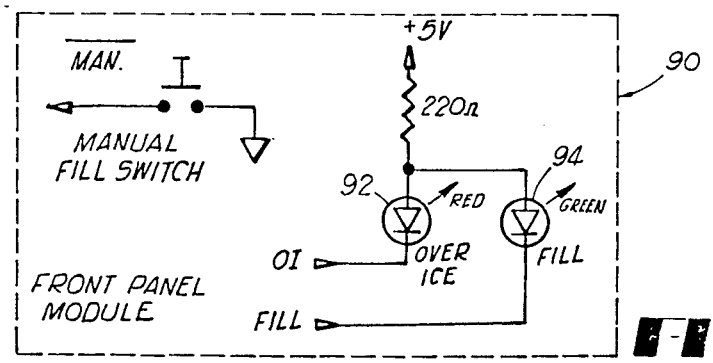
FIG. 12 is a schematic circuit diagram of the front panel module with the manual fill switch and the over-ice and filling indicator lights.

There is a programming dip switch 96 (FIGS. 4, 5, and 11A) comprising five individual switches accessible by removing cover (not shown) on the lower rear surface of the control module 26. One switch is used to select between a normal flow or a fast flow valve assembly, depending upon which type of valve assembly the automatic control system is being attached to. Another switch is used for selecting a foamy or flat product such as water. The other three switches are used for selecting ice level or test position. The test position is used for alignment of the receiver during manufacturing and has no field use. The binary output of the three ice level switches allows for seven ice level selections from ⅛ cup to ⅞ths cup, as illustrated in FIG. 11B.

The multiplexer circuit 98 (FIGS. 4 and 5) allows the microcomputer 66 to read either the dip switches or to set the gain of the receiver as necessary. It is comprised of five signal diodes.

The power supply 100 (FIGS. 4, 5, and 8) uses 24 volts AC from the 50 VAC transformer (not shown) in the dispenser 10. The present control system consumes less than 2 volt-amps at 24 volts AC. The 24 volts AC is rectified and filtered to form a minus 20 volt DC supply and a plus 25 volt DC supply. The minus 20 volt supply is regulated with a Zener diode and supplies power to the transmitter. The plus 25 volt supply is unregulated but has a 39 volt Zener diode used as surge protection. The 25 volt DC supply is regulated down to 15 volts for the receiver subsystem by a 78L15 three terminal regulator 140. An MPS-A42 transistor 142 is used as a fly-back oscillator to provide the plus five volts needed to operate the computer circuitry. The 4.3 volt Zener diode 144 connected between the plus five volt supply and the base of 2N4124 transistor 146 serve to regulate the fly-back oscillator.

The output switch 104 (FIGS. 4, 5, and 8) for the two solenoids of the valve assembly 12 is operated from either the microcomputer 66 or the manual push button 102 on the front of the control module 26. The resistor diode network couples the microcomputer 66 and the manual switch 102 to the base of a 2N4124 transistor 148 which then turns the output triac 149 on or off, which then turns the two solenoids in the valve assembly 12 on or off.

Figure 13:
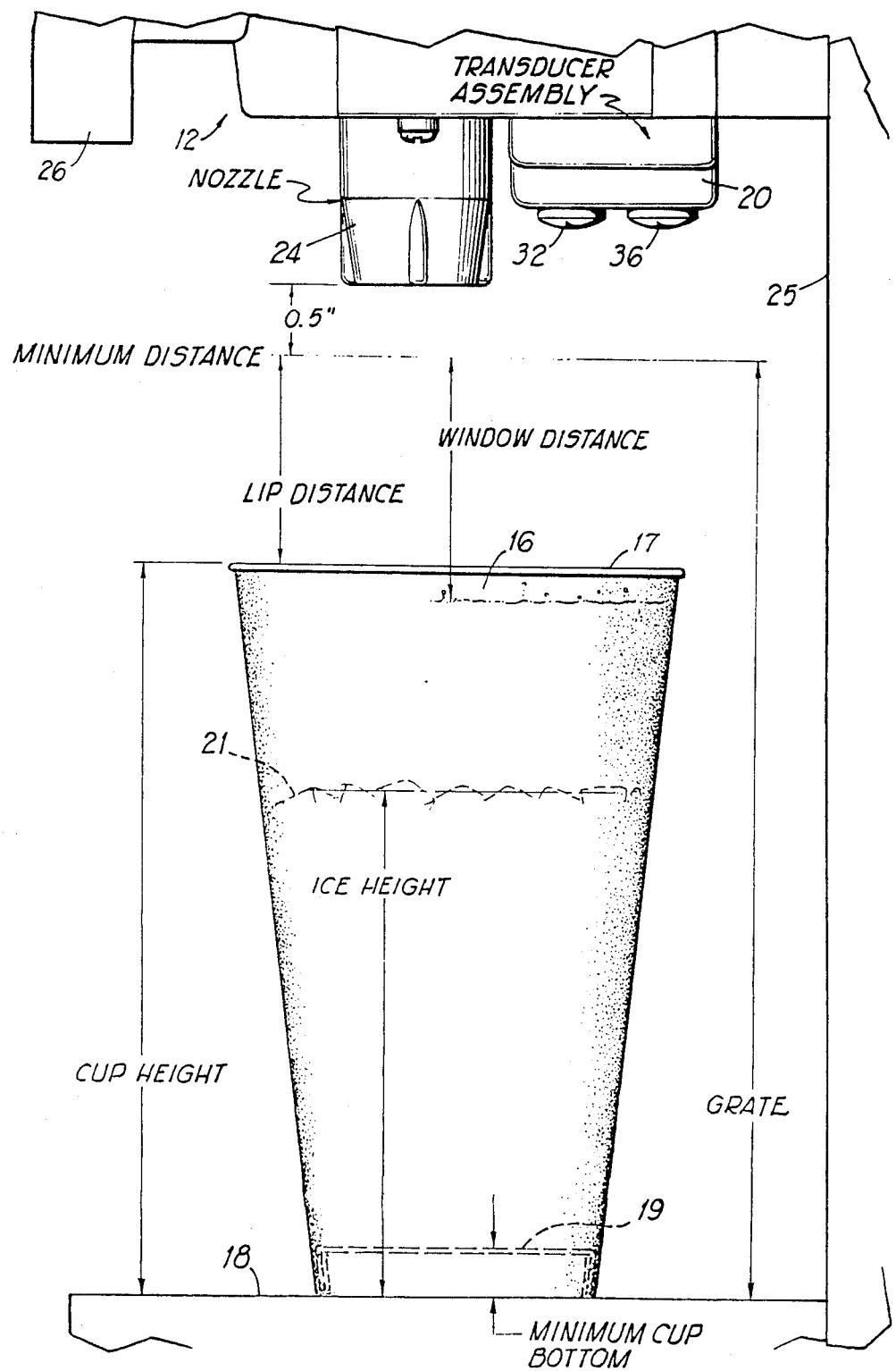
FIG. 13 is an elevational view showing a nozzle, the transducer assembly, the grate, and a cup.
Figure 14:
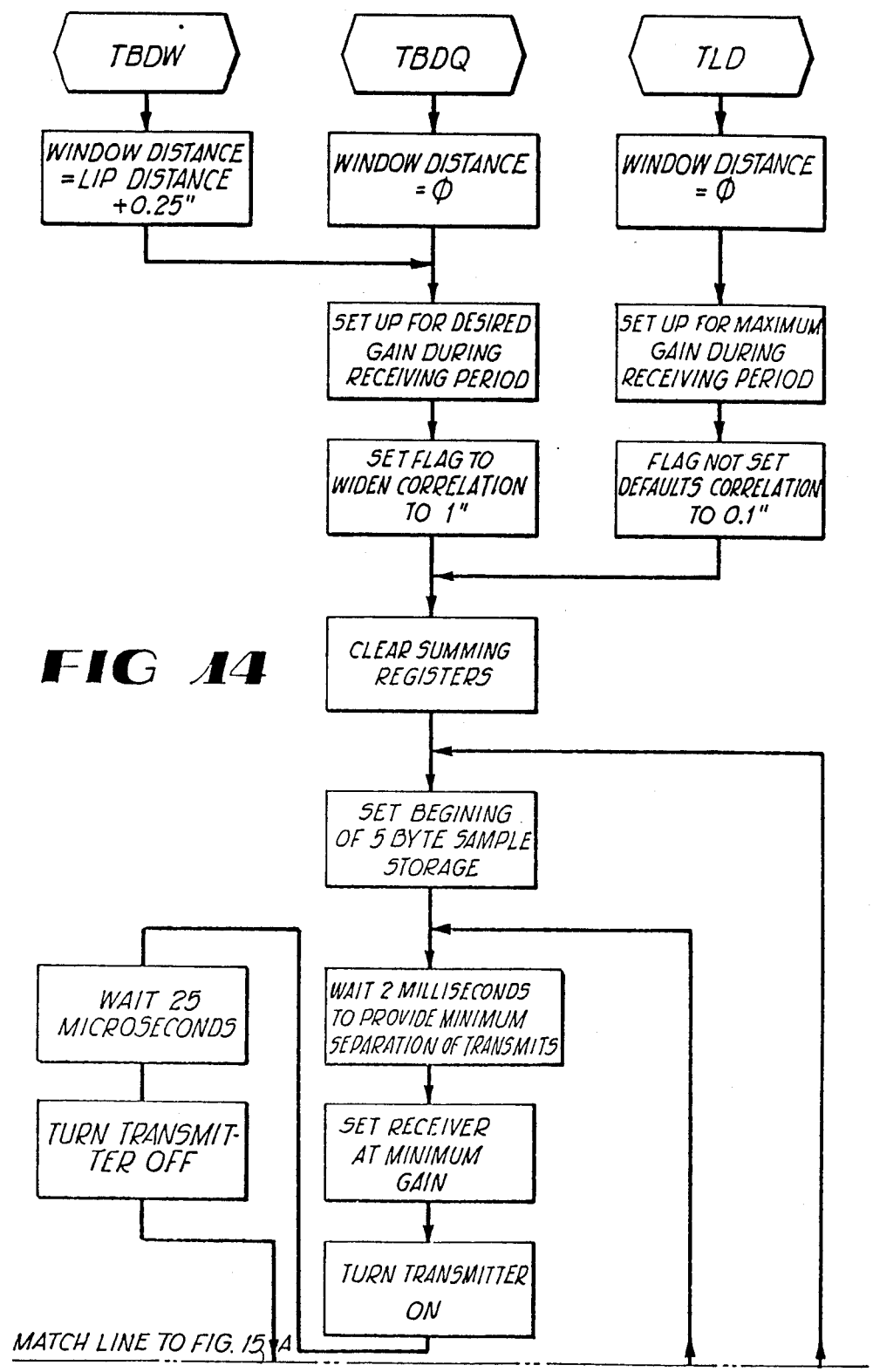
Figure 15C:
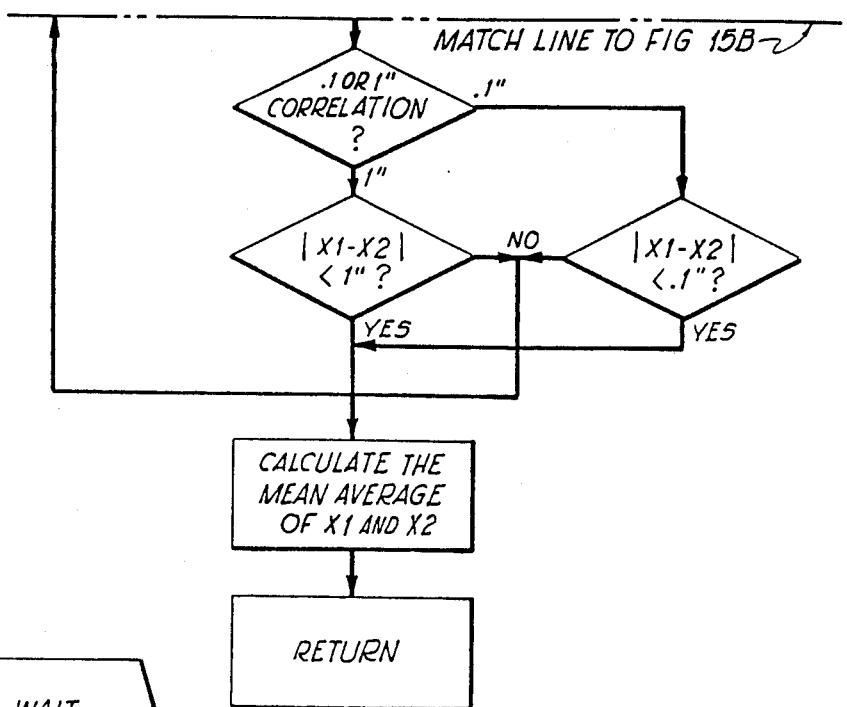
Figure 16:
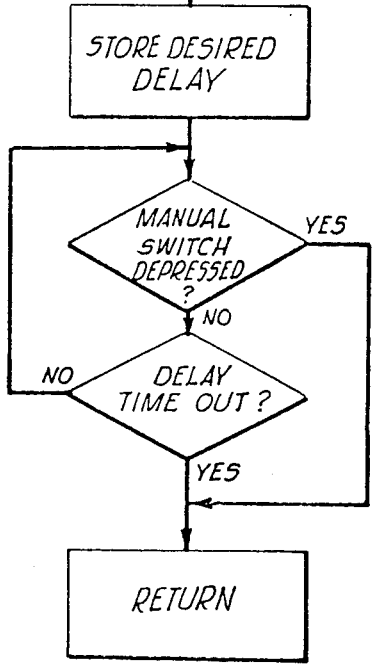
Figure 17:
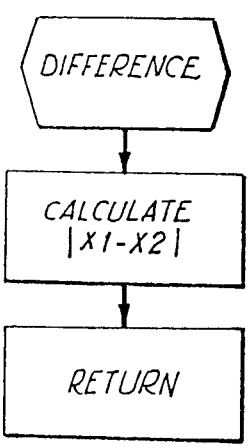
Figure 18:
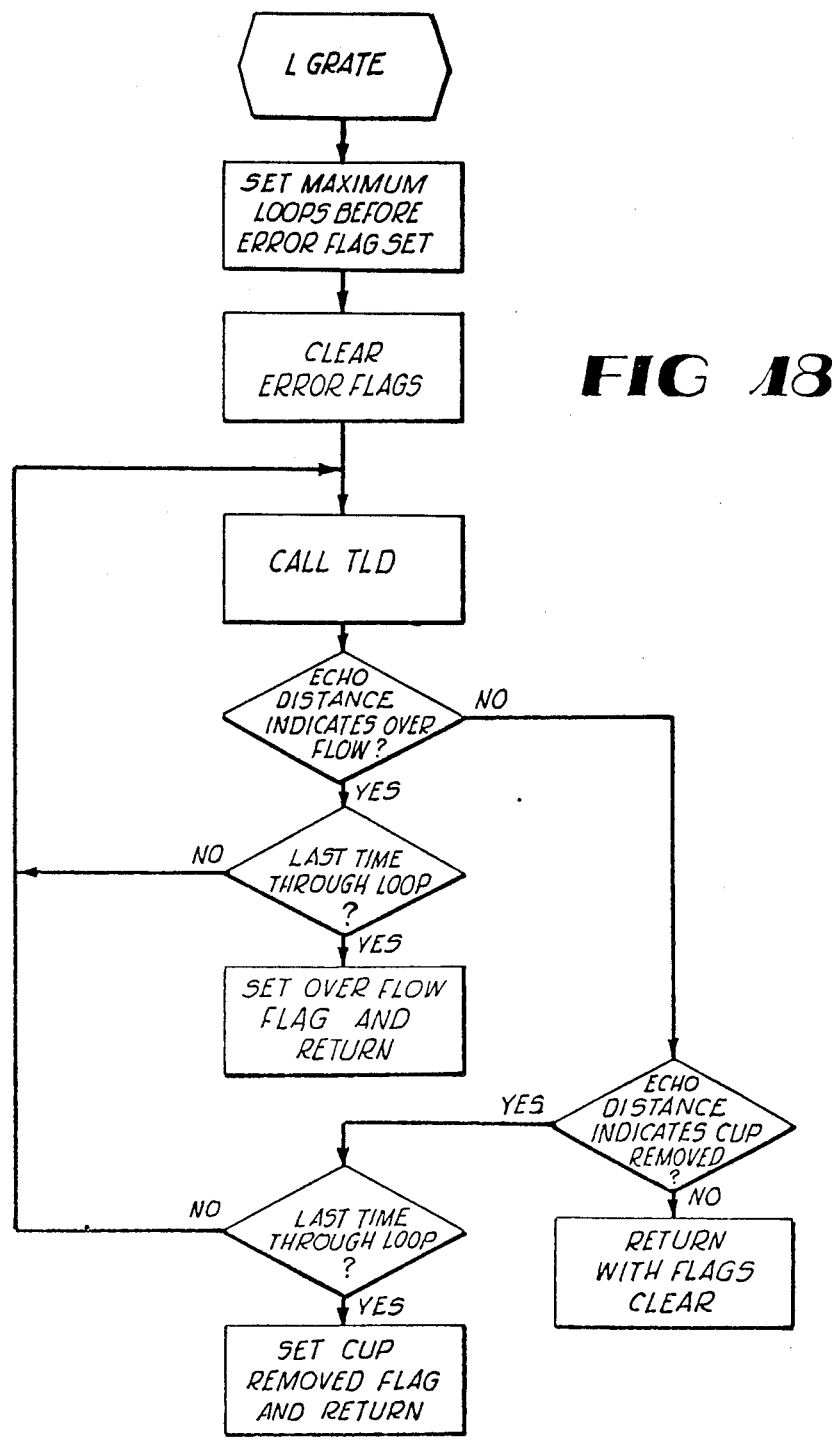
Figure 19:
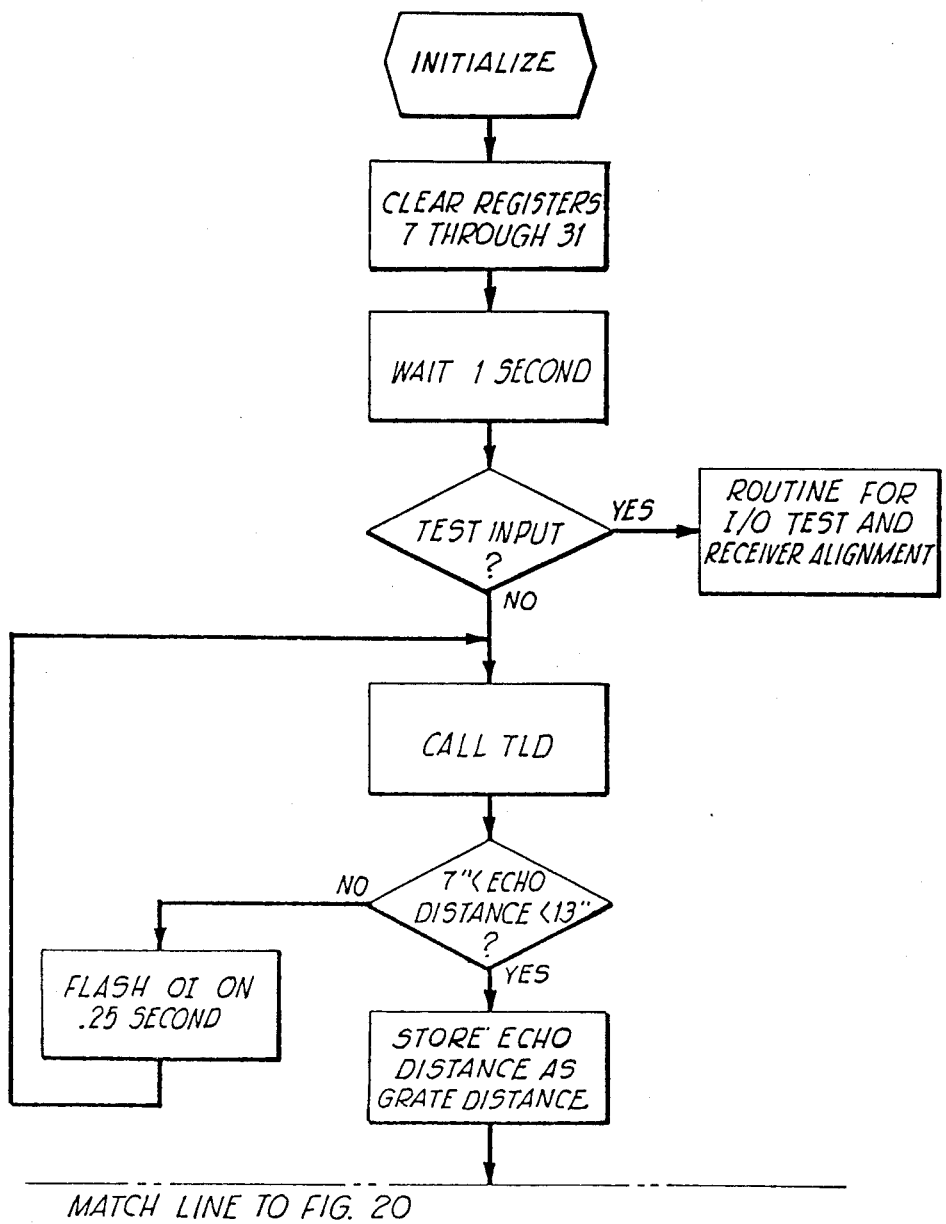
Figure 20A:
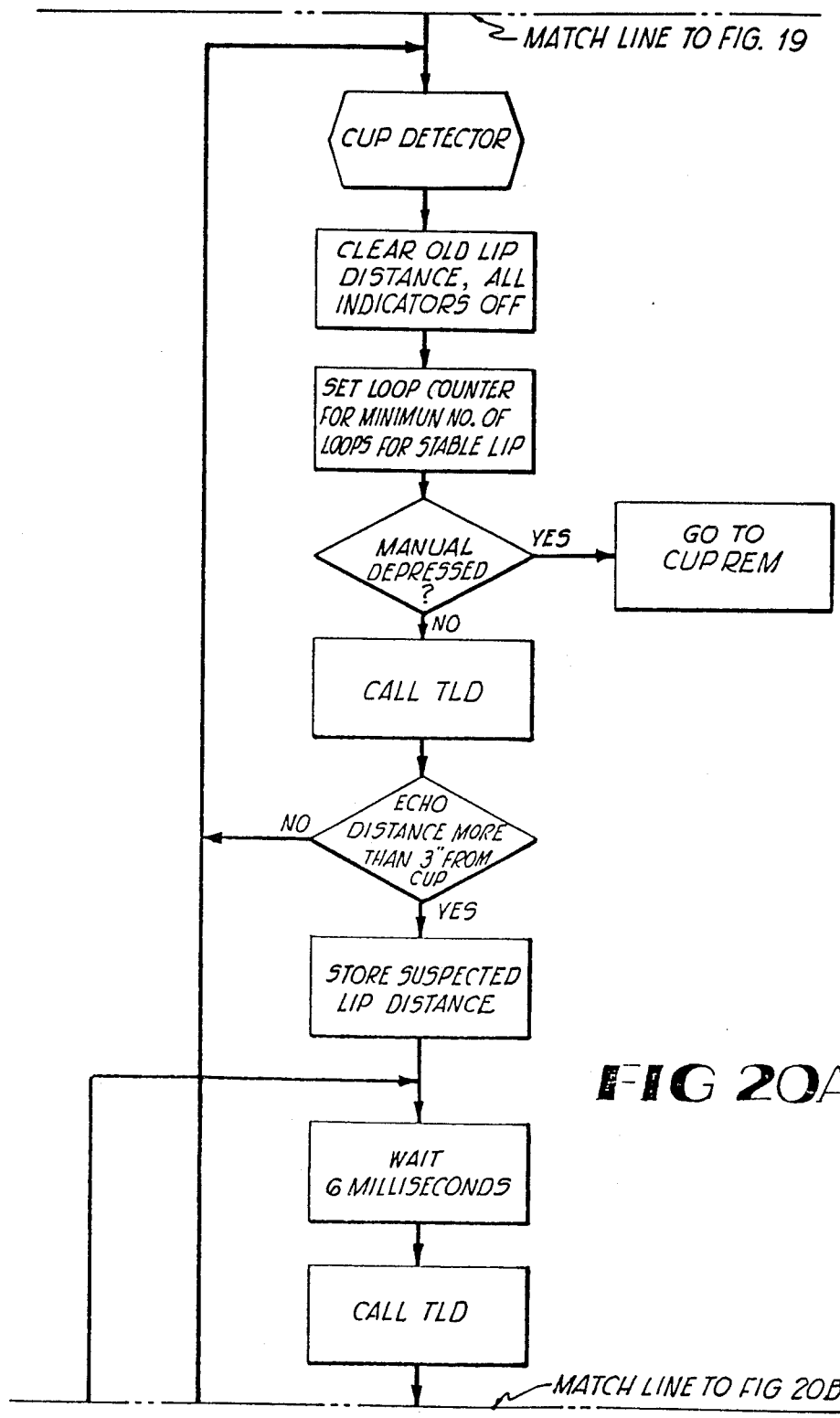
Figure 20B:
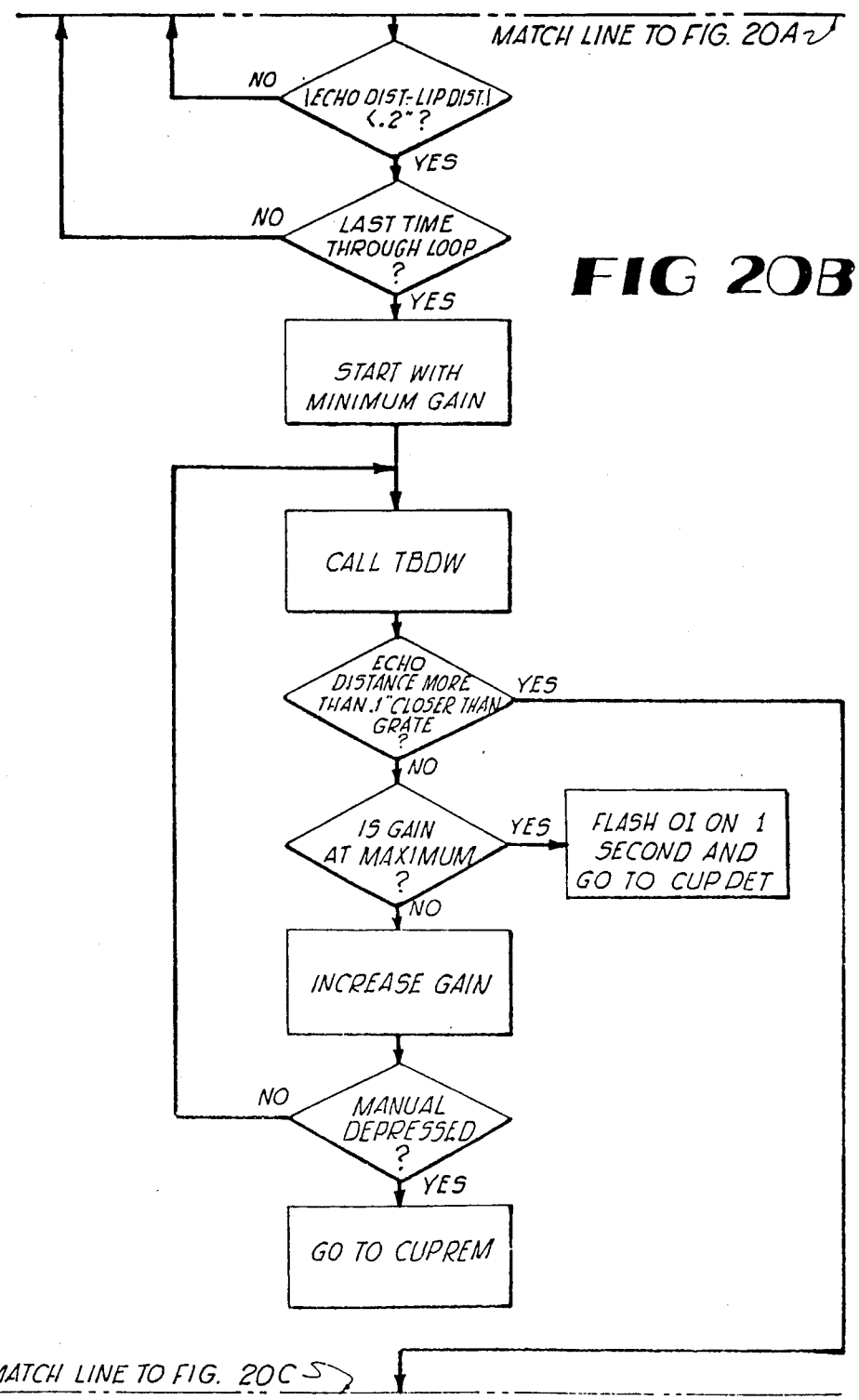
Figures 20C, 21A:
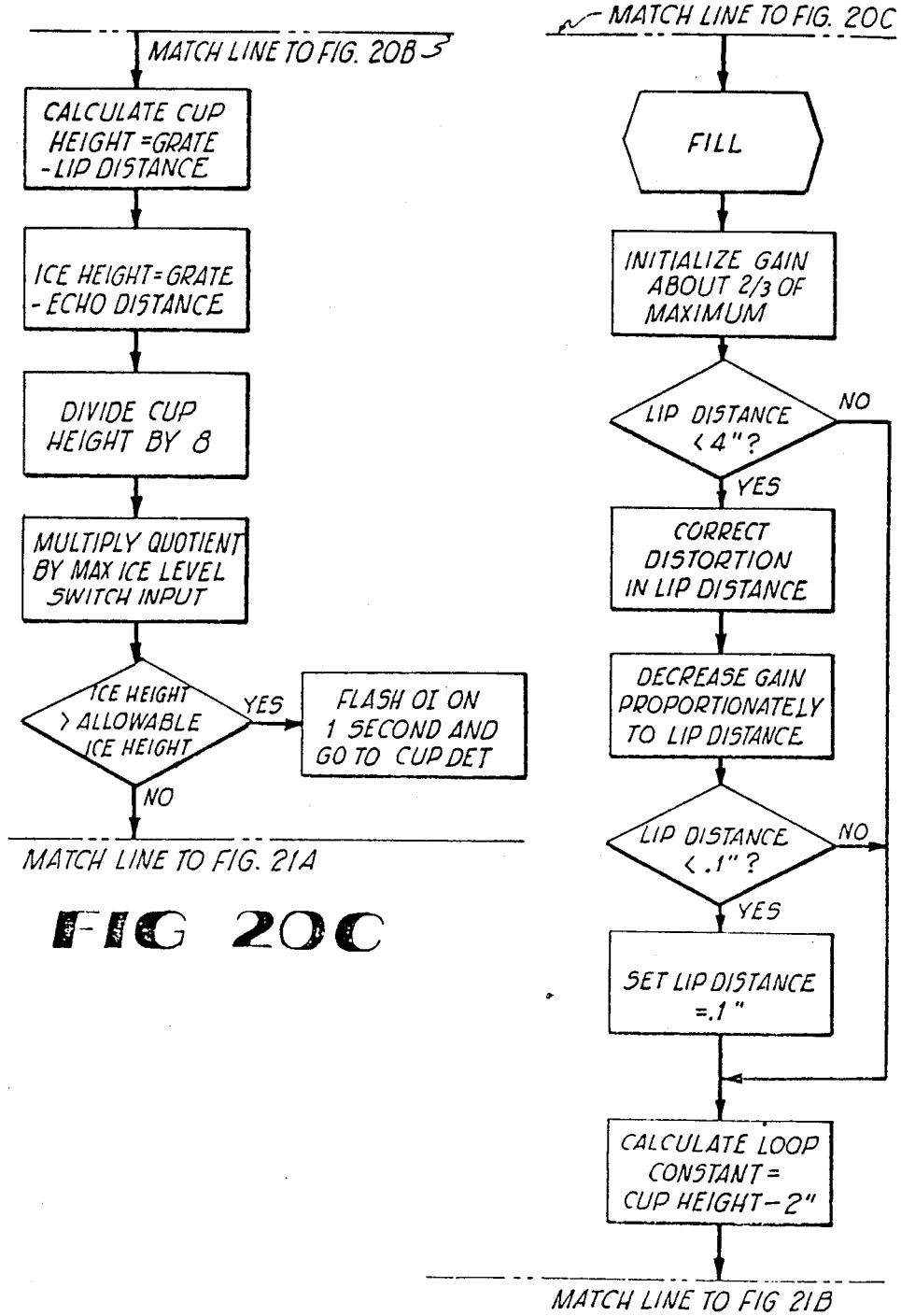
Figure 21B:
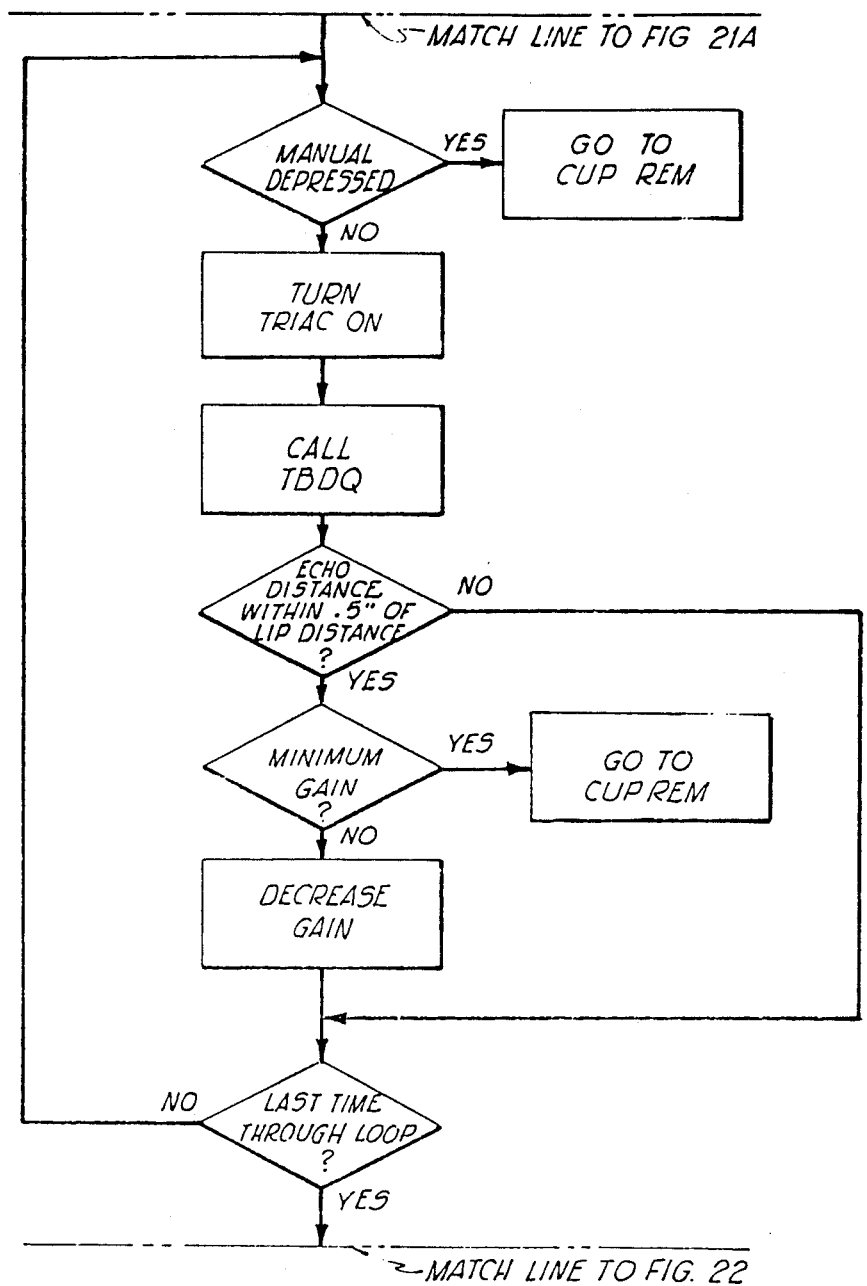
Figure 23:
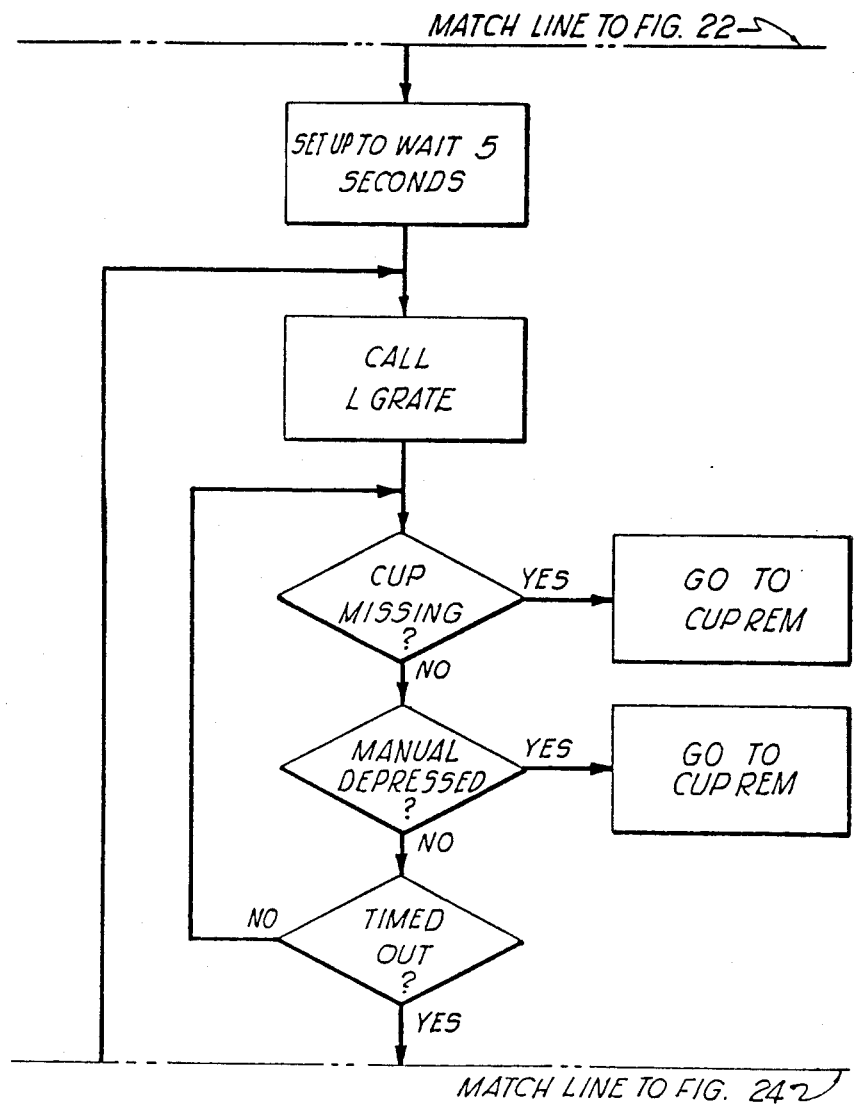
Figure 24:
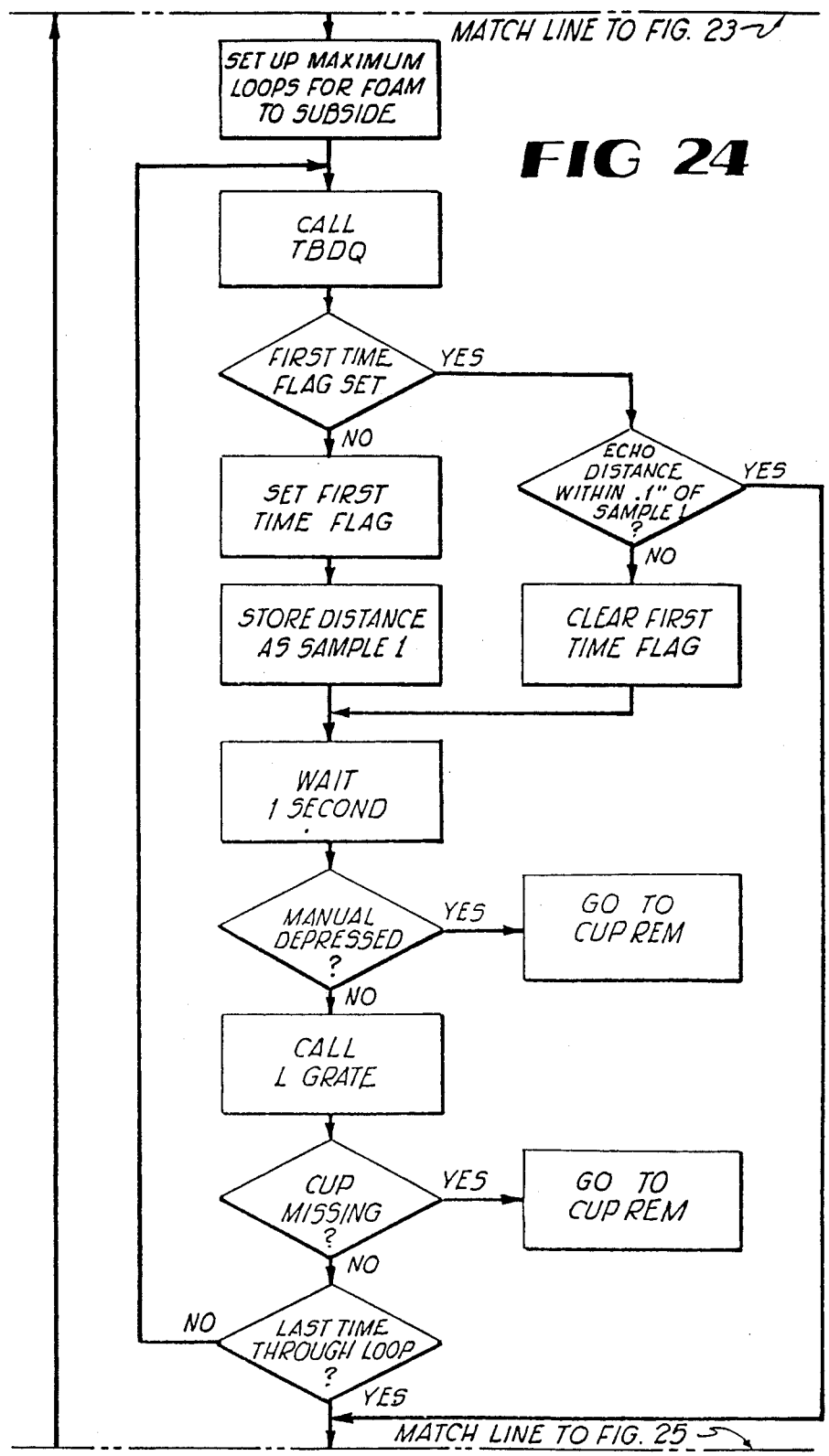
Figure 25:
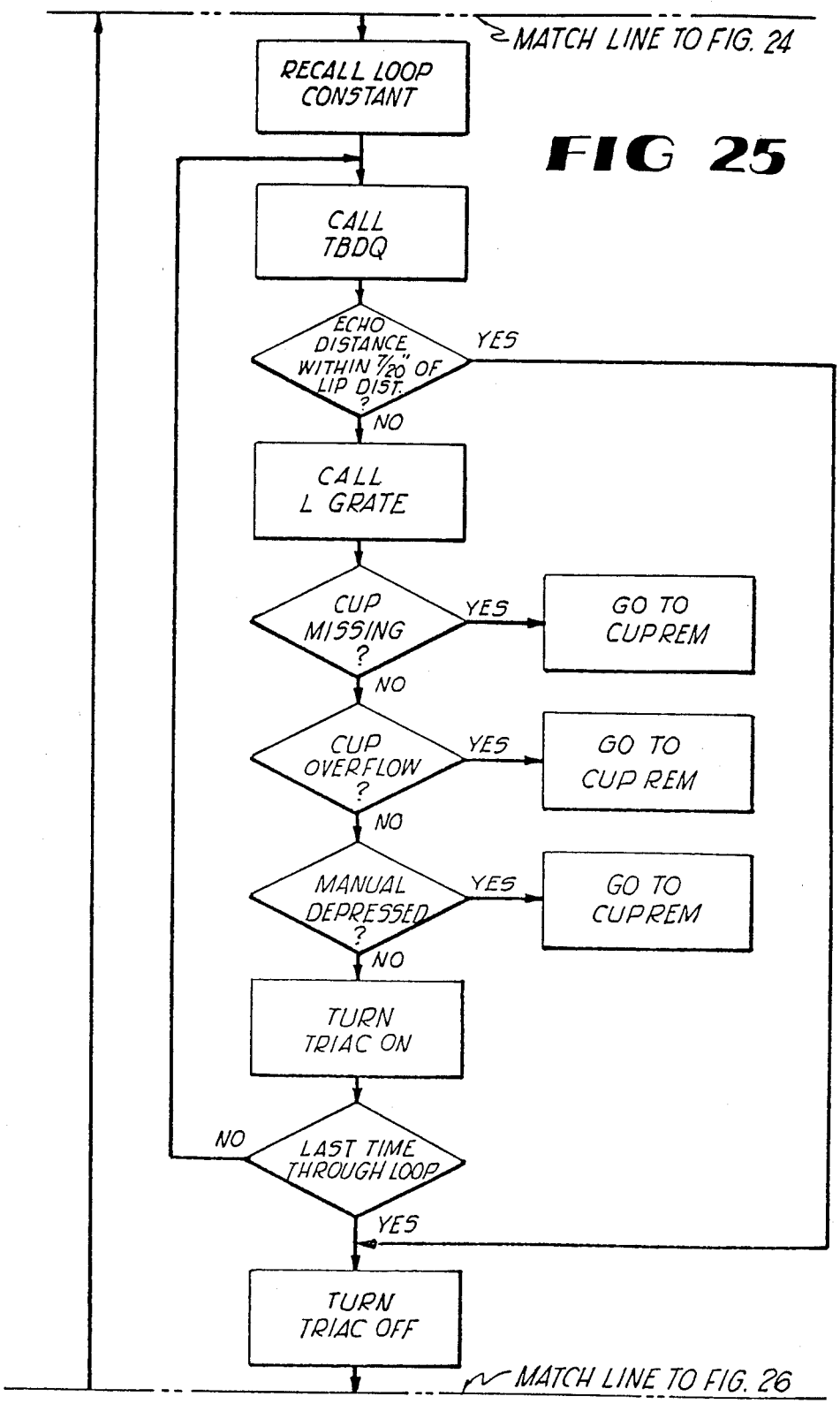
Figure 26:
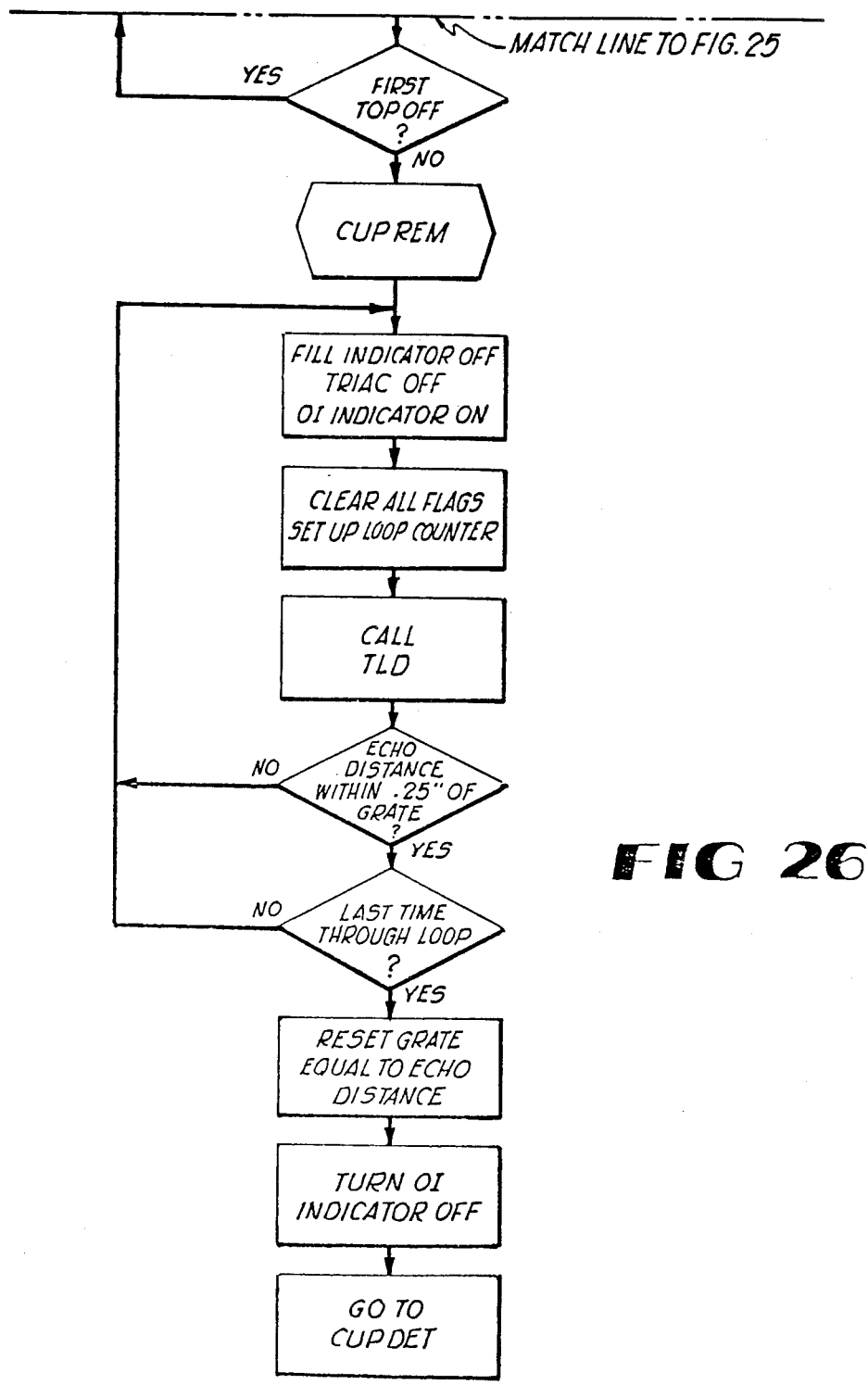

The software will now be described with reference to FIGS. 13 through 26. FIG. 13 is a side elevation view showing the transducer assembly 20, the lenses 32 and 36, the nozzle 24 of the beverage dispenser valve assembly 12, the control module 26, the splash plate 25, the grate 18 and a cup 16 having a cup lip 17, a cup bottom 19, and a top level 21 of ice in the cup.

The software includes four (4) major routines which are labeled Initialization Routine (INIT), Cup Detection (CUPDET), Fill Routine (FILL), and Cup Removal Routine (CUPREM).

The software also includes five (5) subroutines that are defined as Time Delay (WAIT), Absolute Value of the Difference of Two Numbers (DIFF), Grate/Overflow Detector (LGRATE), Transmit (TBDQ, TBDW, and TLD as described below), and Receive (REC).

The Transmitter Subroutine sets the variables for the receiver routine and outputs a 25 microsecond pulse (10 cycles at 400 KHz which occupies 0.1" air space) during which time the transmitter is active. The selection of receiver variables is made through three different entry points (or surfaces off which the transmitted beam reflects): TBDQ (Transmit Bottom Detector), TBDW (Transmit Bottom Detector with window), and TLD (Transmit Lip Detector).

The receiver has 32 steps of gain controlled by the software. The gain is set to minimum from the start of transmit to approximately 1.3" target distance time (180 microseconds). At that time the gain is set equal to the gain variable set up in the entry point routines. For TLD, the gain is always set to maximum. For TBDQ and TBDW, the gain is determined by the calling routine. In TBDQ and TLD, the distance of the first echo detected is captured for processing. In TBDW, a lip masking window is enabled which ignores any echoes closer than the lip distance +0.25". This allows a higher gain to be used to look at liquid level rising inside the cup. Under all entry points, 5 transmissions and receptions are made with the echo distances stored in RAM. The processing algorithm looks for two samples that correlate within 0.1" for TLD, or 1" for TBDQ and TBDW. The average of the two distances is used as the echo distance. A 2 millisecond delay is incorporated before each transmit to allow previous multiple reflections to decay.

WAIT is a programmable delay subroutine that returns to the calling routine immediately if the manual push button is pressed. It has a maximum delay of 1 second.

DIFF is a subroutine that calculates the absolute value of the difference of two numbers.

LGRATE is the Grate/Overflow detector subroutine and is used during the FILL routine. It uses TLD to detect with maximum gain and no window. If the subroutine detects an echo distance less than the lip distance minus 0.1", the overflow flag is set before returning. If the subroutine detects an echo distance within 0.25" of the grate distance, the cup removal flag is set before returning.

INIT is used when the microcomputer is initialized by the "Master Clear" (hardware). During power up, the first instruction processed is at location 777 octal. This instruction "GOTO INIT" commands the computer to begin executing this routine, which comprises the following: (1) the RAM is cleared; (2) wait 1 second for power to stabilize; (3) run the diagnostic routine if enabled; (4) use TLD to look with maximum gain and no window for an echo distance between 7" and 13"; (5) if it does not detect an echo within this range, the "Over Ice" indicator on the front panel flashes; (6) if it does detect an echo distance within 7" to 13", the distance is stored in RAM as the Grate distance and the program continues at CUPDET.

CUPDET is the Cup Detection routine. This routine collects data using TLD and accepts a cup using the following procedure:

A. The manual fill switch on the front panel is monitored continuously to assure proper operation. If the manual switch is pressed, the computer begins the Cup Removal routine immediately.

B. A stable lip distance must be established more than 3" from the grate. A stable lip distance is defined as 5 consecutive echo distances from TLD separated by 6 milliseconds that correlate within 0.2". This corresponds to the cup lip being stable for 130 milliseconds.

C. A cup bottom or ice level must be discerned that is more than 0.1" above the grate and more than 0.25" below the lip. This is accomplished by using TBDW and varying the gain as follows:

With minimum gain, obtain an echo distance using TBDW. If the echo distance is not more than 0.1" closer than the grate, then the gain is increased 1 step and another sample is taken. If the gain reaches the maximum, the Over-Ice indicator flashes and the Cup Detection routine begins again.

D. The ice/bottom height is calculated from the last distance obtained as outlined in (c) above and the grate, and then stored as the actual ice height. The cup height is calculated from the lip distance and the grate. The cup height is divided by 8 and the quotient is multiplied by the 3 bit binary number input as selected on the ice level programming switches. This allowable ice height is compared with the actual ice height. If the actual ice height is greater than allowed by the switch selection, the Over-Ice indicator flashes and the Cup Detection routine begins again. If the actual ice height is less than the amount selected by the switch, the FILL routine begins.

The FILL routine controls the complete filling and top off operation. The routine limits the solenoid operation to a maximum of 3 On/Off cycles. After each of the first 2 cycles, the routine waits for the foam to settle before starting the next cycle. After the foam is settled and the cup is within 7/20" of being full, the Cup Removal routine begins. If the manual switch is pressed at any time during the FILL routine, the Cup Removal routine begins immediately. Each of the cycles has a maximum solenoid on time which if exceeded causes the Cup Removal routine to being.

A detailed description of the FILL routine follows:

A. Before the valve assembly 12 solenoids are actuated, several checks and corrections are made. The gain is initially set at 11/16 of maximum gain. If the Lip Distance is less than 4", the gain is adjusted with the empirically derived equation:

Gain=Gain ⅛ (4" lip distance).

If the Lip Distance is less than 4", the Lip Distance is adjusted with the empirically derived equation:

Lip Distance=Lip Distance ⅛ (4" Lip Distance)

If the Lip Distance is less than 0.1", the Lip Distance is set to 0.1" to allow the cup overflow to function properly.

The Time Constant for this particular cup height is calculated with the equation:

Time Constant=cup height 2".

This time constant is used in each of the three cycles to provide a maximum "Solenoids On" time proportional to the cup height.

B. The gain must be adjusted such that the fluid level is detected and the lip is not during the period when the cup vibrates such as at the beginning of a FILL. To accomplish this a period of time proportional to cup height is programmed to allow filling to start and gain enough weight to minimize cup vibration and adjust gain as necessary. During this time period the routine uses TBDQ to check if the echo distance is within 0.75" of the Lip Distance. If it is, the gain is reduced one step. If the gain reaches minimum, the cup removal routine begins. If the cup is removed during this period, the solenoids will not turn off because the Grate/Overflow detector subroutine is not called during the period due to trying to get as many samples as possible to adjust the gain. At the end of the period, the solenoids stay on.

C. A second maximum time period begins that is also proportional to the cup height. During this time period, the routine uses TBDW to monitor the liquid level and turns the solenoids off when the liquid level is within 0.5" of the Lip Distance. The Grate/Overflow detector subroutine checks to see if the cup has been removed or if TBDW has missed the liquid level rising and an overflow is imminent. If the cup is missing, the cup removal routine begins. If there is an overflow indicated, the solenoids are turned off.

D. A 5 second pause begins at this time to allow the foam to settle 0.25" below the cup lip. The Grate/Overflow subroutine checks once each second to ascertain that a cup is still in place. If the cup is missing, the cup removal routine is started.

E. After the 5 second pause, a minimum number of seconds for the foam to subside is set at 16, and once a second, an echo distance is obtained with TBDQ. If 2 consecutive echo distances are within 0.1" of each other, or if the period times out, the top off cycle begins. The Grate/Overflow detector subroutine checks once a second for a missing cup. Once a cup is found missing, the cup removal routine begins.

F. The top off cycle uses TBDQ to determine if the liquid level is within 7/20" of the lip. If this condition exists, the solenoids are not turned on. If the echo distance is not within 7/20", the solenoids turn on until that condition is met.

G. A repeat of "D," "E," and "F" now occurs to implement the second top off cycle.

The cup removal routine (CUPREM) turns the fill indicator 92 off, the value assembly 12 solenoids off, and the Over-Ice indicator 94 on. It uses TLD and waits for an echo distance within 0.25" of the grate. When this condition exists, a new grate distance is stored, the Over-Ice indicator turns off, and the Cup Detection routine begins again.

As described above, the system of the present invention provides an ultrasonic method and apparatus for controlling the automatic filling of beverage cups. The system can be used with any beverage, such as coffee, tea, milk, fruit juice, and carbonated soft drinks. The beverages can produce foam during filling or not. Different sized cups can be used and they can have ice therein.

The system can be used in conjunction with any known, standard beverage dispenser. In the case of carbonated soft drink dispensers, the transducer assembly and the control module of the present invention are located directly on the valve assembly. The cup actuated arm and the microswitch are removed from the standard valve assembly; the triac 149 in FIG. 8 takes the place of the microswitch and simultaneously turns the syrup solenoid and the carbonated water solenoid on and off.

The system of this invention is on and working whenever the power to the dispenser is on. The power is often left on to the dispenser to maintain the refrigeration system on.

A brief overview will now be provided without reference to the details of the system, which have already been described above.

The system first obtains a grate signal and stores it in the RAM. The way it does this is to transmit five 25 microsecond pulses (having a length in air of about 0.1 inch), each spaced apart about 2 milliseconds. If two signals are not received that are the same within 0.1 inch, then this first set of pulses is discarded and a new set of five pulses is immediately (in about two milliseconds) transmitted. If two signals are received and are within 0.1 inch, and if they are from a distance of from about 7 to 13 inches, then the system decides that it is the grate distance and stores it in the RAM.

The system then goes to the cup detection routine. The same set of pulses is transmitted and is received at maximum sensitivity. To determine that a cup is present, the system has to see 5 consecutive echo distances, each separated by 6 milliseconds, that correlate to within 0.2 inch. That is, 5 sets of pulses are transmitted with 6 milliseconds between each set. If at least two signals are received from the first set of 5 pulses that are within 0.1 inch, then that will be one value (or one echo distance). After receiving 5 of those in a row within 0.2 inch, the system knows that a cup lip (or something other than the grate) is present.

The system then goes to the next routine. In this routine the system looks for something greater than 0.1 inch above the grate and greater than 0.25 inch below the lip, that is, either the cup bottom or ice. If it finds this, it concludes that the something present is a cup (rather than just a hand, for example). When the ice or bottom is obtained, it is stored temporarily. The cup height is then calculated and the ice height is then calculated. It is then calculated whether or not the cup has too much ice. If it does not, the system goes to the FILL routine. This routine is somewhat complex.

In the FILL routine there are four filling periods. A first period or initial fill that is not monitored but which is set as a time function based on cup height. It will fill to about ⅓ cup under certain usual conditions. The system then switches automatically, without stopping the filling, to the second period in which the filling is monitored, and in which the filling is shut off when the liquid level rises to within 0.75 inch of the stored lip distance. The FILL routine then waits 5 seconds to allow foam to subside (if the control module is set for a foamy beverage). The monitoring continues waiting for the foam to quit moving and when two distances are received within 0.1 inch, then it calculates if the level is within 7/20 inch of the lip. If it is not, filling is resumed and monitored until the level is within 7/20 inch of the lip. If it is within 7/20 inch, filling does not resume. The "top off" routine is then repeated after another 5 second pause.

After the end of the FILL routine, the fill indicator light 92 is turned off, the solenoids are turned off, and the over-ice indicator light 94 turns off.

A second embodiment of the present invention will now be described with reference to FIGS. 27–46. An important difference between this embodiment and that described above with reference to FIGS. 1–26 is that this embodiment is designed so that two or more beverage dispensing valves having the ultrasonic control system of this embodiment can be located in close proximity to each other, such as by being adjacent valves on a dispenser, without interference therebetween. However, many other features of the two embodiments ar identical.

Figure 27:
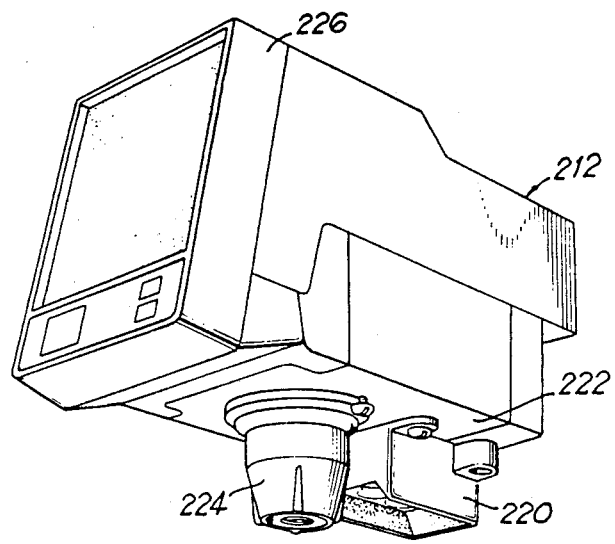
FIG. 27 is a perspective view of another embodiment of a valve assembly useful on the beverage dispenser of FIG. 1.

FIG. 27 shows a valve assembly 212, similar to valve assembly 12, that can be used as one or more of the valve assemblies on the dispenser 10 of FIG. 1. The automatic filling apparatus of this embodiment of the present invention includes a transducer assembly 220 located on the bottom surface 222 of the valve assembly 212 and behind the nozzle 224, and a control module 226 attached to the front of the valve assembly 212.

Figure 28:
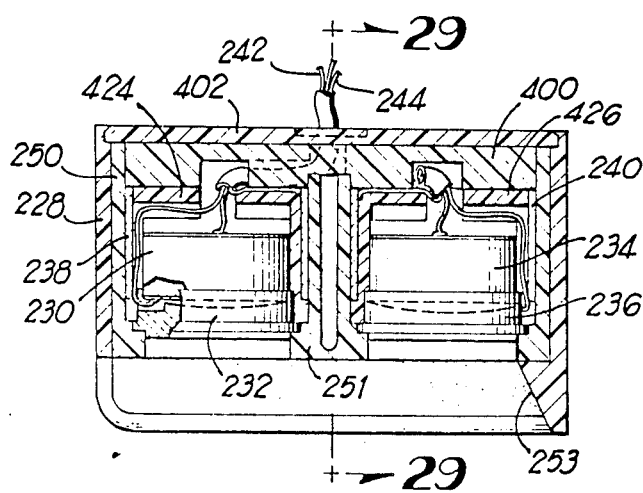
FIG. 28 is a cross-sectional side view of the transducer assembly shown in FIG. 27.
Figure 29:
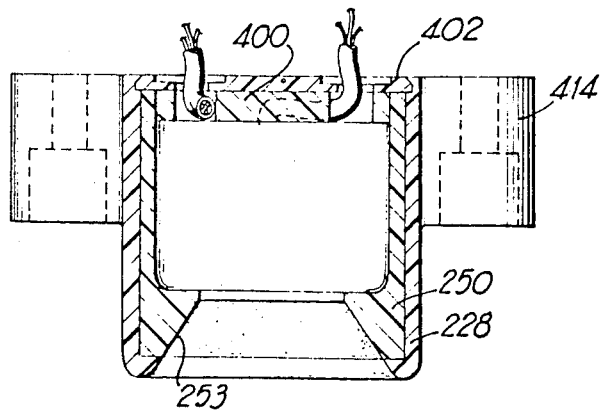
FIG. 29 is a cross-sectional end view of the transducer assembly of FIG. 28.
Figure 30:
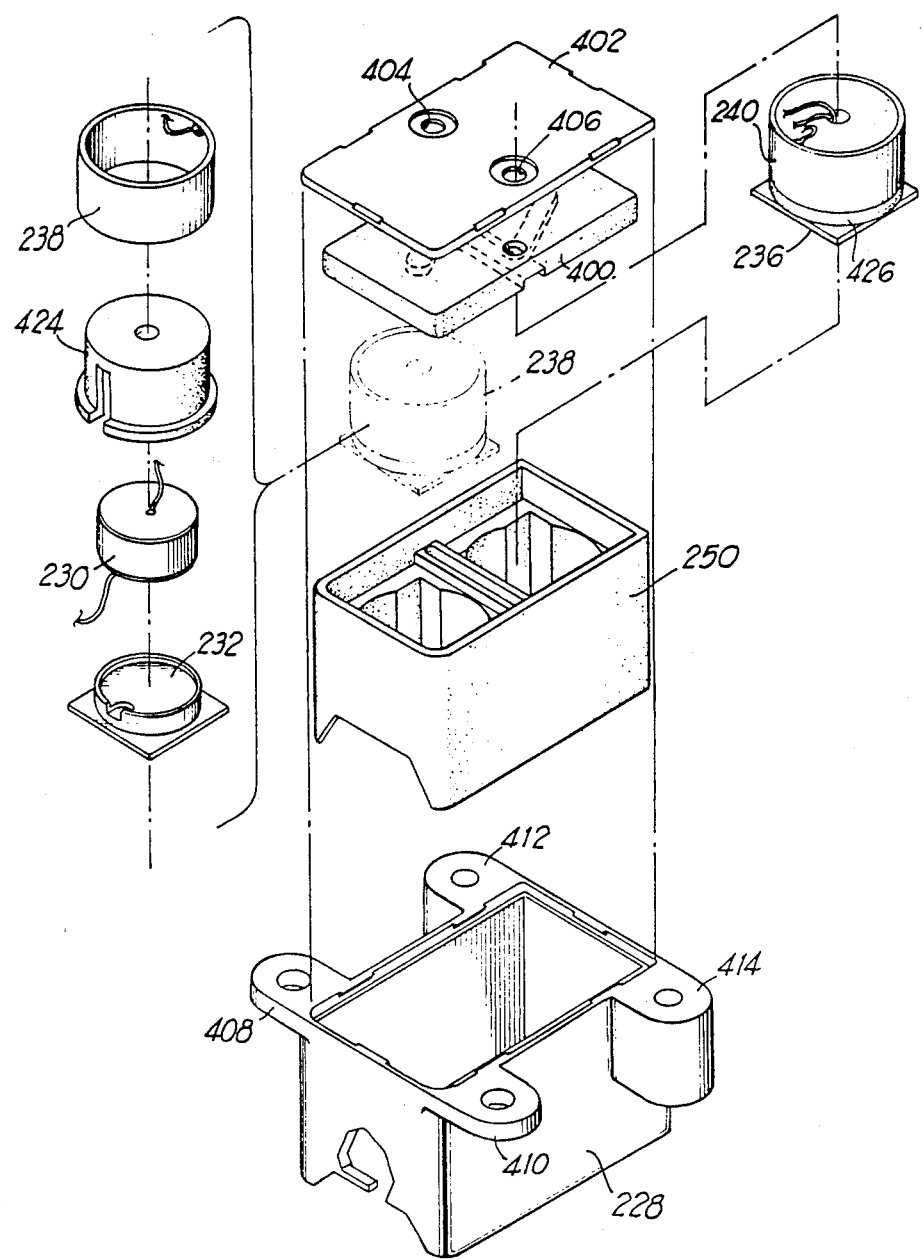
FIG. 30 is an exploded perspective view of the transducer assembly of FIG. 28.

The transducer assembly 220 is best shown in FIGS. 28-30 and includes a plastic housing 228 in which is contained a transmitter crystal 230 having a plastic lens 232, and a separate receiver crystal 234 having a plastic lens 236. The transmitter and receiver crystals are located inside of brass tubes 238 and 240, respectively.

A pair of shielded cables 242 and 244 each consist of a shield wire connected to a respective one of the brass tubes 238 and 240 and also a pair of wires connected to a respective one of the crystals at opposite locations thereon, as shown in FIG. 28. Each of the crystals has a metal plating on each of its upper and lower surfaces. The wire connections to the crystals are 28 gauge wire soldered directly to the crystal plating.

The cables 242 and 244 are about nine inches long and terminate in a single MTA connection (such as 48 in FIG. 3), for connection to the control module 226 substantially all of the space within the housing 228 is filled with urethane foam 250.

The transmitter crystal 230 and the receiver crystal 234 are preferable PZT-5a ceramic crystals (a generic trade designation for a particular crystal material), which are a combination of lead titanate and lead zirconate. Each of the crystals is attached to its respective lens preferably by using about ½ drop of glue such as that sold under the trademark Eastman 910. The plastic lens is preferably made of ABS or polycarbonate plastic.

The plastic housing 228 has a pair of flanges on each side thereof, each flange having a screw hole for attaching the transducer assembly 220 to the valve assembly 212.

The brass tubes 238 and 240 have the same function as described above with reference to brass tubes 38 and 40. As shown in FIGS. 28–30, the transducer assembly 220 includes the plastic housing 228, a urethane foam filler 250, a urethane foam lid 400, a plastic cover 402, and the transmitter and receiver subassemblies 420 and 422, respectively, slid into a pair of spaced-apart cylindrical cavities in the foam filler 250.

The transmitter subassembly 420 includes the transmitter crystal 230, the lens 232, a urethane foam thimble 424 and the brass tube 238. The receiver subassembly similarly includes the receiver crystal 234, the lens 236, a urethane foam thimble 426 and the brass tube 240.

The lenses 232 and 234 are shaped as shown in FIGS. 28 and 30 with a square flange and a circular lip to receive the crystal. The crystal is glued to the lens as described above. The crystal-lens unit is then pushed inside the thimble and the tube is pushed over the thimble. The lens has a recess for the wire connection to the lower face of the crystal and the thimbles have two grooves as shown in FIG. 28 for the two wires connected to the crystal. No groove is provided for the wire connected to the brass tube.

The housing 228 has a pair of thin flanges 408 and 410 and a pair of thick flanges 412 and 414 with screw holes for use in connecting the transducer assembly 220 to the dispensing valve 212. The thick flanges 412 and 414 are used to adjust the position of the housing 220 and thus, the location of the transmitted beam.

As shown in FIG. 28, the lenses 232 and 236 are recessed into the bottom of the foam filler 250 to provide a baffle 251 there between. Also, the lower sidewalls 253 of the filler 250 extend downwardly below the lenses 232 and 234. The baffle 251 helps prevent ultrasonic energy passing directly from the transmitter to the receiver. The sidewalls 253 help prevent ultrasonic energy from being transmitted sideways to an adjacent valve. The foam absorbs the ultrasonic energy.

The selection of the most desirable frequency to use is also the same as described above with reference to the first embodiment.

Regarding the beam shape, at 14 inches, the total maximum beam pattern needs to be less than 3 inches wide at the limits of detectability ($-40$ db) in the side to side direction and approximately 3 inches front to back with $-3$ db point in the front followed closely by the 0 db point and then tapering off to $-6$ db at the rear. The gain at a point near the front of the pattern (toward the nozzle) needs to be a maximum with the gain falling off smoothly by about 6 db as the pattern reaches the back point. The crystal pattern was chosen empirically as the one giving the best cup lip to ice (front) ratio with the crystals aligned from front to back between the nozzle 224 and the splash plate 25.

The resulting overall gain pattern at 12 inches had a spread sideways of 3.5 degrees, and a resulting spread front to rear of 12 degrees.

To achieve the desired beam pattern, it was necessary to lens the crystals. A 2 inch concave radius produced the 8 degrees to 3.5 degrees narrowing from side to side for both transmit and receiving crystals, a inch convex radius produced the 8° to 12° spreading from front to rear for the receiver crystal and a flat lens toward the front for $\frac{1}{2}$ the crystal followed by a 3 inch convex radius to the rear for the transmitter crystal which formed a fan-shaped beam pattern with an elongated footprint having a width of approximately $\frac{3}{4}$ inch at $-3$ db and having a length of about $2\frac{1}{2}$ inches with a bright spot about 1 inch in from the front with $-3$ db at the front and $-6$ db at the rear and 12 inches away from the transducer assembly 220. This beam-shape footprint has its long dimension extending front to back relative to the the dispenser.

Coupling from the crystals to the air was calculated in the same manner described above for the first embodiment.

One change in this second embodiment is that the lenses are inset into the bottom surface of the foam package.

Regarding the crystal shape and material, the transmitter crystal is preferably $\frac{1}{2}''$ OD$\times$0.200'' for a series resonance of 400 KHz. PZT-5a material was chosen for the crystals 230 and 234 as the best compromise in strength, efficiency, low mechanical Q, and ease of workability. The receiver crystal is preferably $\frac{1}{2}''$ OD$\times$0.190'' for a parallel resonance of 400 KHz, and is also made of PZT-5a material.

Regarding the electrical wiring, a twisted shielded pair of 28 gauge stranded wire is used and soldered directly to the plating on the crystal faces. The wire shielding is soldered to the brass tubes 238 and 240. The brass tubes are isolated from each other electrically. The black wire of the twisted pair is attached to the outside crystal face which is marked with a small dot.

Figure 31A:
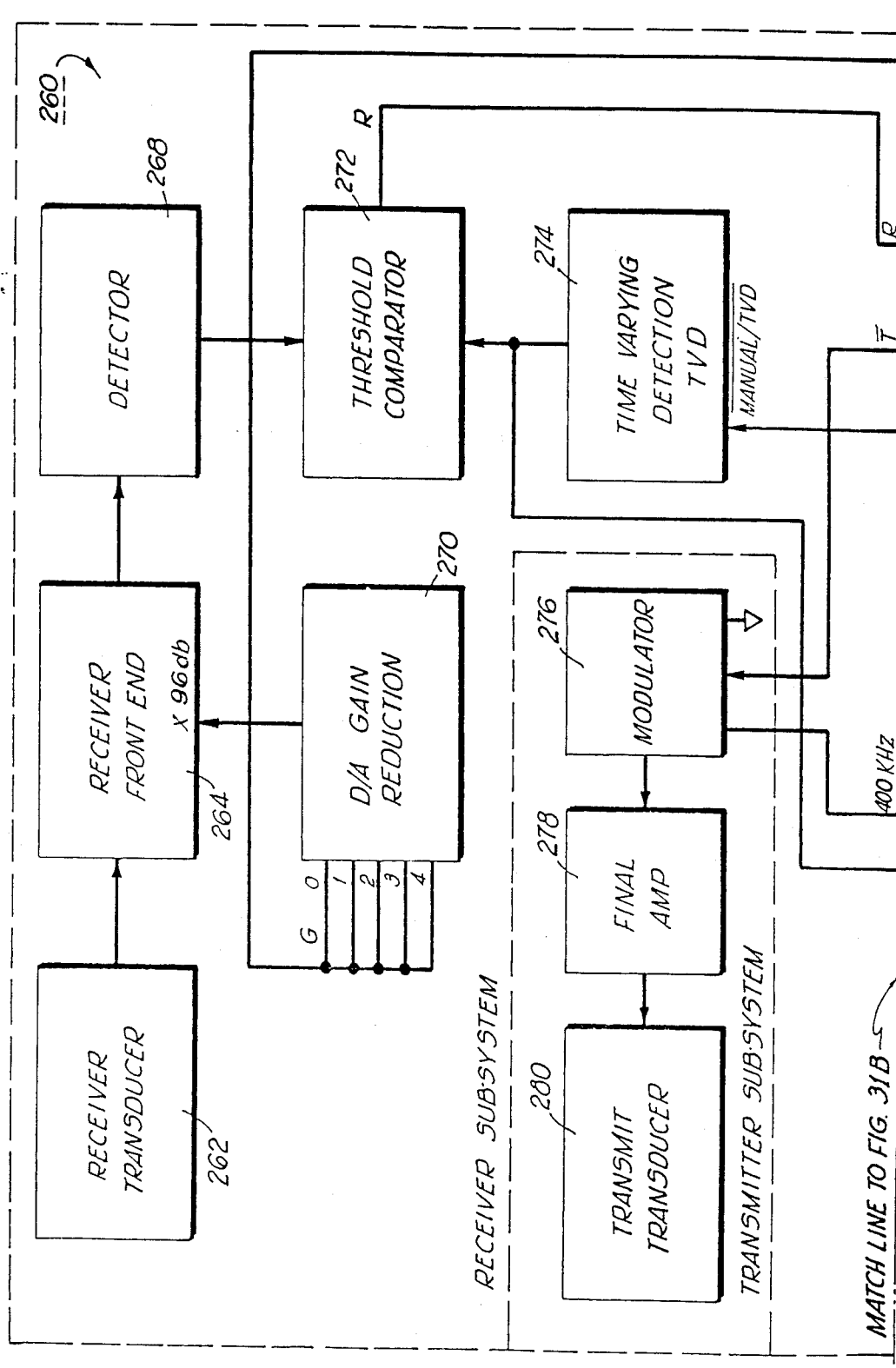
FIGS. 31A and 31B are a master block diagram of the automatic control system of the preferred embodiment of the present invention.
Figure 31B:
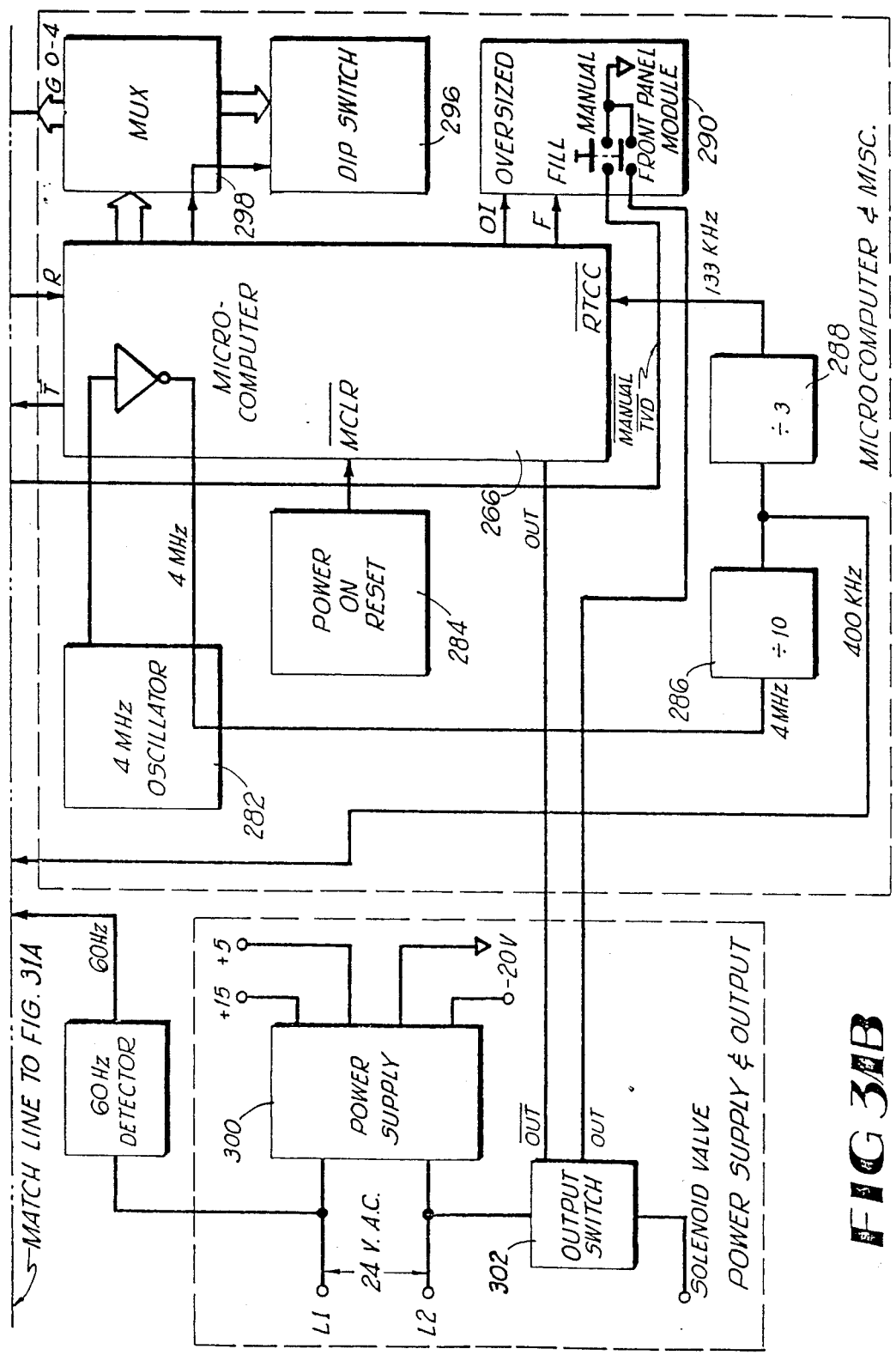
Figure 32:
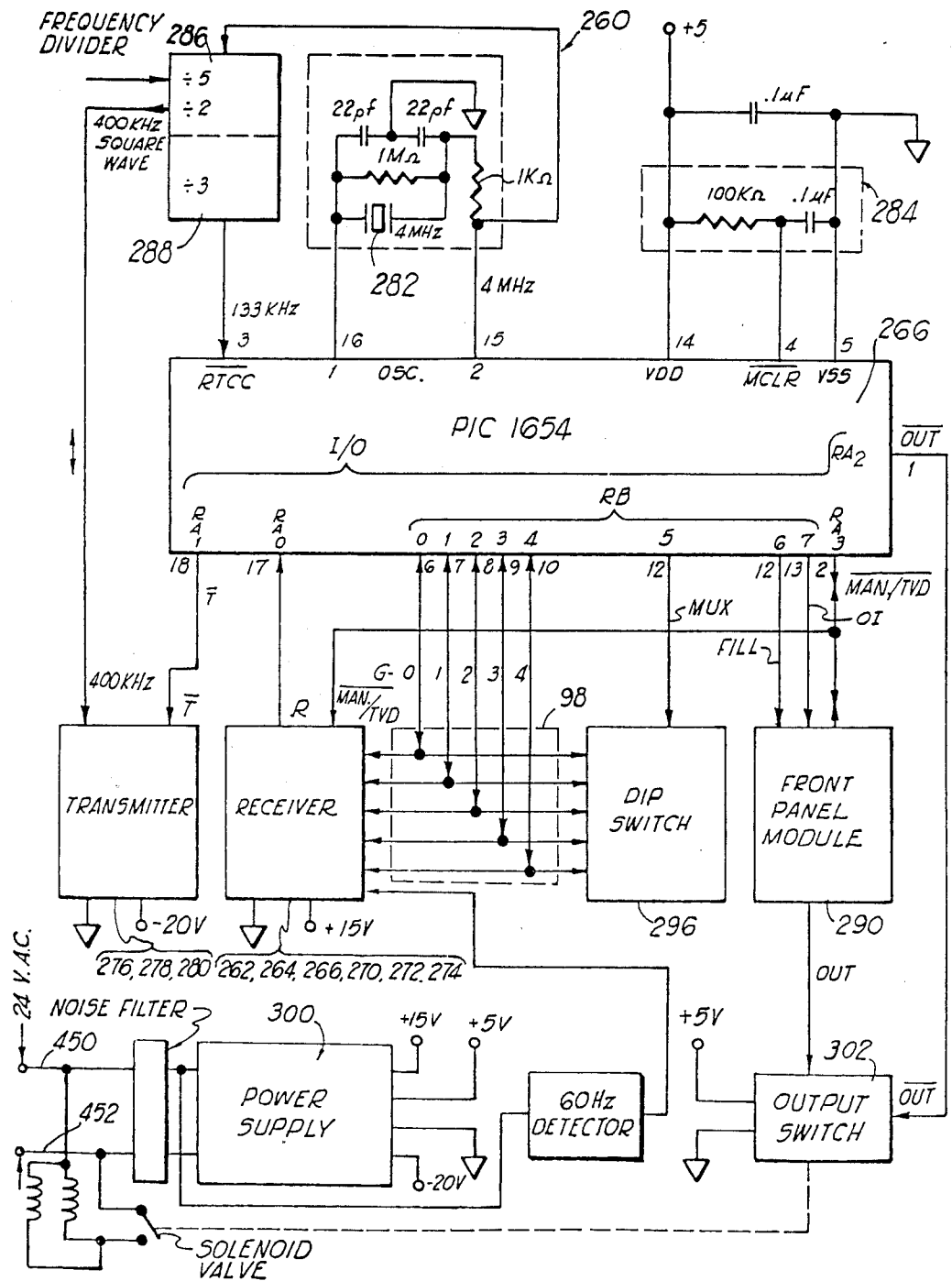
FIG. 32 is a microprocessor block diagram.
Figure 33:
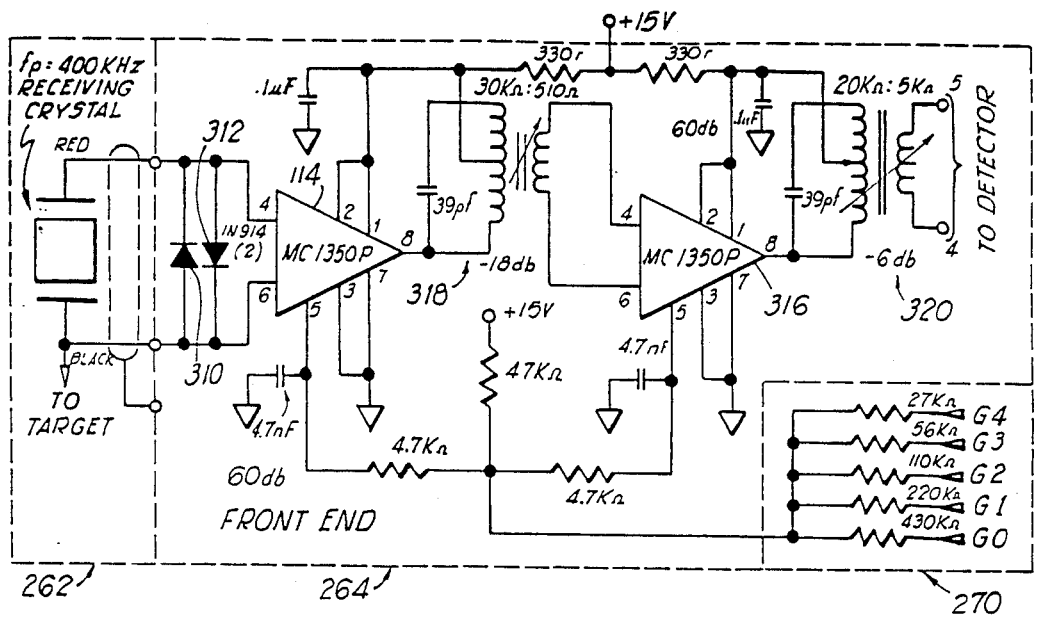
FIG. 33 is a schematic circuit diagram of part of the receiver subassembly including the receiver, the receiver front end, and the D/A gain reduction of FIG. 31.
Figure 34:
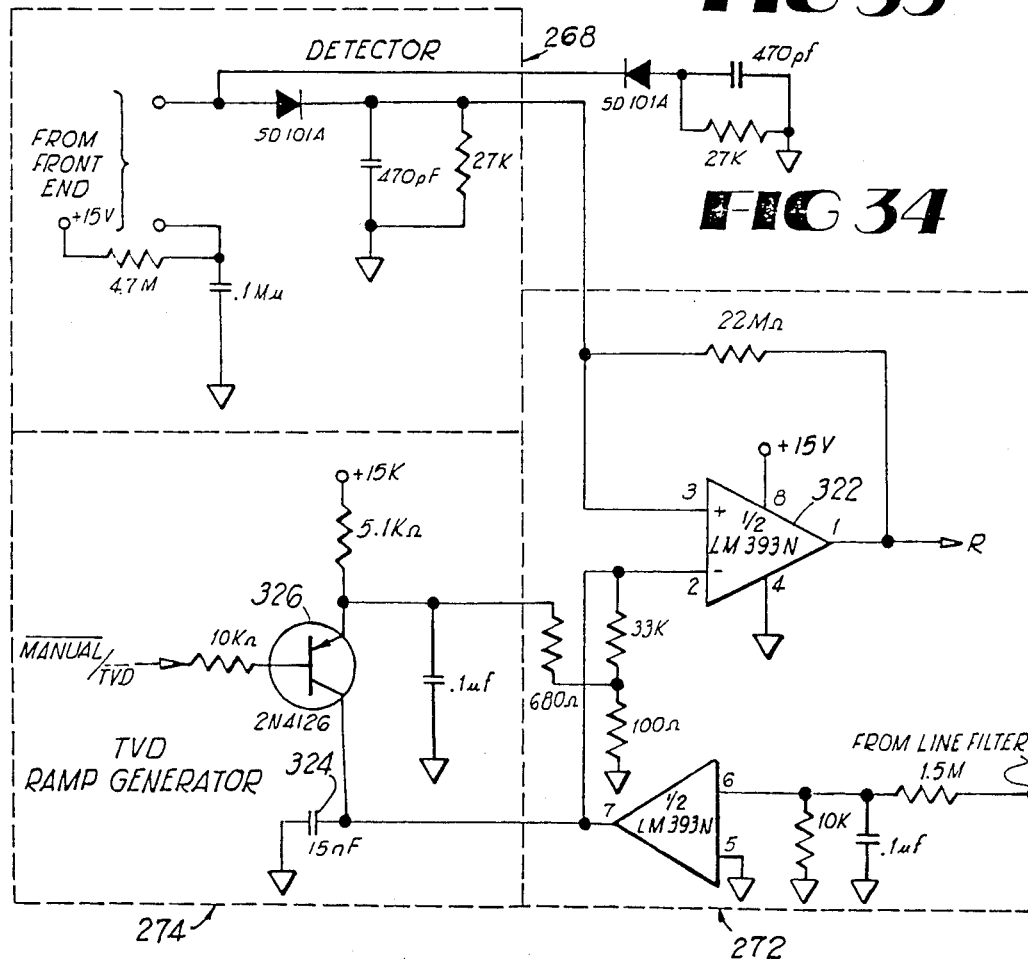
FIG. 34 is a schematic circuit diagram of another part of the receiver subassembly including the detector threshold comparator, the time varying detection generator, and the 60 Hz detector of FIG. 31.
Figure 35:
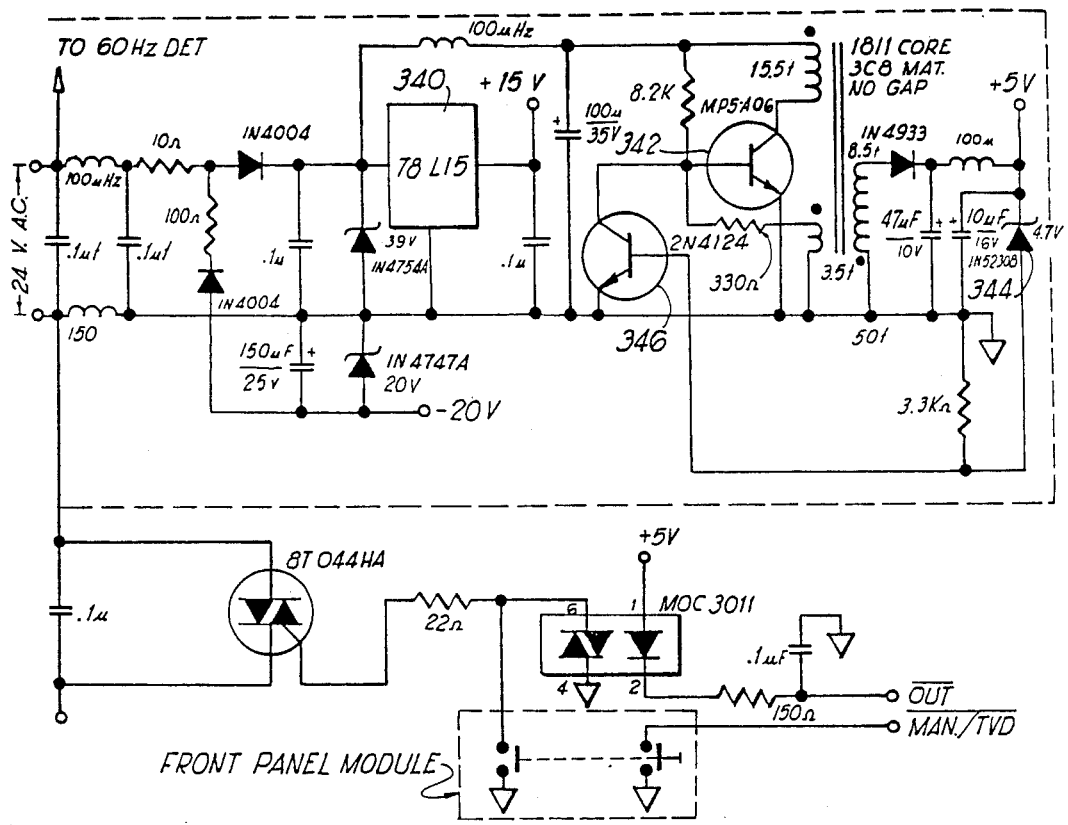
FIG. 35 is a schematic circuit diagram of the power supply and output switch of FIG. 31.
Figure 36:
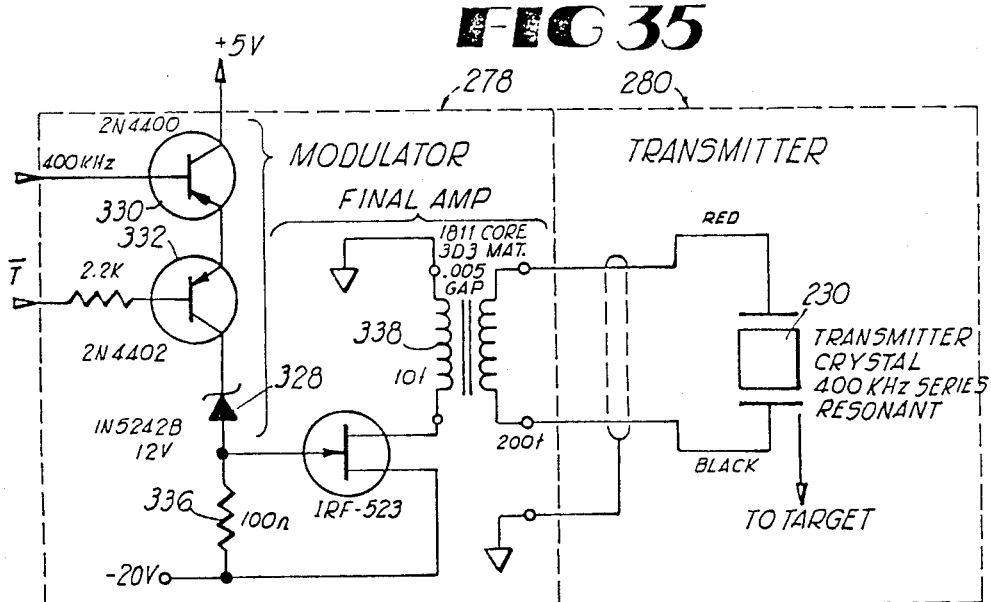
FIG. 36 is a schematic circuit diagram of the transmitter subsystem of FIG. 31.
Figure 40A:
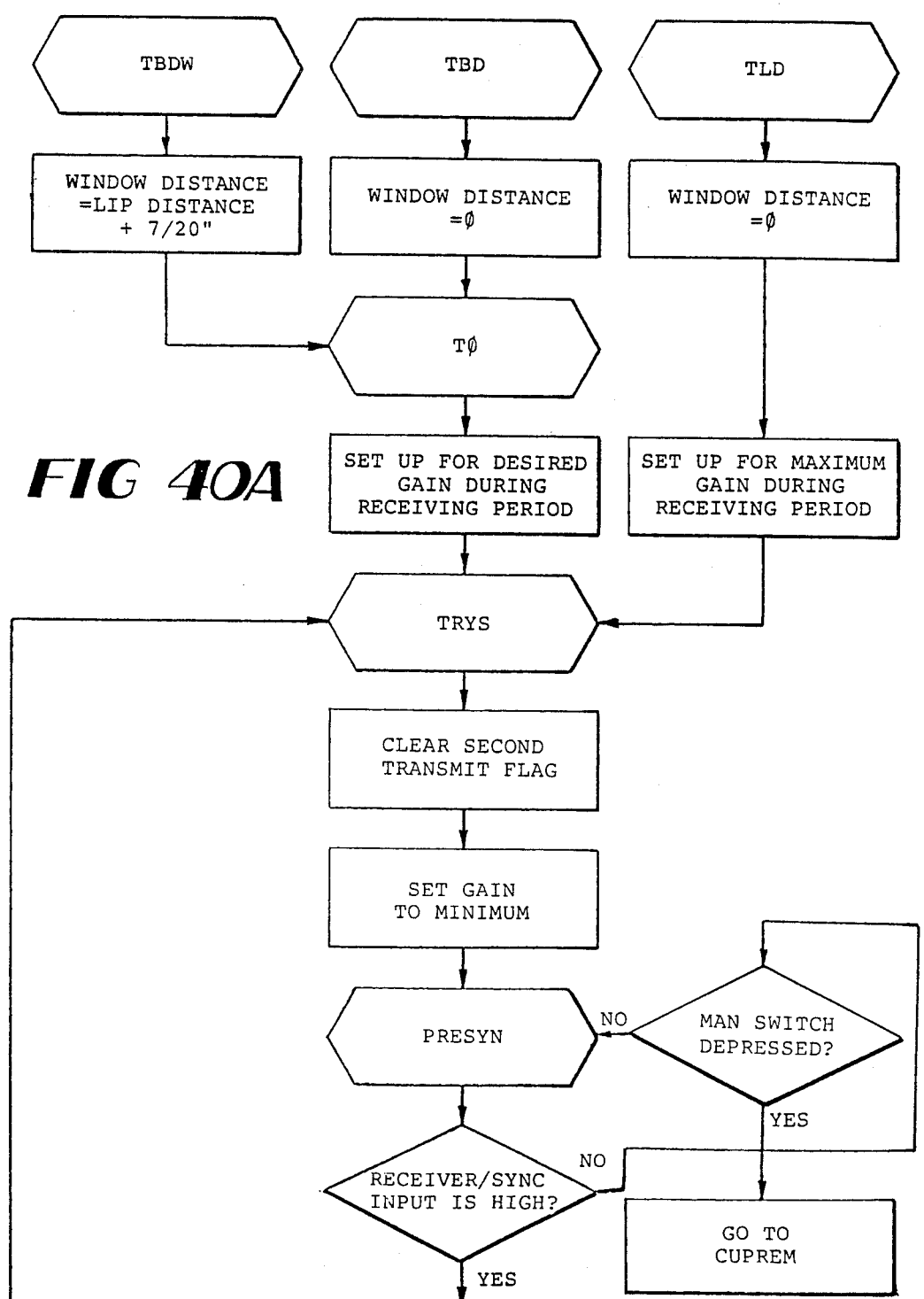
FIGS. 40-46 are flow charts illustrating the main routine and the subroutines of the software for operating the microcomputer in the block diagram of FIG. 31.
Figure 40B:
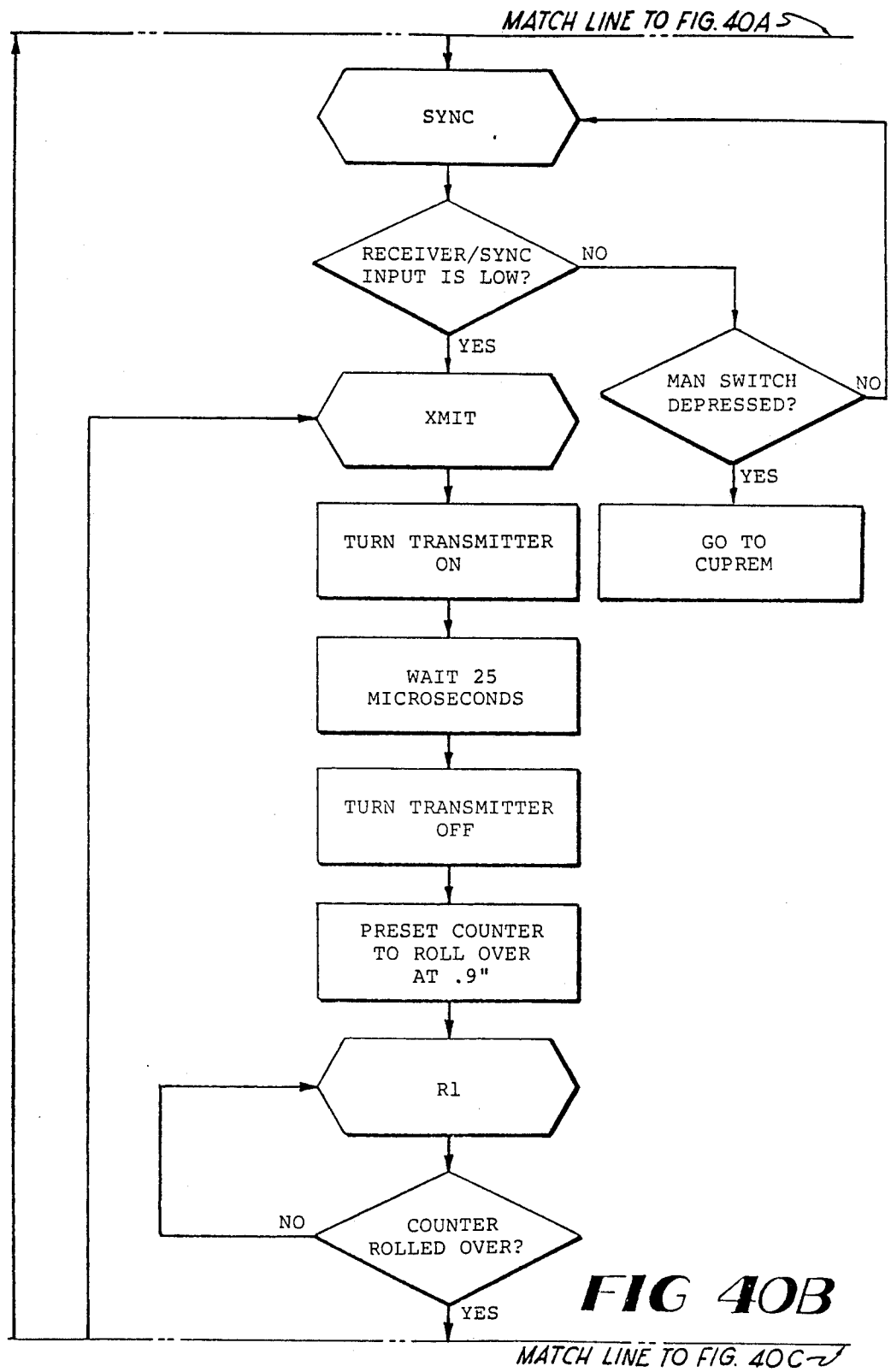
Figure 40C:
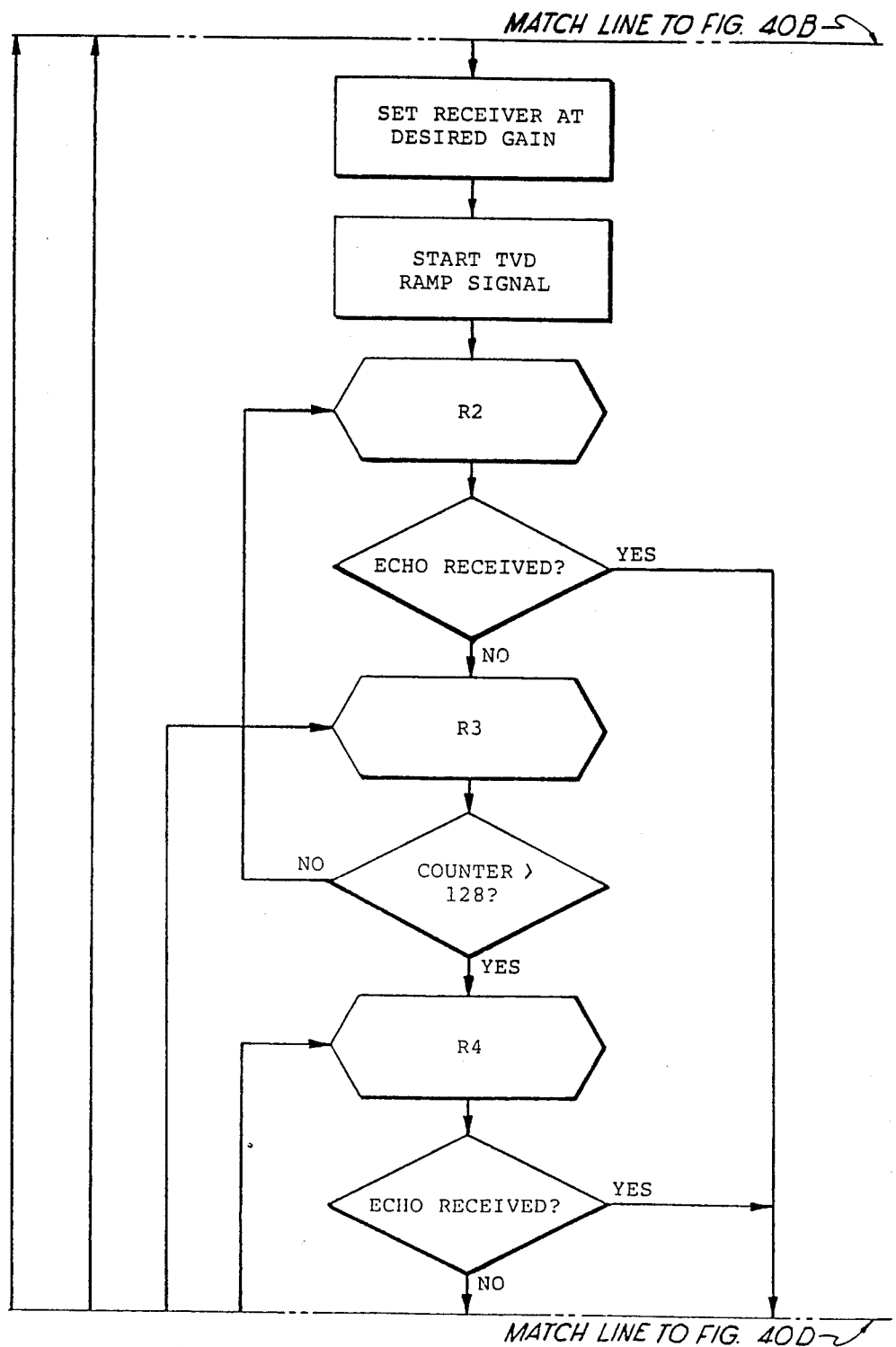
Figure 40D:
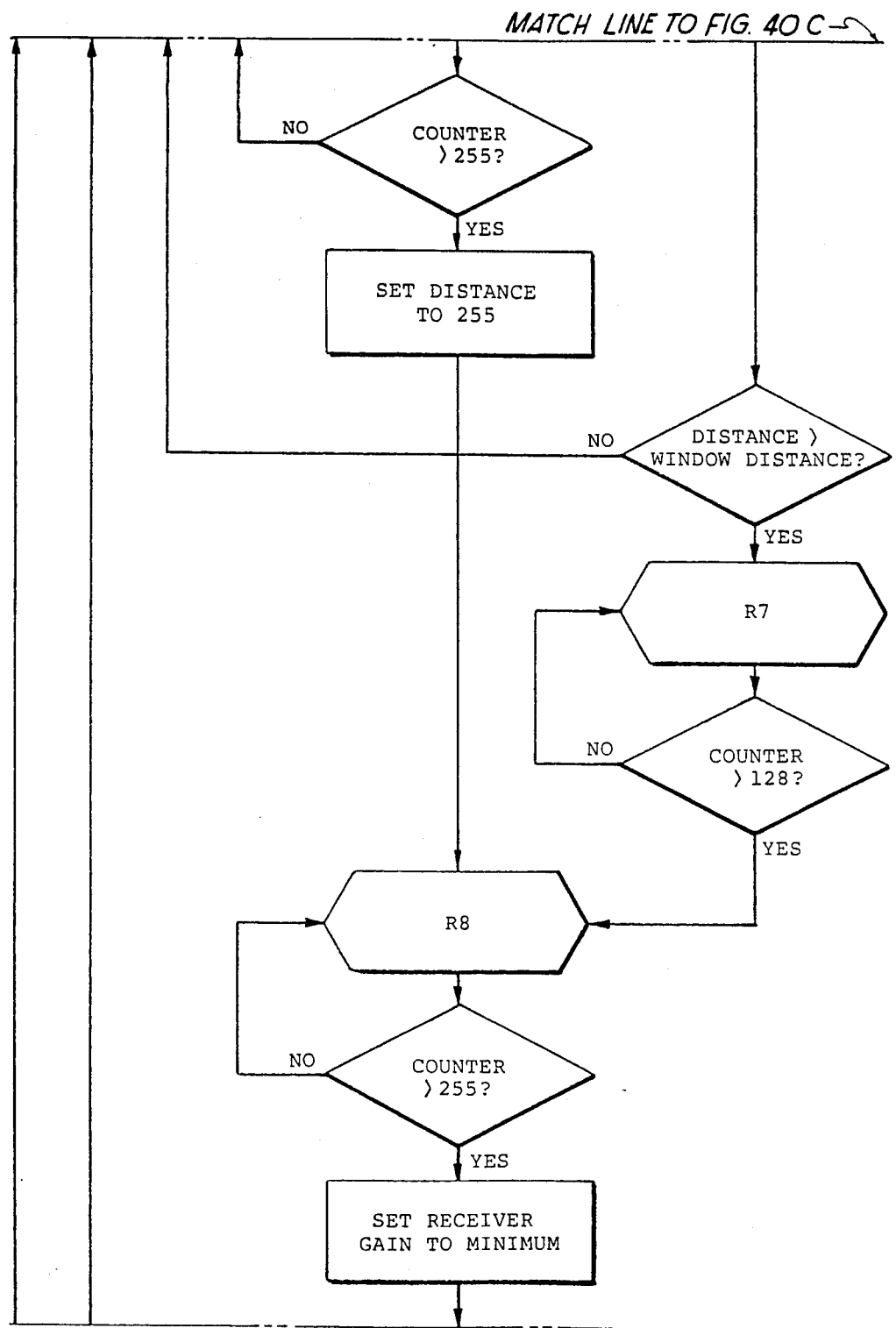
Figure 40E:
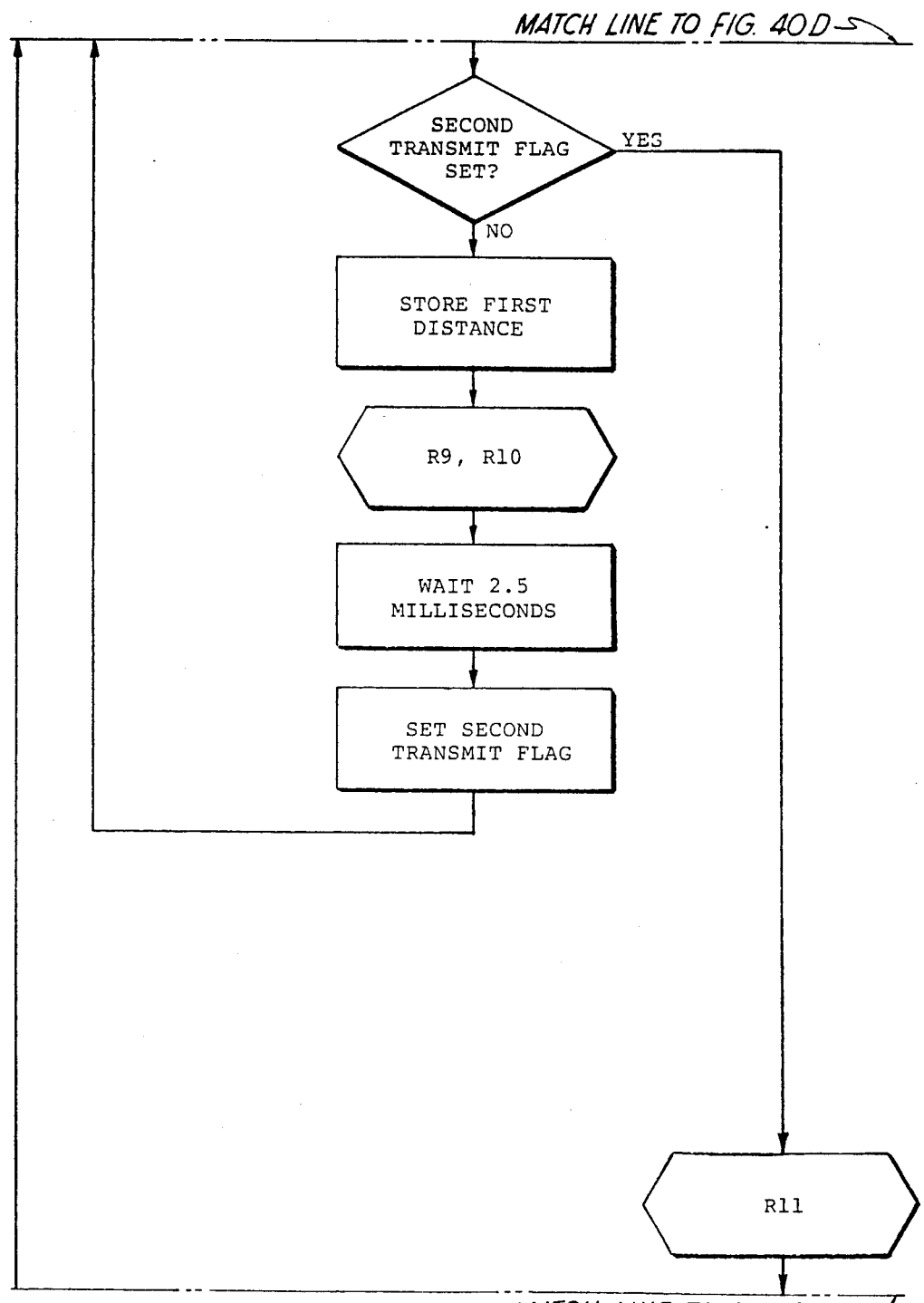
Figures 40F, 41, 42:
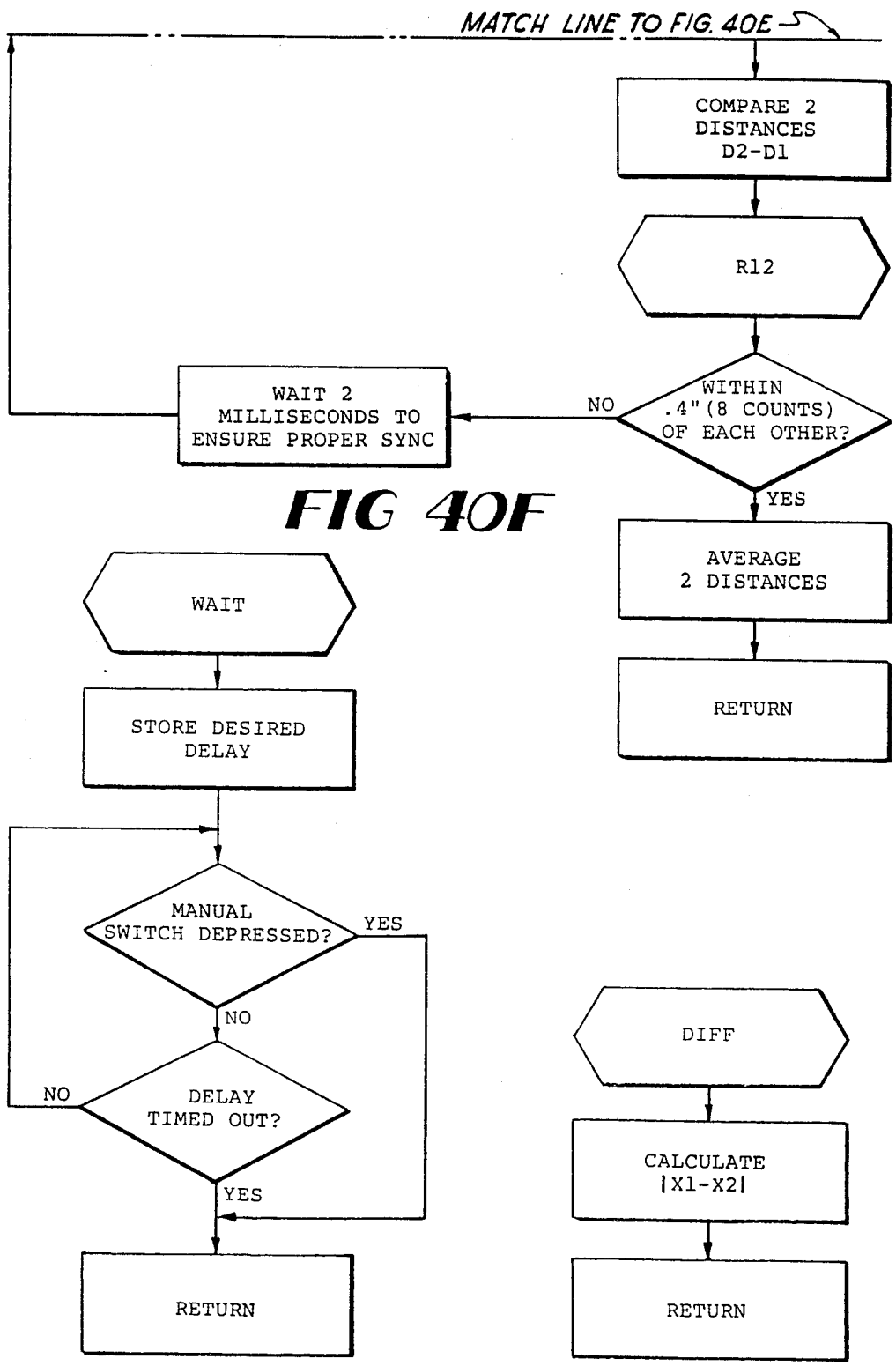
Figure 43A:
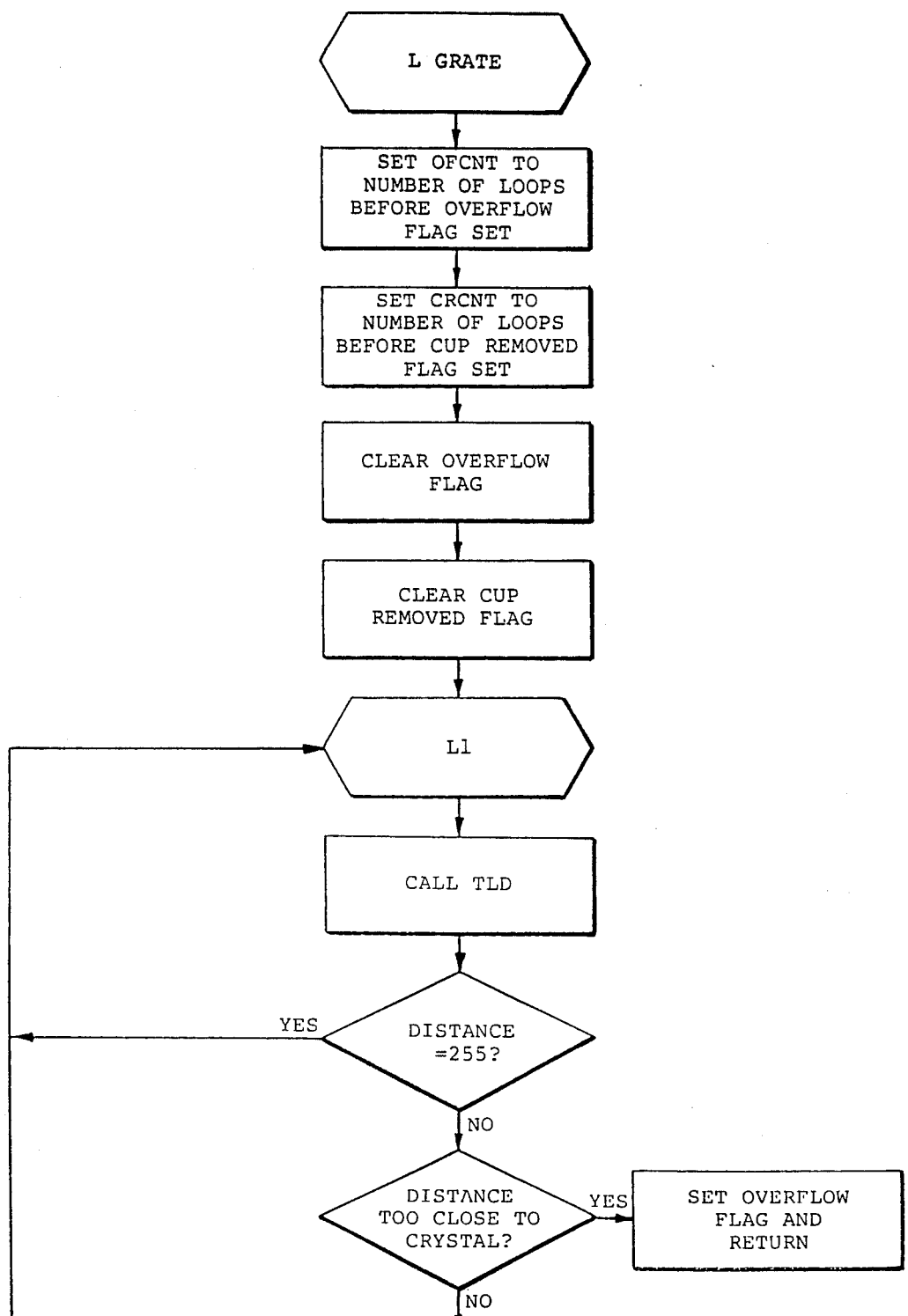
Figure 43B:
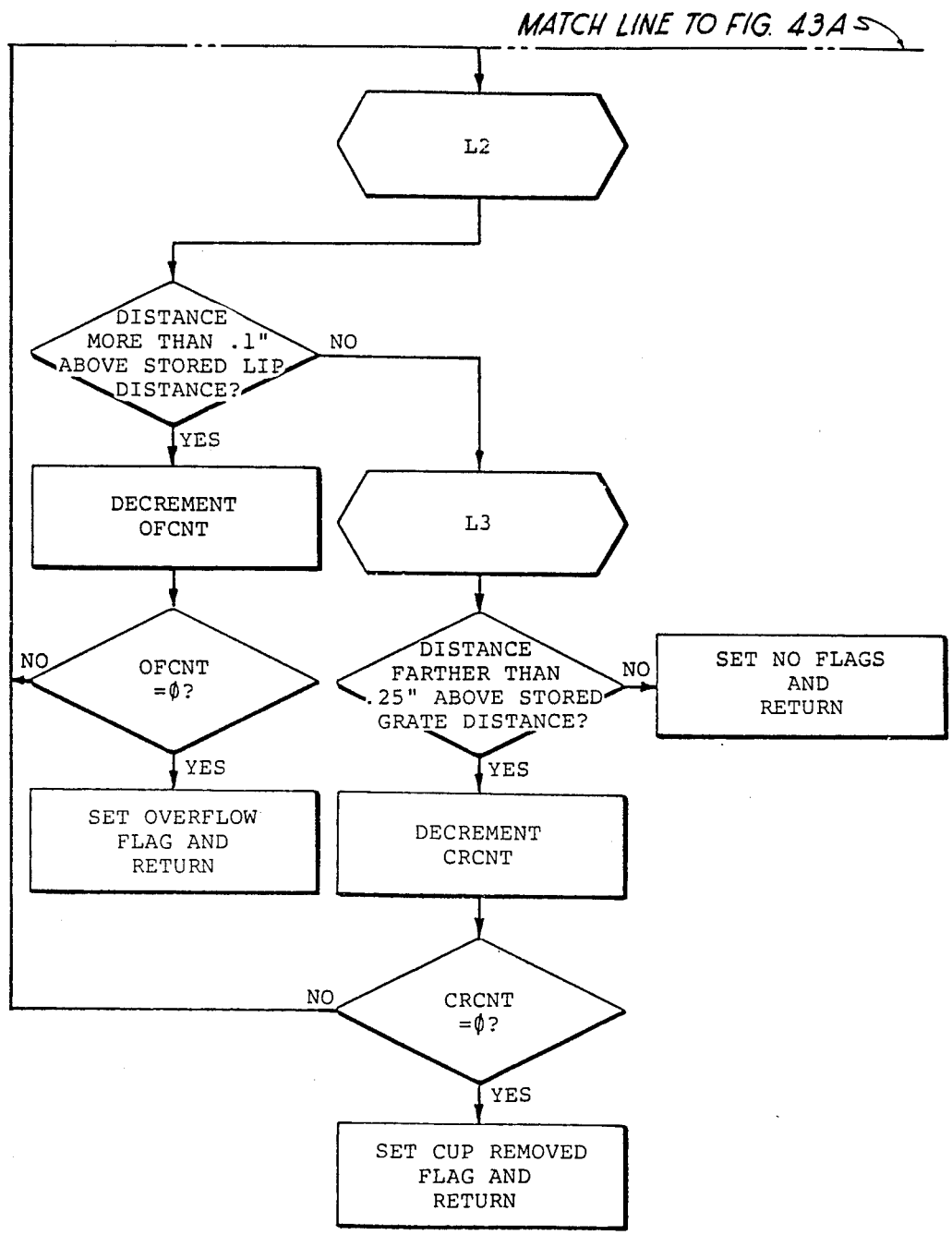
Figure 44A:
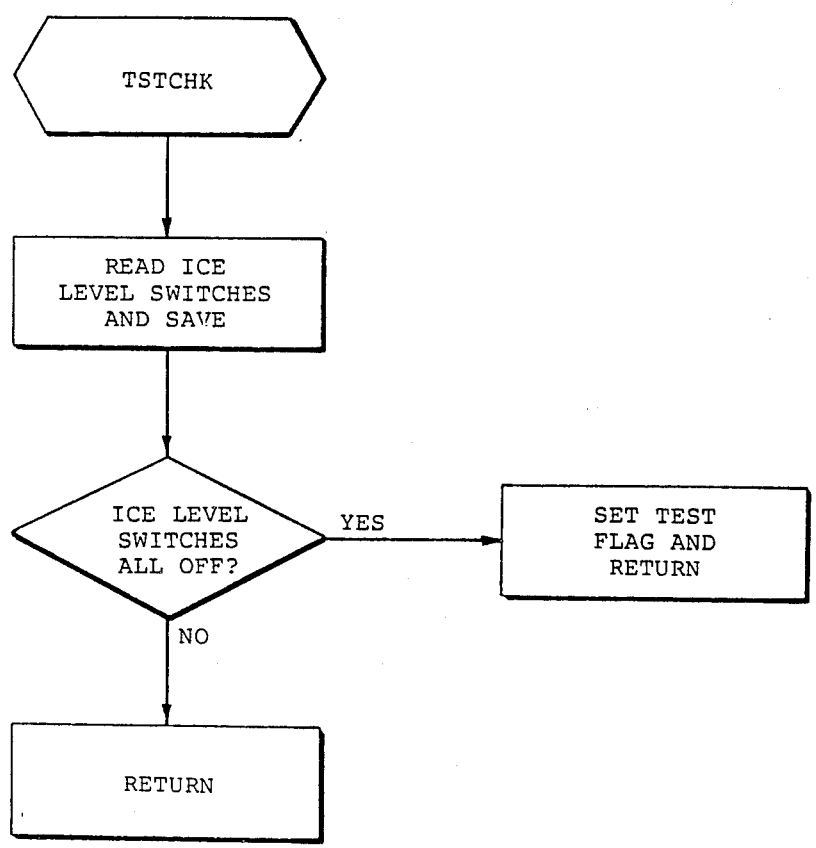
Figure 44B:
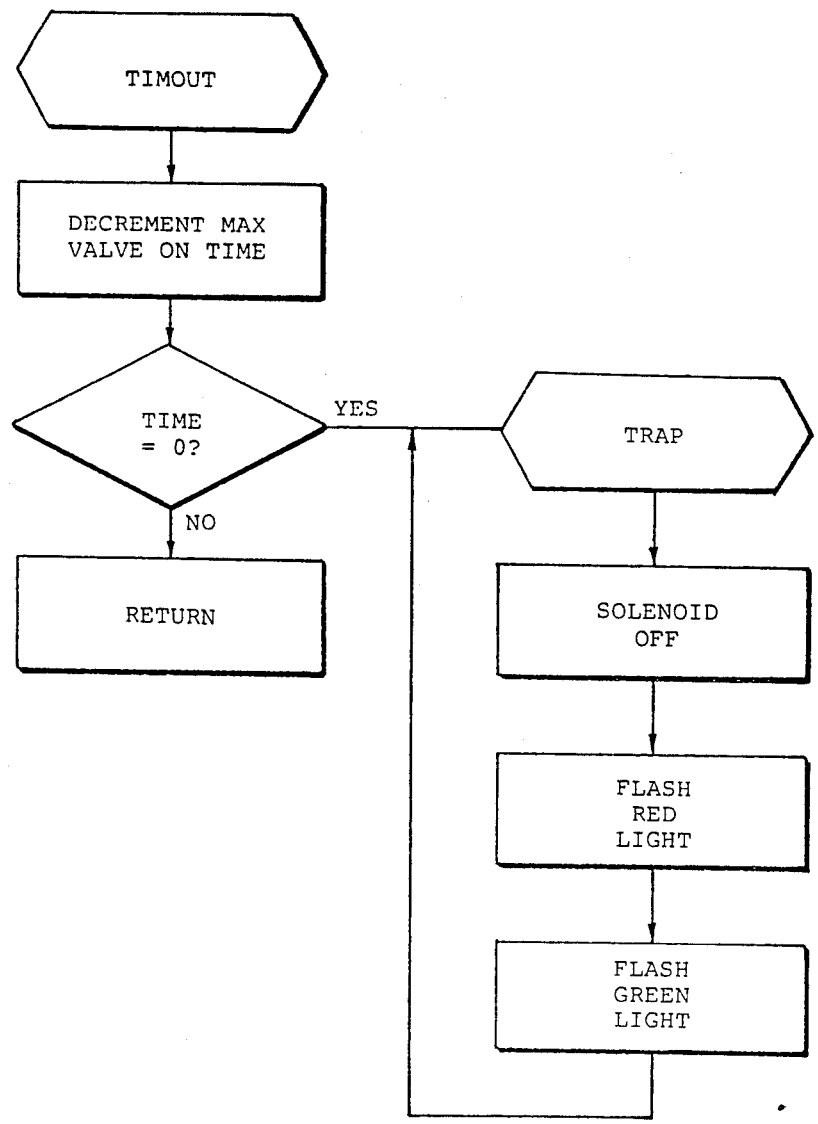

The control module 226 houses the control circuit board to which the crystals are connected by the cables 242 and 244 and the connector 248. FIGS. 31A and 31B together provide a master block diagram of the control circuit 260. The control circuit will now be described with reference to FIGS. 31-39.

The receiver transducer 262 (FIGS. 31, 32, and 33) is a 400 Khz, $\frac{1}{2}$ inch diameter parallel resonant piezo-electric crystal coupled to the air by means of a plastic lens shaped to receive the beam pattern. The transducer assembly 220 incorporates a brass tube 240 that is $\frac{3}{8}$ inch in diameter and is used for electrical isolation. The crystal is mounted such that it is centered in the tube with the lens 236 exposed at one end of the tube. The polyurethane foam provides for acoustic isolation.

The receiver section 264 (FIGS. 31, 32 and 33) has a total gain of 96 db and is comprised of two protective diodes 310 and 312 and two MC1350P IF amplifiers 314 and 316 that are interconnected through tuned transformer 318 with another tuned transformer 320 to interconnect the second amplifier 316 to the detector 268. These amplifiers 314 and 316 have provisions for gain control from Pin 5 and are used in this application by the microcomputer 266.

The detector circuit 268 (FIGS. 31, 32 and 33) changes the 400 Khz from the receiver 264 to a DC Analog signal. This detector is special in that it can not only detect the envelope of the pulse but since it is a DC coupled detector, it has no offset shift due to pulse width variations. By having a balanced detector system, the temperature drift is very low.

The receiver gain reduction circuit 270 (FIGS. 31, 32, and 33) is comprised for five resistors that form a binary weighted current sinking "D to A" converter that is driven by the microcomputer 266, which allows for thirty-two stages of gain level control.

The threshold comparator 272 (FIGS. 31, 32, and 33) is comprised of an LM393N comparator 322 and is used in conjunction with the time varying detection to convert the analog receiver signal to a digital signal which is then fed to the microcomputer 266.

The time varying detection generator 274 (FIGS. 31, 32 and 34) uses the manual/TVD signal from the microcomputer 266 and charges a 15 Nanofarad capacitor 324 to two volts, which sets the peak level of the time varying detector wave form. This circuit is compromised of a 2N4126 switching transistor 326 and the power supply to support that circuit. 60 Hz detection is accomplished in the 60 Hz detector shown in FIGS. 31, 32 and 34. The incoming 60 Hz, 24 VAC power is sensed, after filtering, by $\frac{1}{2}$ of the comparator LM393N 322 and the output shunts the TVD signal to ground which, because the detector 268 signal is biased above ground, forces the detector comparator output high for $\frac{1}{2}$ of the 60 Hz wave form. The microcomputer 266 senses this and uses the falling edge of the 60 Hz signal from the detector comparator to start its sequences and is thereby phase locked to the 60 Hz $-24$ VAC power system. Adjacent valve assemblies are separated in time by reversing their 24 VAC wires 450 and 452 (see FIG. 32) so that adjacent units synchronize to different cycles of the 60 Hz power supply and thereby do not interfere with each other. Alternatively, a switch can be provided having two positions labeled "A" and "B" to designate the two possible orientations of the wires 450 and 452. Thus, if one valve assembly has an "A" position, each immediately adjacent valve assembly must have the switch on the "B" position. Units spaced more than one valve assembly apart are far enough apart not to interfere with each other.

The modulator 276 (FIGS. 31, 32, and 36) is comprised of a 12 volt Zener diode 328 and two transistors 330 and 332 that perform an (Anding) function for the transmitter gate signal (T) and the 400 KHz signal from the oscillator. This (Anded) signal is then level shifted through the 12 volt Zener diode 328 and the 2N4402 transistor 332 to the gate of the final amplifier 278.

The final amplifier 278 (FIGS. 31, 32, and 36) is comprised of a IRF-523 MOS-FET 334, a resistor 336 and a transformer 338. The resistor discharges the gatesource capacitor of the MOS-FET 334. The MOS-FET 334 switches the output transformer 338 to the minus 20 volt supply in response to the gate drive signal. The transformer 338 steps the voltage up to the transmitting crystal 230 to approximately 2000 volts.

The transmit transducer 280 (FIGS. 31, 32, and 36) is comprised of 400 KHz ½ inch diameter series resonant piezo-electric crystal 30 made of PZT-5A material much the same as the receiver crystal with the exception of the thickness. The crystal 230 is coupled to the air by means of a plastic lens 232 which is also shaped to form the beam pattern. The assembly of the transmit transducer 280 is exactly the same as for the receiver as described above.

The microcomputer 266 (FIGS. 31 and 32) is a General Instruments Pic-1654 and contains the intelligence and control functions of the entire system. It communicates to the rest of the system through twelve I/O pins. It also contains the oscillator circuit, the master clear circuit, and the real time clock counter input.

The crystal 282 (FIGS. 31 and 32) and components of the 4 MHz crystal comprise passive components that form the feedback network for the oscillator in the Pic-1654.

The power-on reset circuit 284 (FIGS. 31 and 32) forms a 10 millisecond reset pulse to the microcomputer 266 at POWER-ON that allows the 4 MHz oscillator crystal 282 to start and the microcomputer 266 to become initialized.

A divide by ten counter 286 (FIGS. 31, 32, and 37) converts the 4 MHz computer clock to a 400 KHz square wave signal to operate the transmitter.

The divide by three counter 288 (FIGS. 31, 32 and 37) converts the 400 KHz signal to a 333 KHz signal that is applied to the microcomputer 266 as the real time clock counter input. Number thirteen and number fourteen are encompassed within the same IC (74HC390) divider chip which has a divide by ten and a divide by three circuit.

The front panel module 290 (FIGS. 31, 32, and 39) consists of two LED indicators 292 and 294. One is an "Over-Ice/Cup Remove" (FIGS. 31, 32, and 39) red indicator 292 and the other is a green "Fill" LED 294, indicating that the cup can be filled or is being filled. This indicator 294 remains "on" steady when a cup is okay until filling ends. In the event that there is too much ice in the cup, the Over-Ice/Cup Remove red indicator will light and stay lit until the cup is removed. If the cup is not recognized as a cup, due to mispositioning the green indicator light 294 will flash on and off.

There is a programming dip switch 296 (FIGS. 31, 32 and 38A) comprising five individual switches accessible by removing a cover (not shown) on the lower rear surface of the control module 226. One switch is used to select between a normal flow or a fast flow valve assembly, depending upon which type of valve assembly the automatic control system is being attached to. Another switch is used for selecting a foamy or flat product such as water. The other three switches are used for selecting ice level or test position. The test position is used for alignment of the receiver during manufacturing and has no field use. The binary output of the three ice level switches allows for seven ice level selections from ⅛ cup to ⅞ths cup, as illustrated in FIG. 38B.

The multiplexer circuit 298 (FIGS. 31 and 32) allows the microcomputer 266 to read either the dip switches or to set the gain of the receiver as necessary. It is comprised of five signal diodes.

The power supply 300 (FIGS. 31, 32, and 35) uses 24 volts AC from the 24 VAC transformer (not shown) in the dispenser 10. This 24 VAC is filtered to remove any high frequency noise that might interfere with the system operation. The present control system consumes less than 2 volt-amps at 24 volts AC. The 24 Volts AC is rectified and filtered to form a minus 20 volt DC supply and a plus 25 volt DC supply. The minus 20 volt supply is regulated with a Zener diode and supplies power to the transmitter. The plus 25 volt supply is unregulated but has a 39 volt Zener diode used as surge protection. The 25 volt DC supply is regulated down to 15 volts for the receiver subsystem by a 78L15 three terminal regulator 340. An MPS-A06 transistor 142 is used as a fly-back oscillator to provide the plus five volts needed to operate the computer circuitry. The 4.3 volt Zener diode 344 connected between the plus five volt supply and the base of a 2N4124 transistor 346 serve to regulate the fly-back oscillator.

The output switch 304 (FIGS. 31, 32, and 35) for the two solenoids of the valve assembly 212 is operated from either the microcomputer 266 or the manual push button 302 on the front of the control module 226. The resistor, opto-coupler network couples the microcomputer 266 to the Triac 349 which in turn energizes the valve solenoids in the valve 212 when either the microprocessor 266 or the manual push button 302 so requires.

The software will now be described with reference to FIGS. 40 through 46.

The software includes 4 major routines which are labeled Initialization Routine (INIT), Cup Detection (CUPDET), Fill Routine (FILL), a nd Cup Removal Routine (CUPREM).

The software also includes six subroutines that are defined as time delay (WAIT), absolute value of the difference of two numbers (DIFF), Grate/Overflow detector (LGRATE), Transmit/Receive, check for test mode (TSTCHK), and check for maximum value on time (TIMOUT).

The Transmitter/Receiver subroutine obtains a distance data by allowing the transmitter to operate for a period of 25 microseconds (10 cycles at 400 kHz which occupies 0.1" air space) and then monitoring the receiver output for reflections. Two Transmit/Receive periods are contained in the time period of a single half cycle of the sinusoidal line input voltage. The synchronization permits transmission only during the positive half cycle which allows two valves to operate side by side without interference by reversing the line input wires on adjacent valves. Three different entry points to the subroutine select receiver options: TBD (Transmit Bottom Detector), TBDW (Transmit Bottom Detector with Window) and TLD (Transmit Lip Detector).

The receiver has 32 steps of gain controlled by the software. The gain is set to minimum from the start of transmit to approximately 0.9" target distance time (180 microseconds). At that time, the gain is set equal to the gain variable set up in the entry point routines. For TLD, the gain is always set to maximum. For TBD and TBDW, the gain is determined by the calling routine. In TBD and TLD, the distance of the first echo detected is captured for processing. In TBDW, a lip masking window is enabled which ignores any echoes closer than the lip distance +0.35". This allows a higher gain to be used to look at liquid level rising inside the cup. Under all entry points, 2 transmissions, each separated by two milliseconds of receive time and two milliseconds of waiting for all reflections to cease, are made and the received distances stored in RAM. The processing algorithm accepts the distances if they correlate within a 0.4" and returns with the mean value as the correct distance. If the two distances do not correlate, then the routine waits on the synchronization signal and takes two new samples to correlate.

WAIT is a programmable delay subroutine that returns to the calling routine immediately if the manual push button is pressed. It has a minimum delay of 3.5 msec, and a maximum delay of 0.9 seconds.

DIFF is a subroutine that calculates the absolute value of the difference of two numbers.

LGRATE is Grate/Overflow detector subroutine used during the FILL routine to determine whether a cup has been removed or if foam or liquid has risen above the lip. The subroutine uses TLD to detect with maximum gain and no window. If TLD returns with a distance of exactly 13.7", the distance is rejected and TLD is called again. 13.7" is the maximum distance allowed by the receiver software and indicates no reflection was detected. If TLD returns with a distance less than 0.2541, the overflow flag is immediately set. If TLD returns with a distance more than 0.1" closer than the stored Lip Distance for three consecutive calls to TLD, the overflow flag is set. If TLD returns a distance farther than 0.25" above the stored GRATE value for twelve consecutive calls to TLD, the cup removed flag is set. If TLD at any time returns a distance that does not meet any conditions above, the subroutine ends with no flags set.

TSTCHK (FIG. 44A) is a subroutine that reads the five position DIP (Dual Inline Package) switch. The switch positions are stored in the location in RAM labeled SWITCH. If the switches in positions 1, 2 and 3 are all off, the Test flag is set.

TIMOUT (FIG. 44B) is used whenever the solenoid valve is turned on. The subroutine decrements the "Valve on Time" register and checks to see if the value of the Register is Zero. If it is greater than zero the subroutine ends. If the value of the register is zero, the routine enters a trap loop from which there is no exit except through a hardware reset. The trap loop turns the solenoid off and alternately flashes the red and green indicators.

Figure 45B:
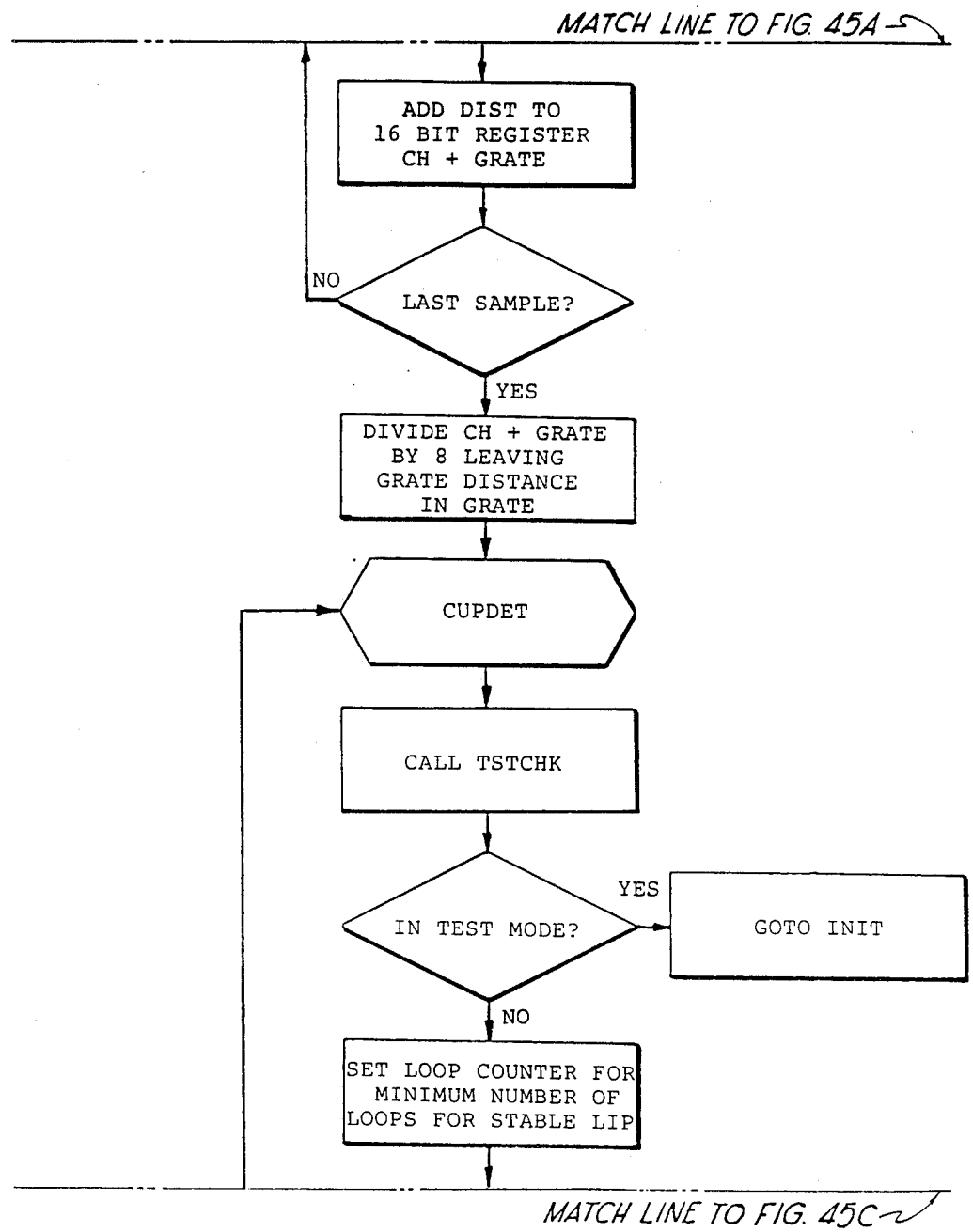
Figure 45C:
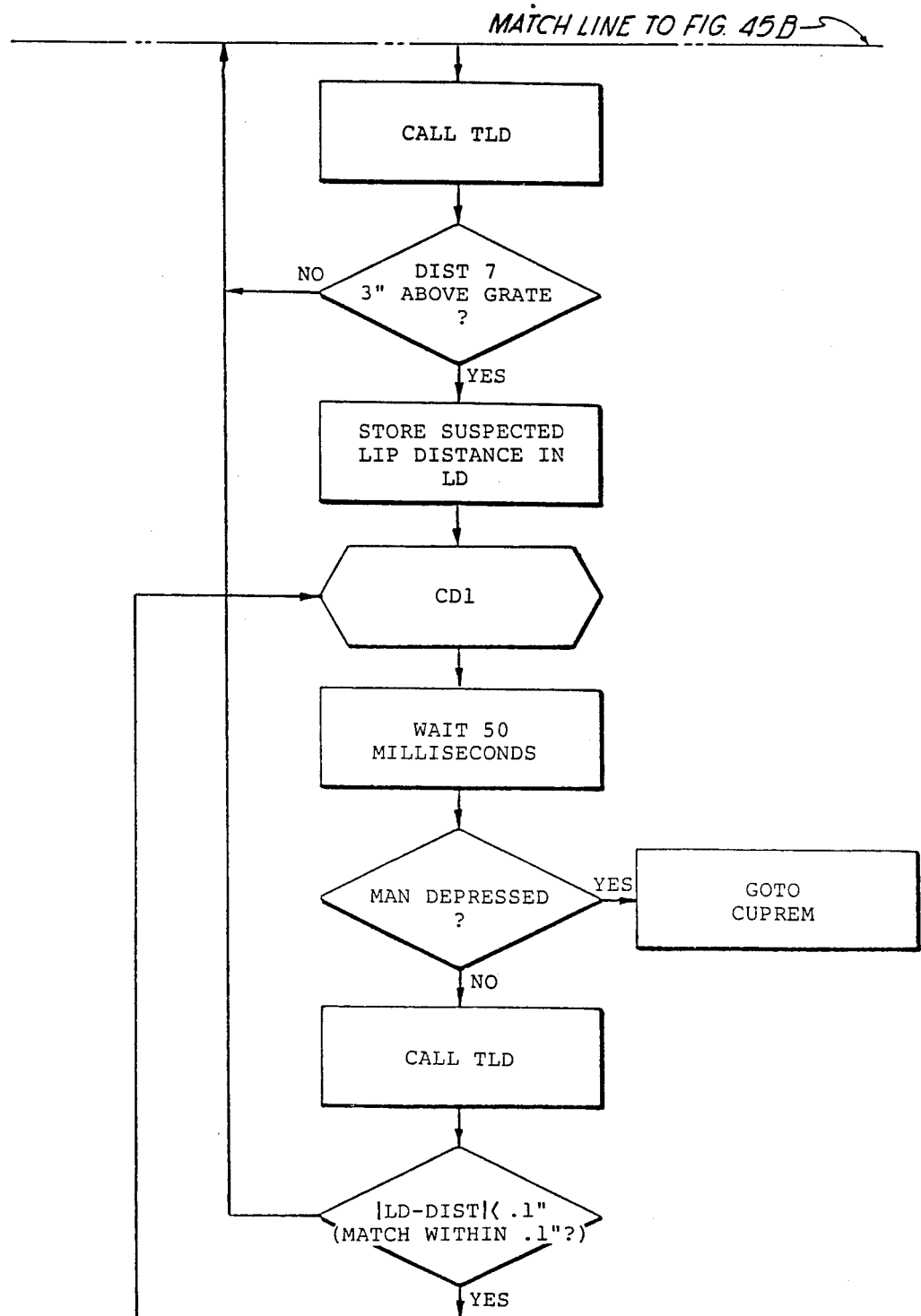
Figure 45D:
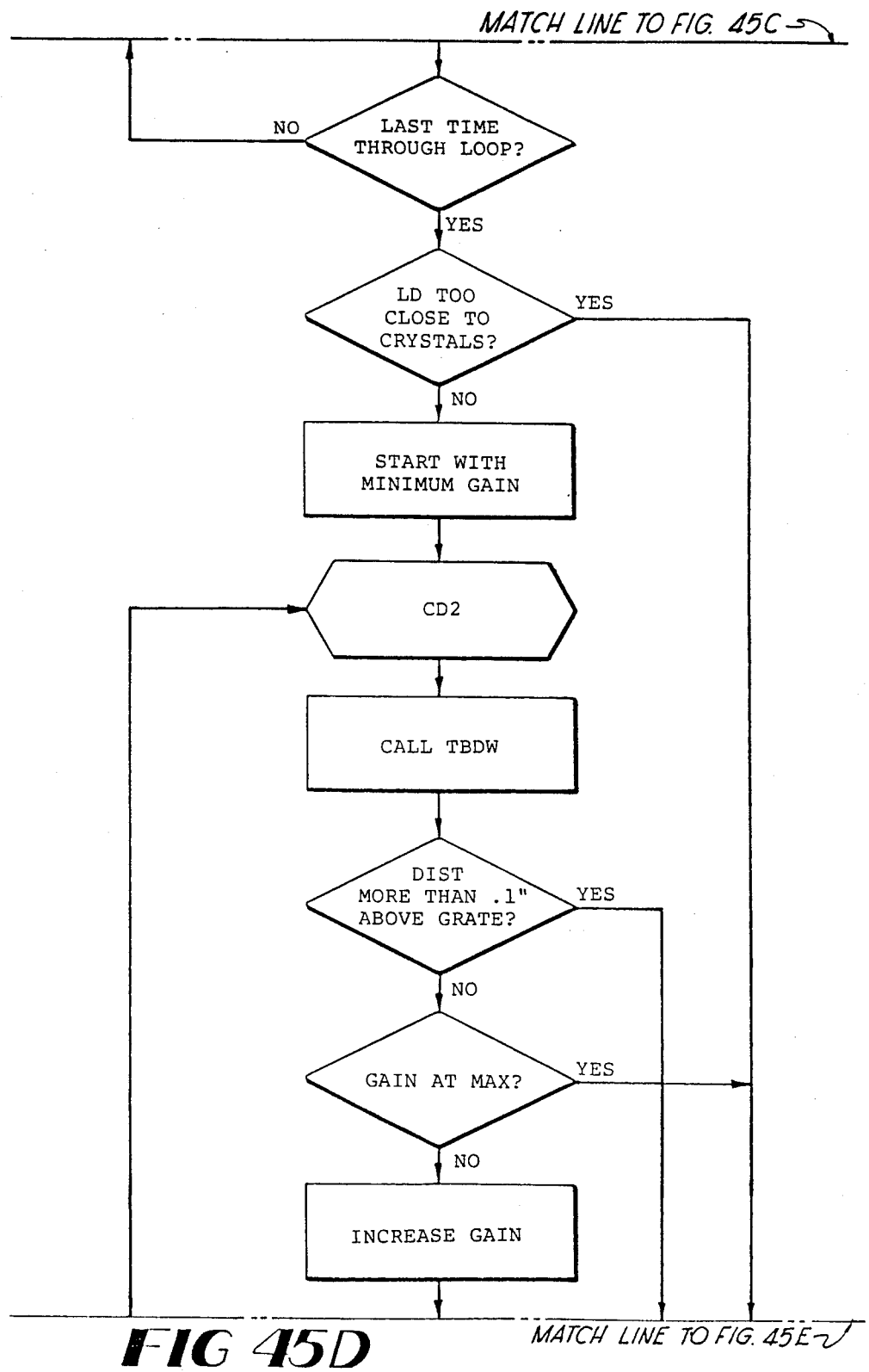
Figure 45E:
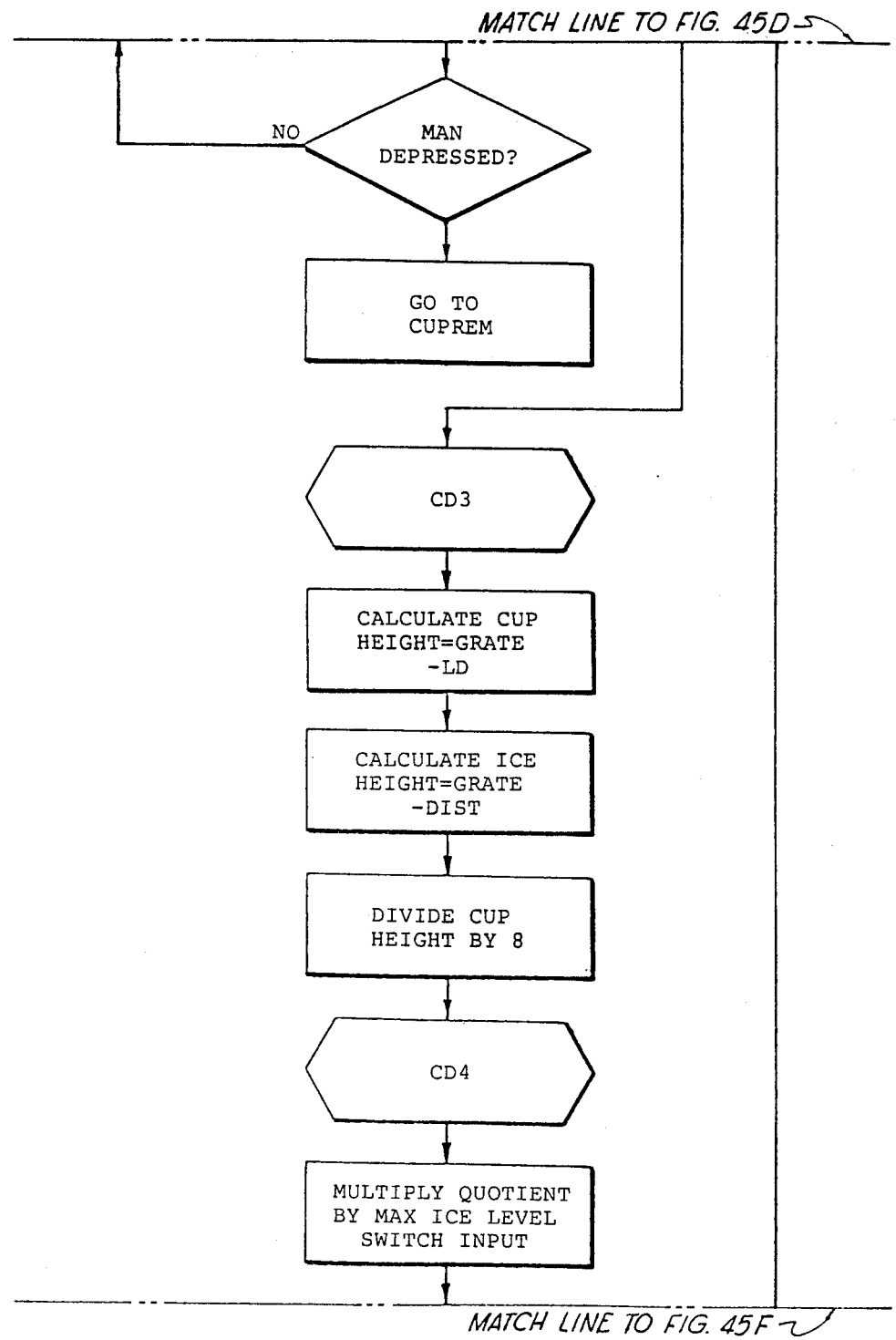
Figure 45F:
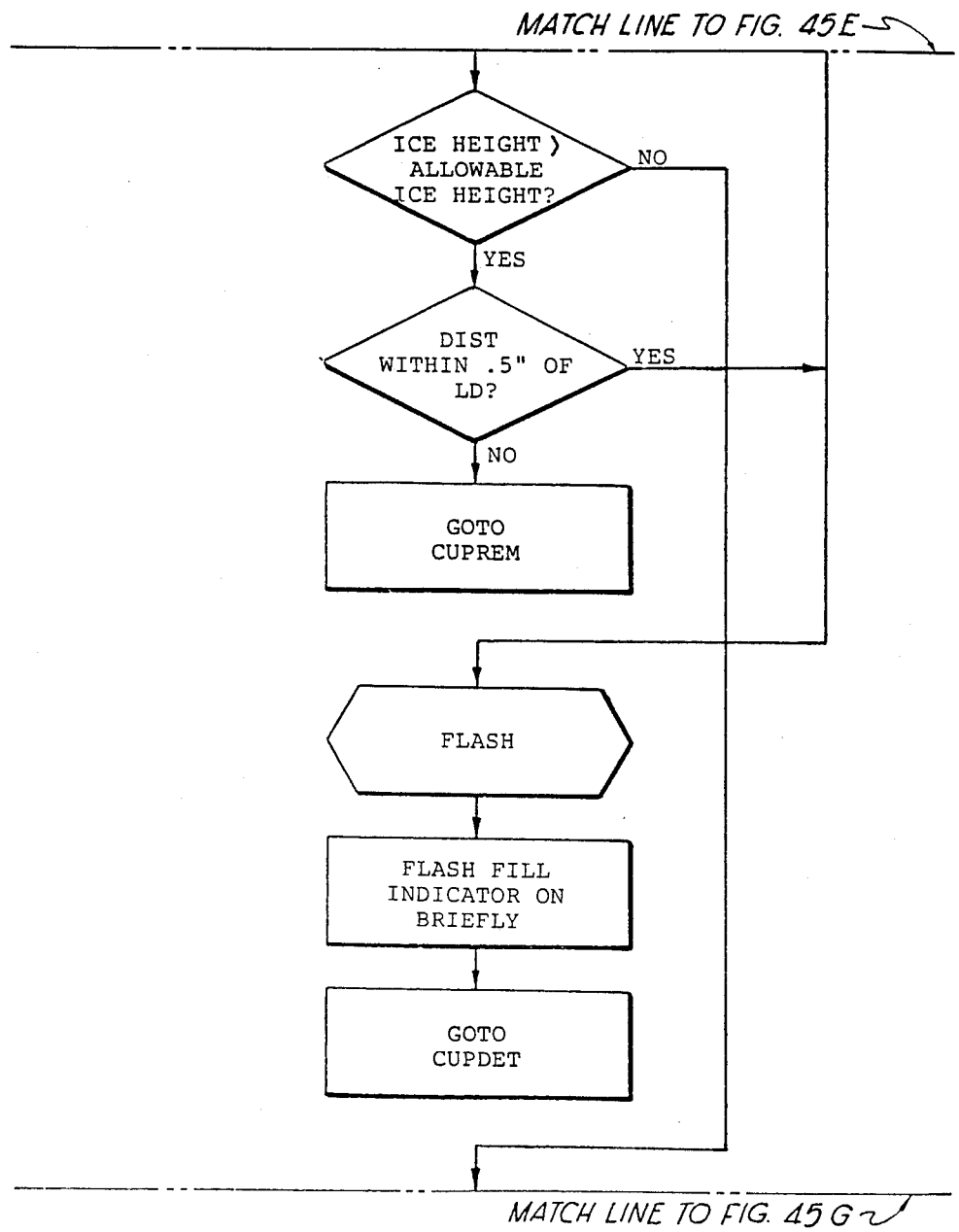
Figure 45G:
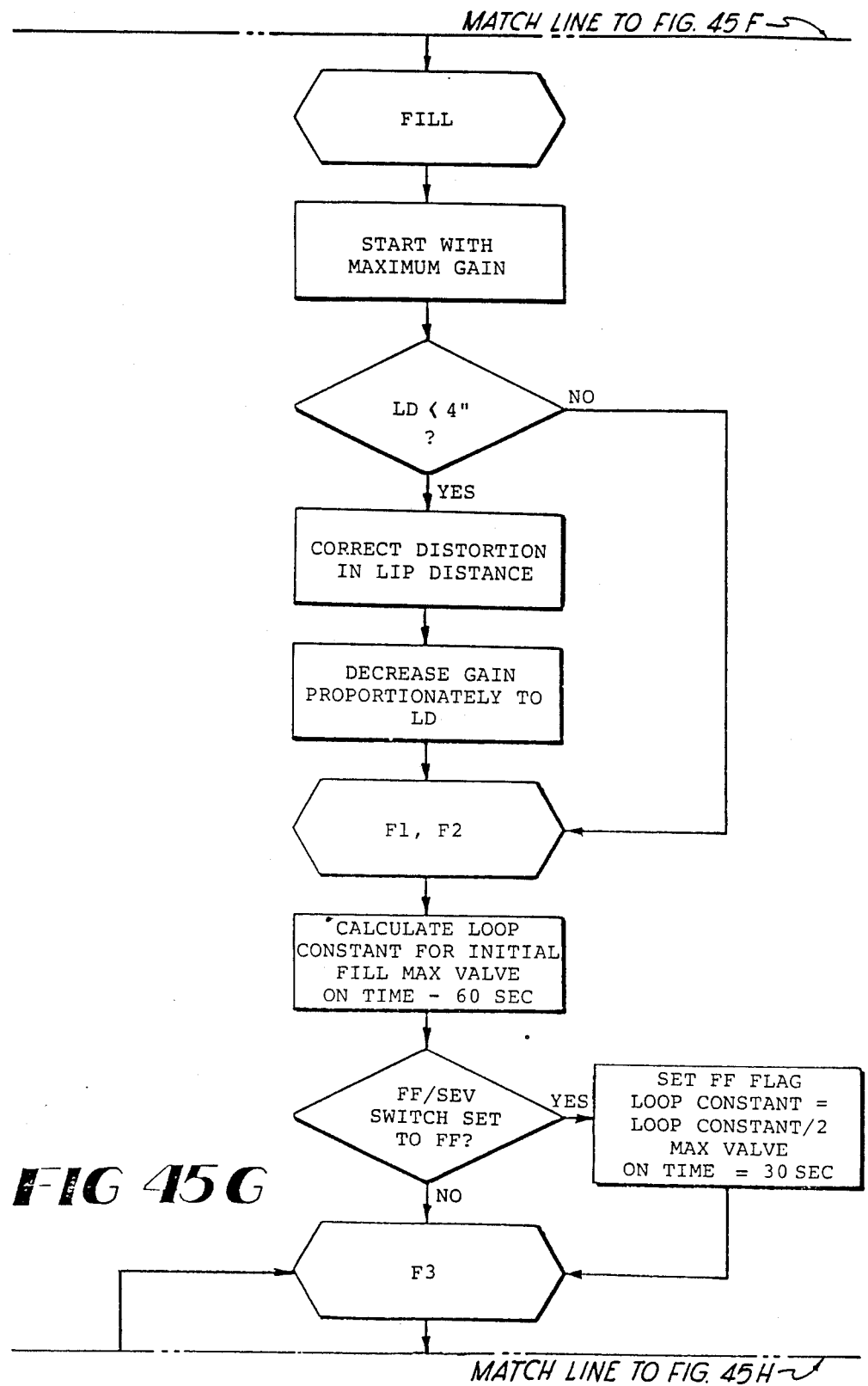
Figure 45I:
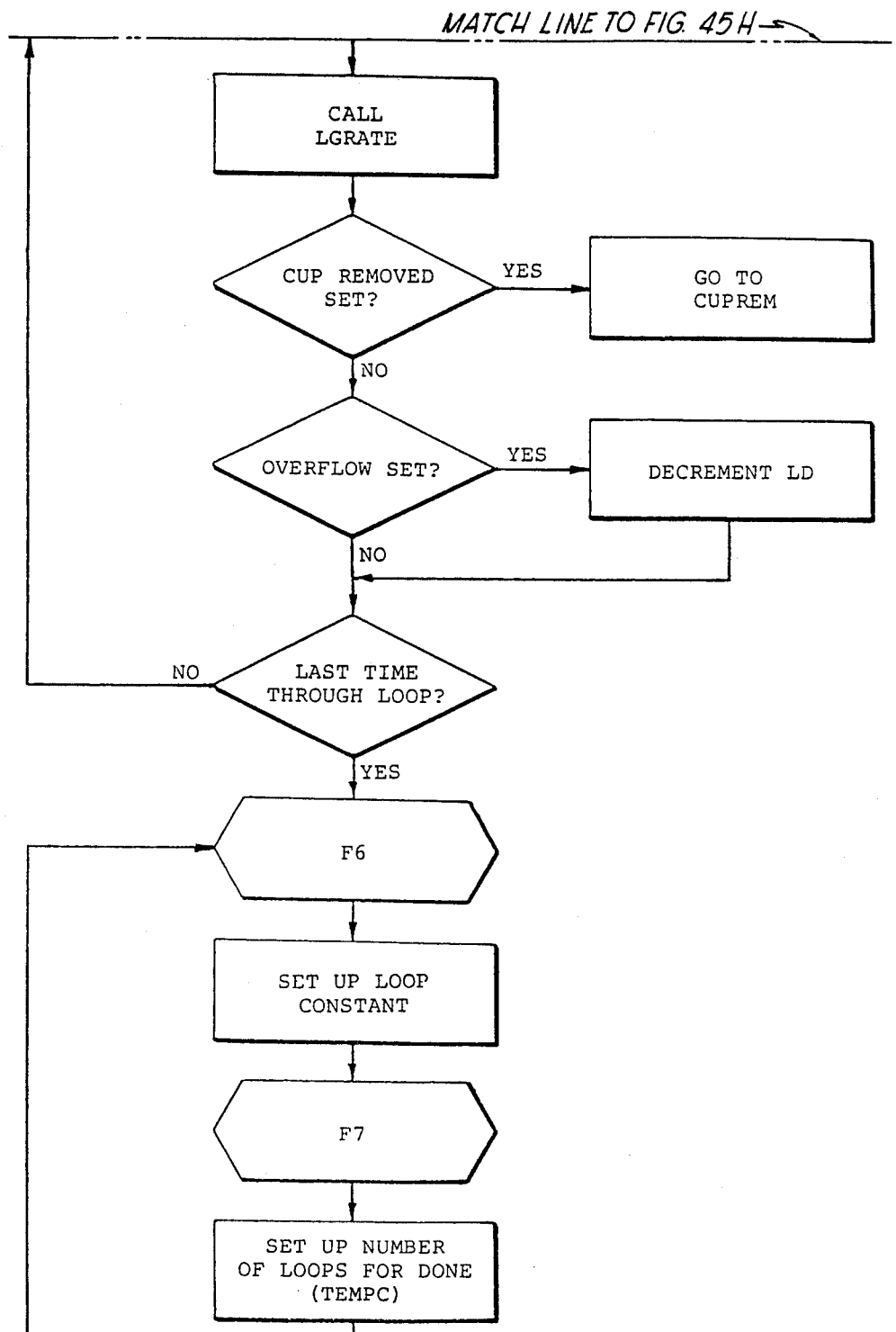
Figure 45K:
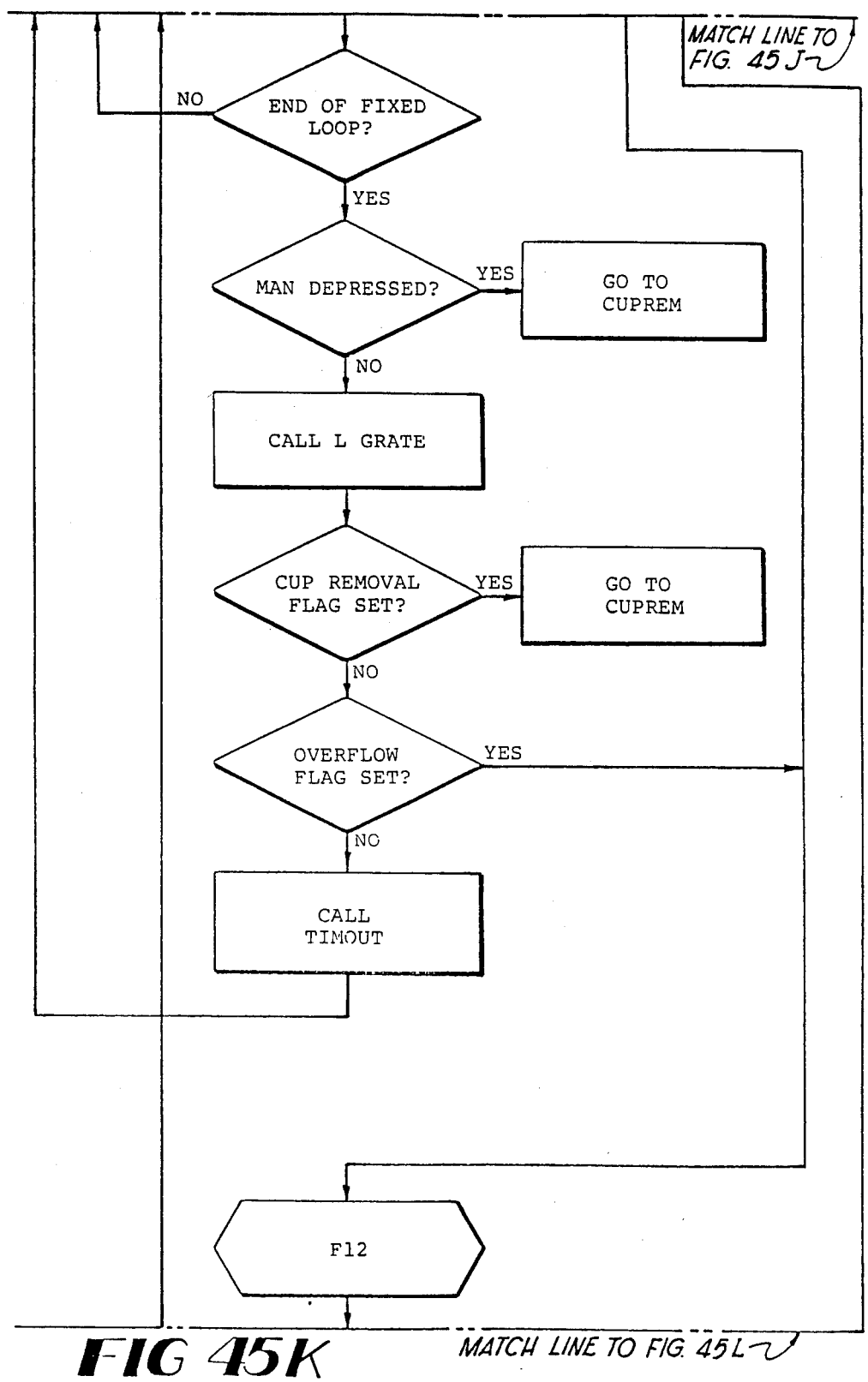
Figure 45L:
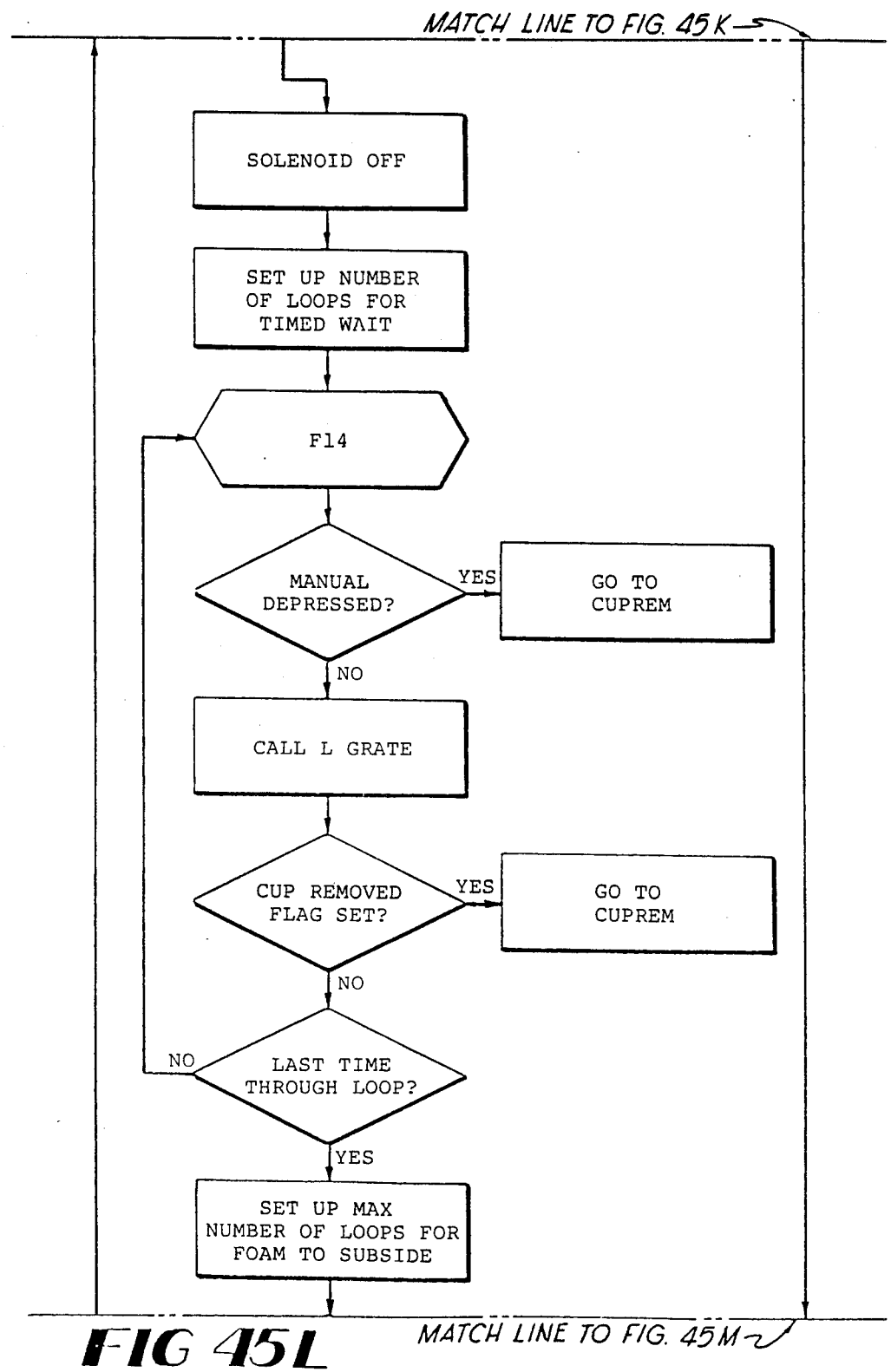
Figure 45M:
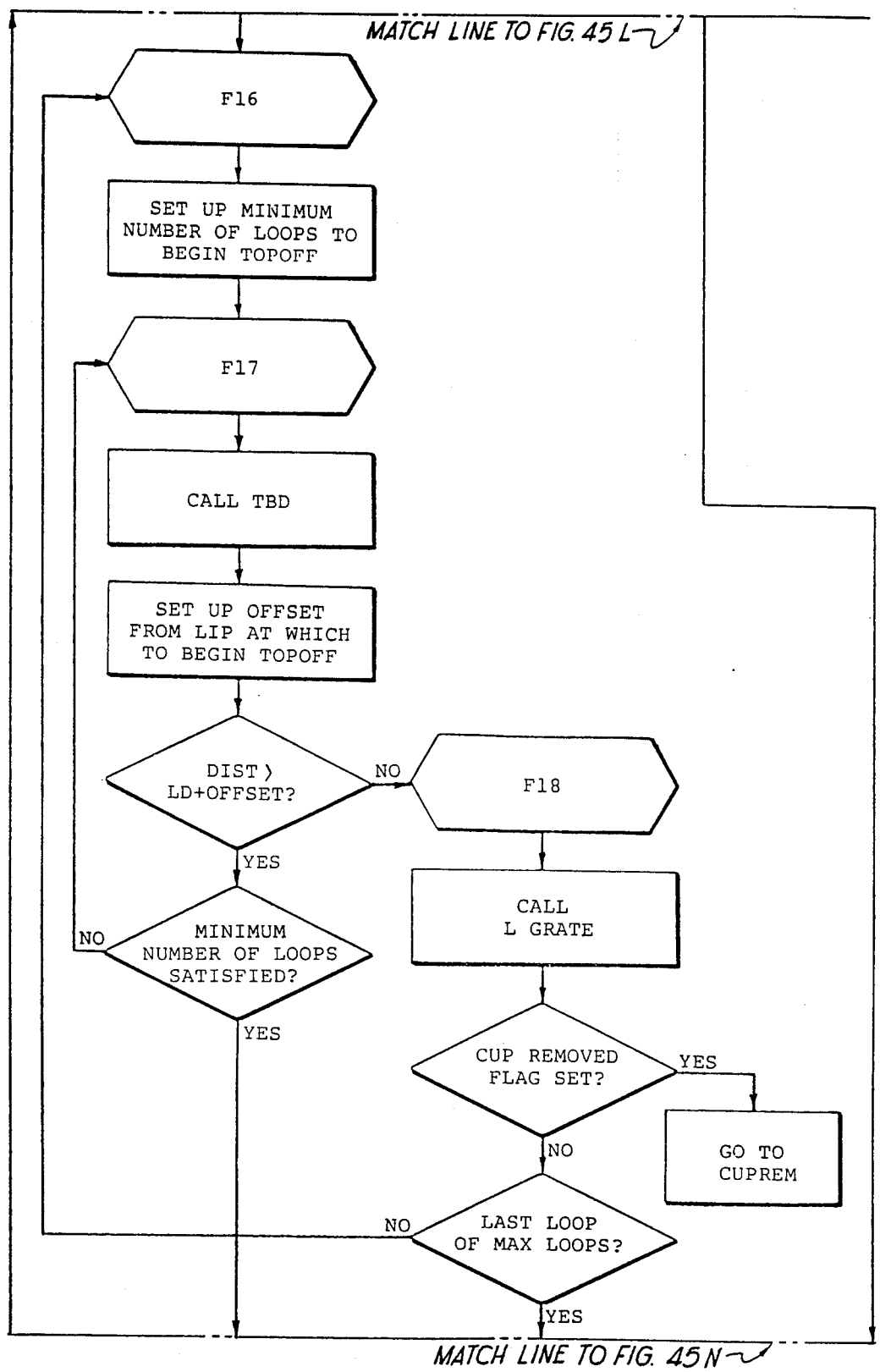
Figure 45:
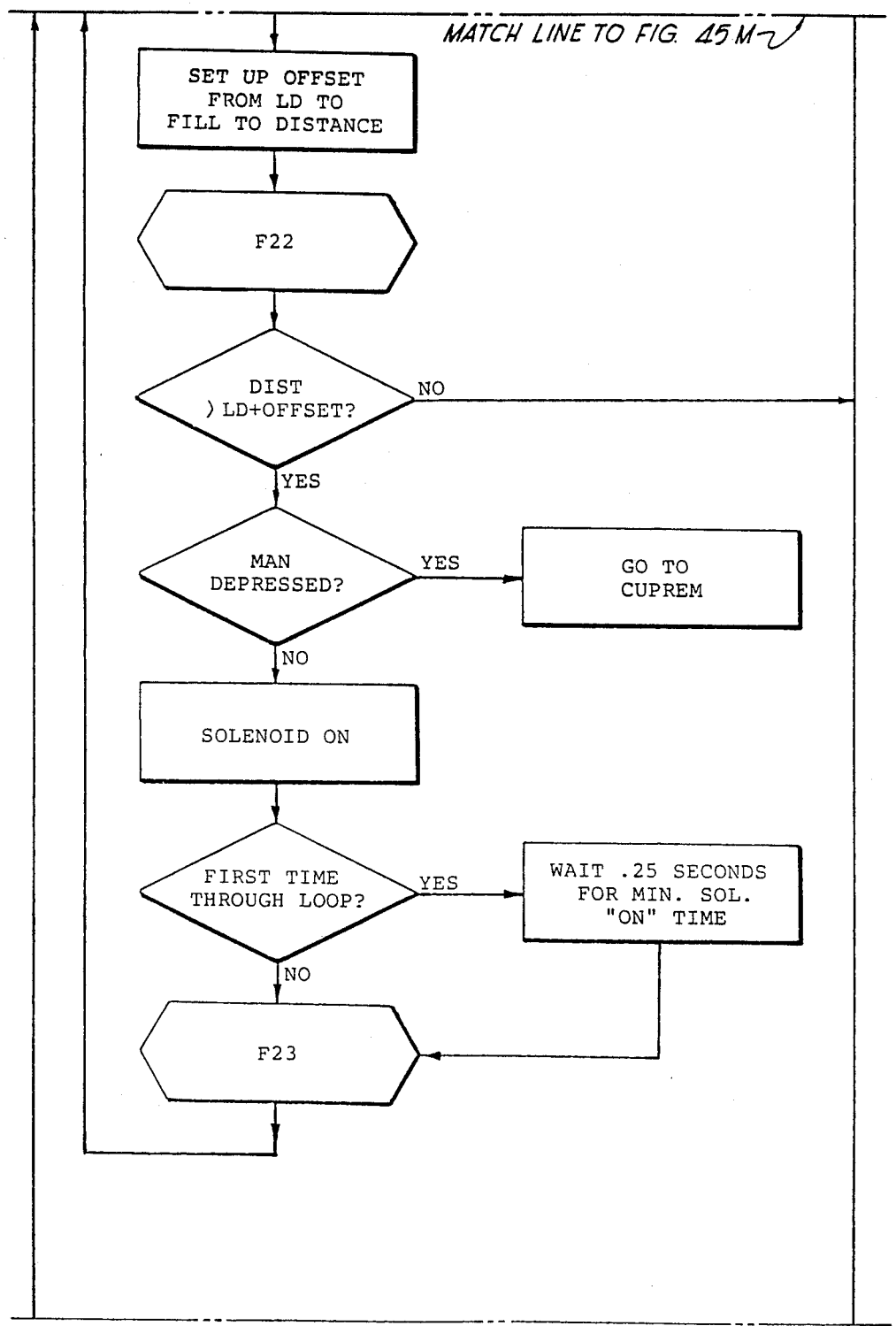
Figure 45P:
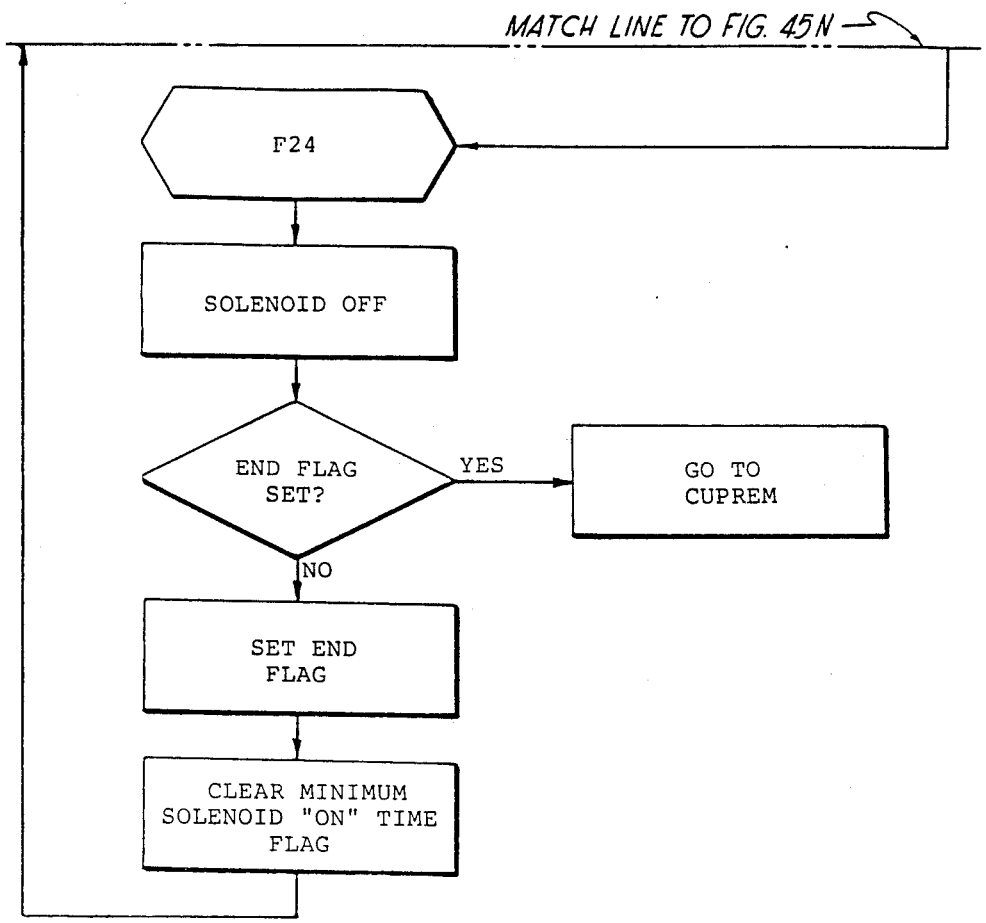
Figure 46:
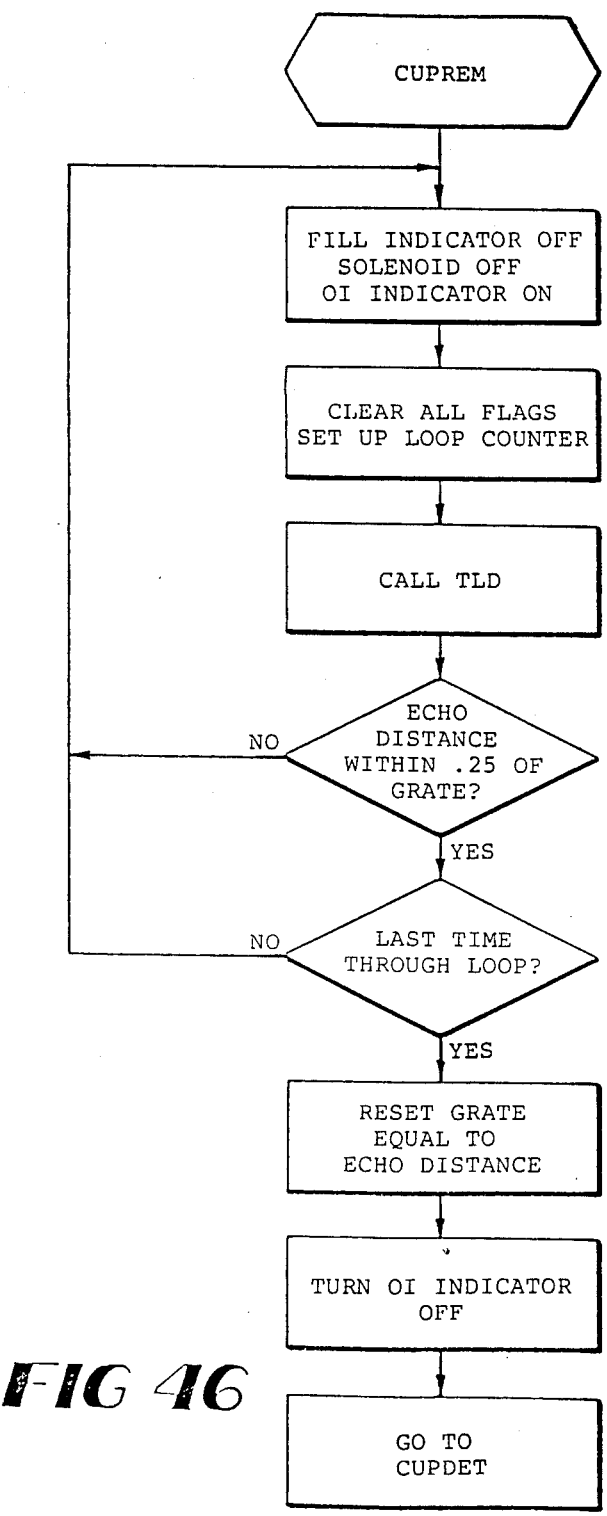

INIT (FIG. 45A) is used when the microcomputer is initialized by the "Master Clear" (hardware). During power up, the first instruction processed is set at location 777 octal. This instruction "GOTO INIT" commands the computer to begin executing this routine, which comprises the following:
a. All RAM are cleared.
b. Wait 1 second for power to stabilize.
c. Call TSTCHK and run the diagnostic routine if test flag is set.
d. Use TLD to look with maximum gain and no window for an echo distance between 7" and 13".
e. If it does not detect an echo within this range, the "Over Ice" indicator on the front panel flashes.
f. If it does detect an echo distance within 7" to 13", an average of 8 samples is stored in RAM as the Grate distance and the program continues at CUPDET.

CUPDET is the Cup Detection routine. This routine collects data using TLD and accepts a cup using the following procedure:
a. The manual fill switch on the front panel is monitored continuously to assure proper operation. If the manual switch is pressed, the computer begins the Cup Removal routine immediately. The DIP switch is read by calling TSTCHK and if the test flag is set, the CUPDET routine ends and the INIT routine begins.
b. A stable lip distance must be established more than 3" above the GRATE. A stable lip distance is defined as 5 consecutive echo distances from TLD separated by 60 milliseconds that correlate within 0.1". This corresponds to the cup lip being stable for 330 milliseconds. If the stable lip distance is too close to the crystals (0.6"), the Lip Distance is rejected, the FILL indicator flashes and CUPDET begins again.
c. A cup bottom or ice level must be discerned that is more than 0.1" above the Grate and more than 0.5" below the lip This is accomplished using TBDW and varying the gain as follows: With minimum gain, obtain an echo distance using TBDW. If the echo distance is not more than 0.1" closer than the grate, then the gain is increased one step and another sample is taken. If the gain reaches the maximum, the FILL indicator flashes and the Cup Detection routine begins again.
d. The Ice/Bottom height is calculated from the last distance obtained as outlined in (C) above and the GRATE and then stored as the actual ice height. The cup height is calculated from the lip distance and the GRATE. The cup height is divided by 8 and the quotient is multiplied by the 3 bit binary number input as selected on the ice level programming switches. This allowable ice height is compared to the actual ice height and the Lip Distance. If the actual ice height is greater than allowed by the switch selection, but less than 0.5" below the Lip Distance, the cup is rejected and the Cup Removal routine begins. If the actual ice height is within 0.5" of the Lip Distance, the cup is not positioned correctly and the FILL indicator flashes before beginning the Cup Detection routine again. If the actual ice height is less than the level selected by the switch, the FILL routine begins.

The FILL routine controls the complete filling and top off operation. The routine limits the solenoid operation to a maximum of 3 On/Off cycles. After each of the first 2 cycles, the routine waits for the foam to settle before starting the next cycle. When the cup is full, the Cup Removal routine begins. If the manual switch is pressed at anytime during the FILL routine, the Cup Removal routine begins immediately. The timeout subroutine is called during the time the solenoid valve is turned on by the fill program to monitor the valve on time. If the maximum valve on time is exceeded, the timeout subroutine turns the valve off and does not return on the fill routine. A detailed description of the FILL routine follows:
a. Before the solenoid is actuated, several checks and corrections are made. The gain is initially set at maximum. If the Lip Distance is less than 4", the gain is adjusted with the empirically derived equation:
Gain=Gain ⅛ (4" lip distance) If the Lip Distance is less than 4", the Lip Distance is adjusted with the empirically derived equation:
Lip Distance=Lip Distance ⅛ (4" Lip Distance)
The Time Constant for this particular cup height is calculated with the equation:

Time Constant=cup height/4 for SEV and cup height /8 for Fast Flow.

This Time Constant is used in the first of the three cycles to provide an initial fill time proportional to the cup height.

b. The gain must be adjusted such that the fluid level is detected and the lip is not during the period when the cup vibrates such as at the beginning of a FILL. Also if the cup was not positioned perfectly, the Lip Distance may be slightly farther than originally detected. To adjust the gain, an initial filling period proportional to cup height is allowed to minimize cup vibration and adjust gain as necessary. During this time period the routine uses TBD to check if the echo distance is within 0.75" of the stored Lip Distance. If it is, the gain is reduced one step. If the gain reaches minimum, the Cup Removal routine begins. This time is also used to adjust the Lip Distance as follows: LGRATE is called and if an overflow is detected then the Lip Distance is decremented (an overflow in LGRATE is defined as more than 0.1" less than the stored Lip Distance). If LGRATE detects a missing cup then the Cup Removal routine begins immediately. At the end of this period, the solenoid valve stays on.

c. During the next time period the routine uses TBDW to monitor the liquid level. If the Foamy/Flat switch is set to Foamy, the solenoid turns off when the liquid level is within 0.5" for SEV or 0.7" for FFV. If the Foamy/Flat switch is set to Flat, the solenoid is not turned off until the liquid level reaches 0.2" for SEV and 0.3" for FFV, at which time the cup removal routine begins. This condition must be met in two consecutive checks for the solenoid to turn off. The Grate/Overflow detector subroutine checks to see if the cup has been removed or if TBDW has missed the liquid level rising and an overflow is imminent. If the cup is missing, the cup removal routine begins. If there is an overflow indicated, the solenoid is turned off.

d. A 4-second pause begins at this time to allow the foam to settle. The Grate/Overflow subroutine checks continuously for the cup to be removed. If it is, the cup removal routine begins immediately.

e. After the pause, another 4-second time period starts. Using TBD, the foam level is monitored. If the foam drops below 0.4" for 10 consecutive checks, this period ends and the first top-off period begins. If the foam does not drop below 0.4" within 4 seconds, the first top-off period begins anyway. The Grate/Overflow subroutine continuously checks for a missing cup. If a missing cup is detected, the cup removal routine begins.

f. The first top-off cycle uses TBD to determine if the liquid/foam level is within 0.1" for a normal 1½ ounces per second valve assembly and 0.05 for the faster 3 ounces per second valve assemblies. If this condition exists, the solenoid is not turned on and this cycle ends. If not, then the solenoid is turned on until the condition is met. For stability, the solenoid has a minimum on time of 0.25 seconds.

g. A repeat of "D", "E", and "F" occurs now to implement the second top-off cycle with the exception that in "F" the values are 0.2" for the normal 1½ ounces per second valve assembly and 0.3" for the faster 3 ounces per second valve assembly. The cup removal routine (CUPREM) turns the fill indicator off, the solenoid off, and the Over-Ice indicator on. It uses TLD and waits for an echo distance within 0.25" of the Grate. When this condition exists a new Grate distance is stored, the Over-Ice indicator turns off, and the Cup Detection routine begins again.

A third and preferred embodiment of the present invention will now be described with reference to FIGS. 47–57 and the source code attached hereto as Appendix A.

Figure 47:
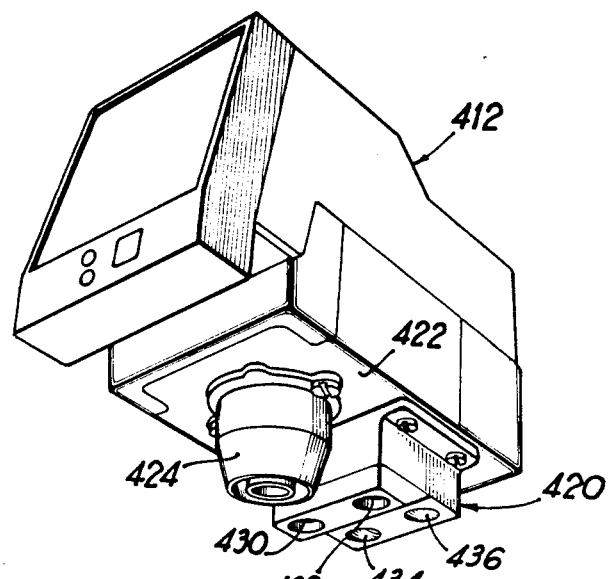
FIG. 47 is a perspective view of a beverage dispenser valve assembly using the automatic filling system of the preferred, four crystal embodiment of this invention.
Figure 48:
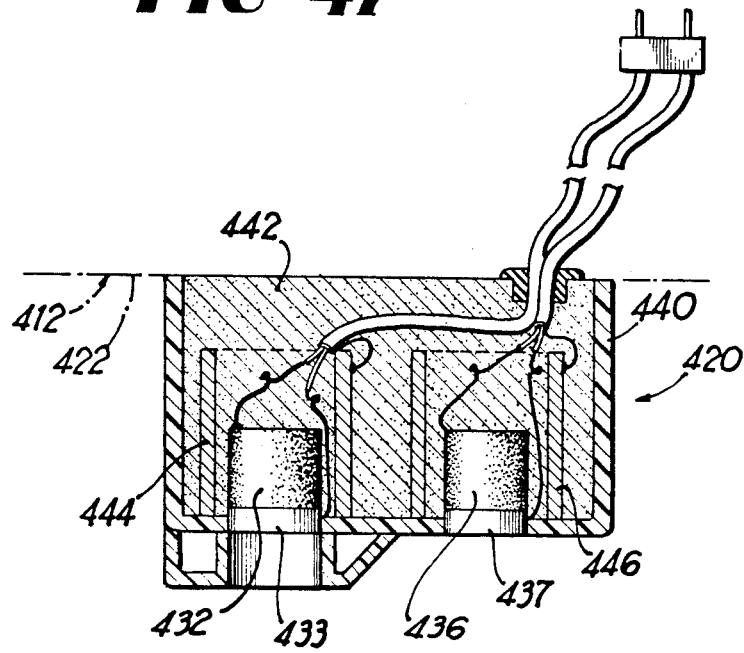
FIG. 48 is a cross-sectional side view of the transducer assembly shown in FIG. 47.
Figure 49:
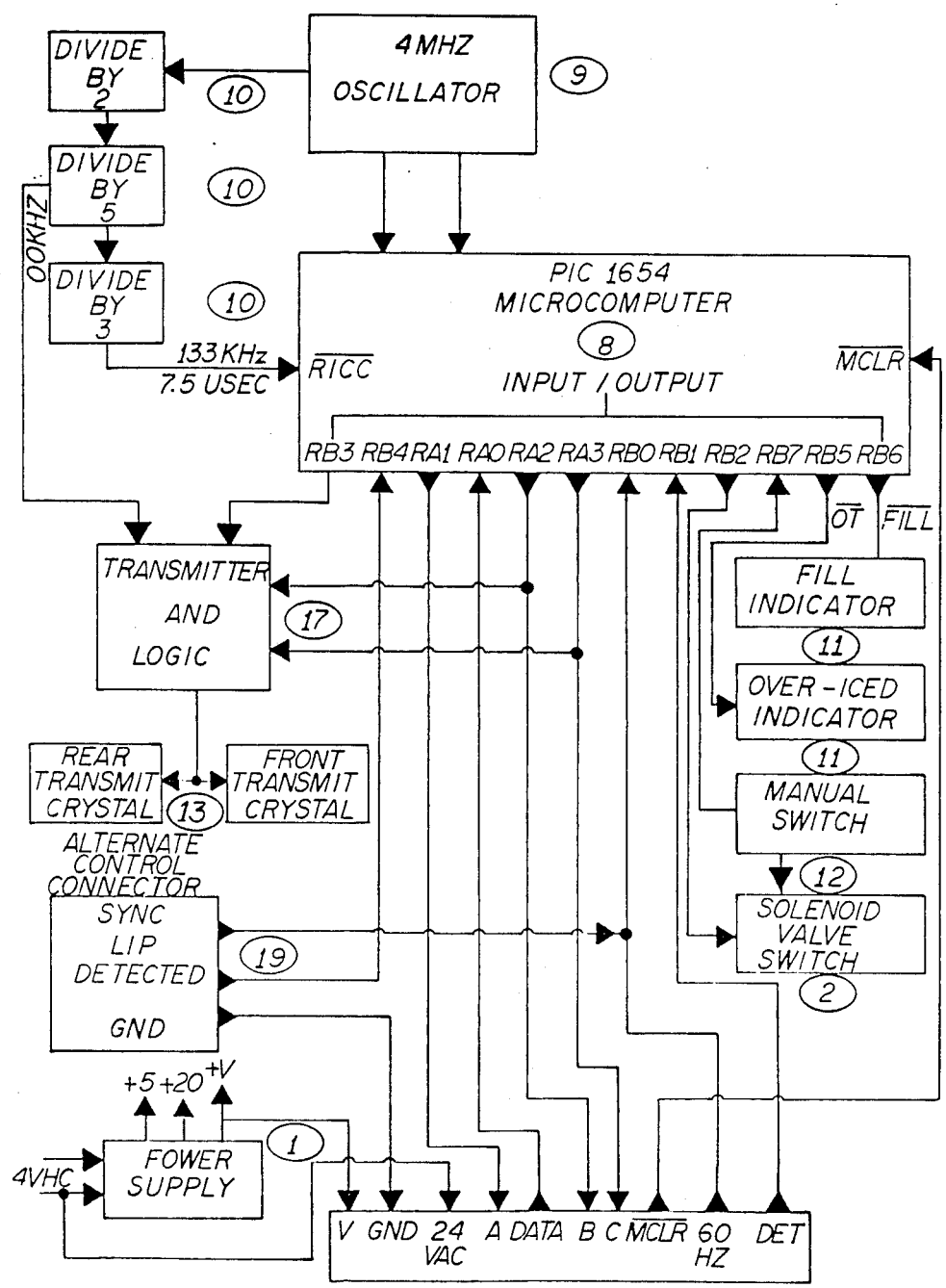
FIG. 49 is a block diagram of part of the electronics package of the four crystal embodiment.
Figure 50:
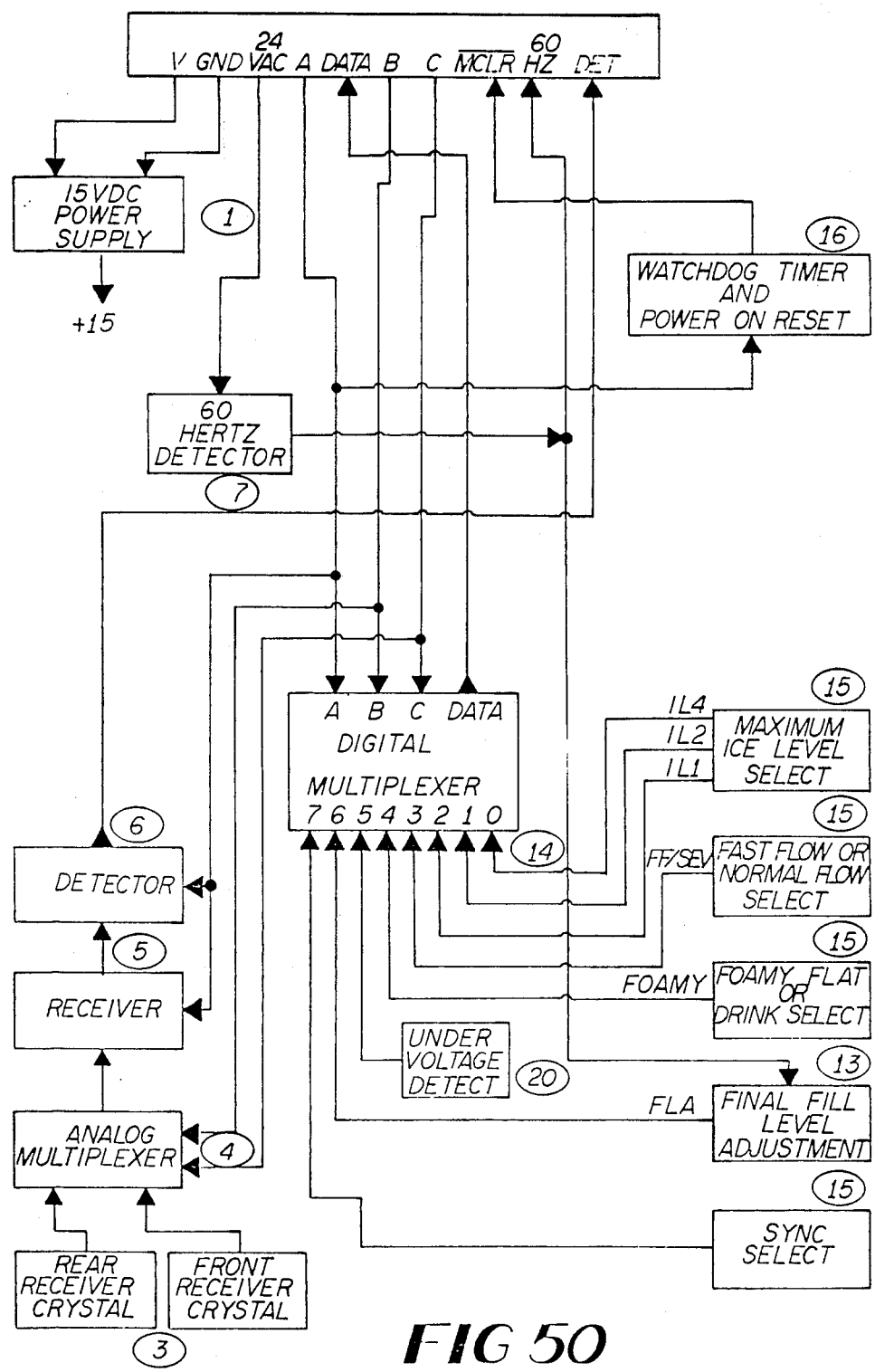
FIG. 50 is a block diagram of another part of the electronics package of the four crystal embodiment.
Figure 51:
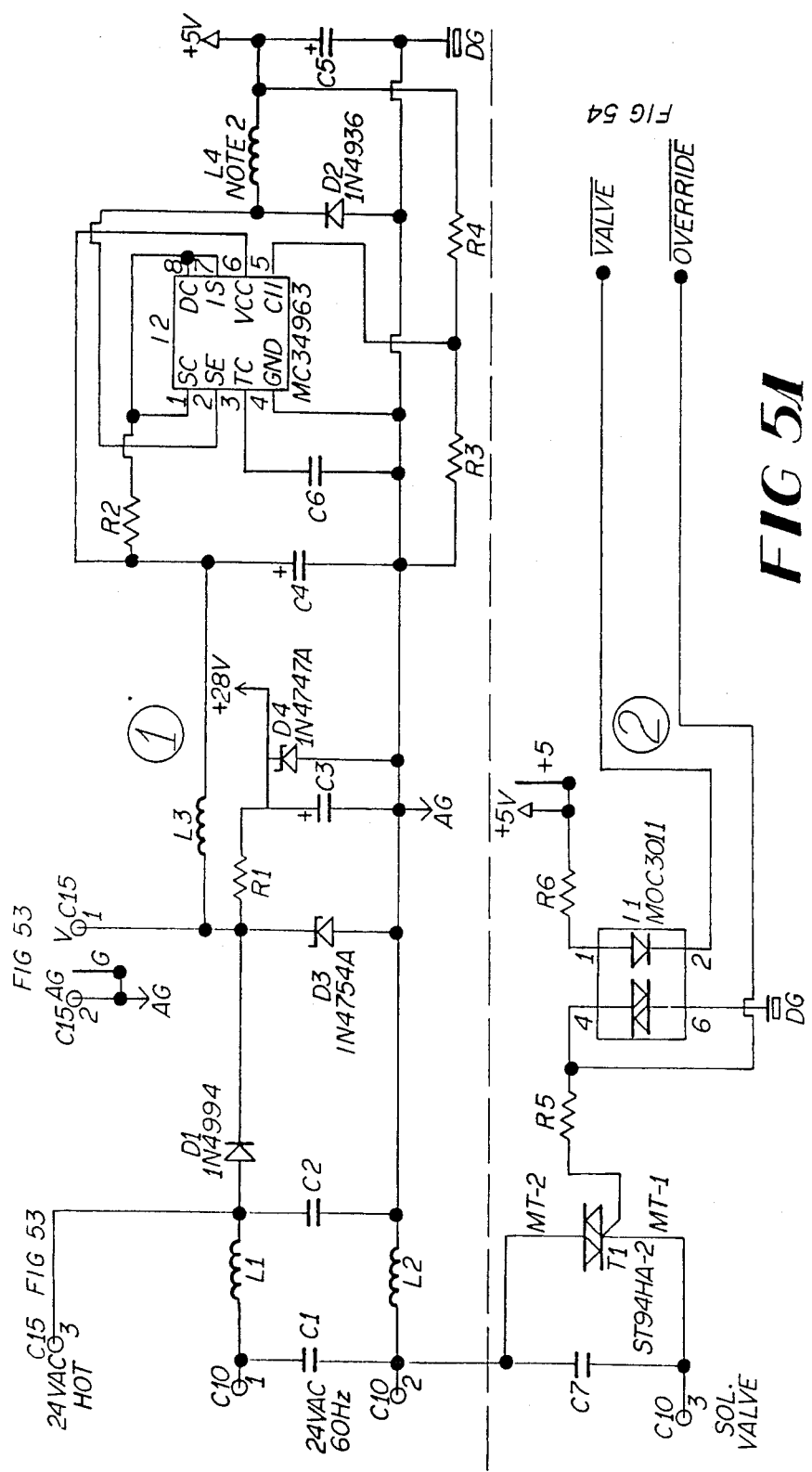
FIG. 51 is an electric schematic of the power supper shown in FIG. 49.
Figure 57B:
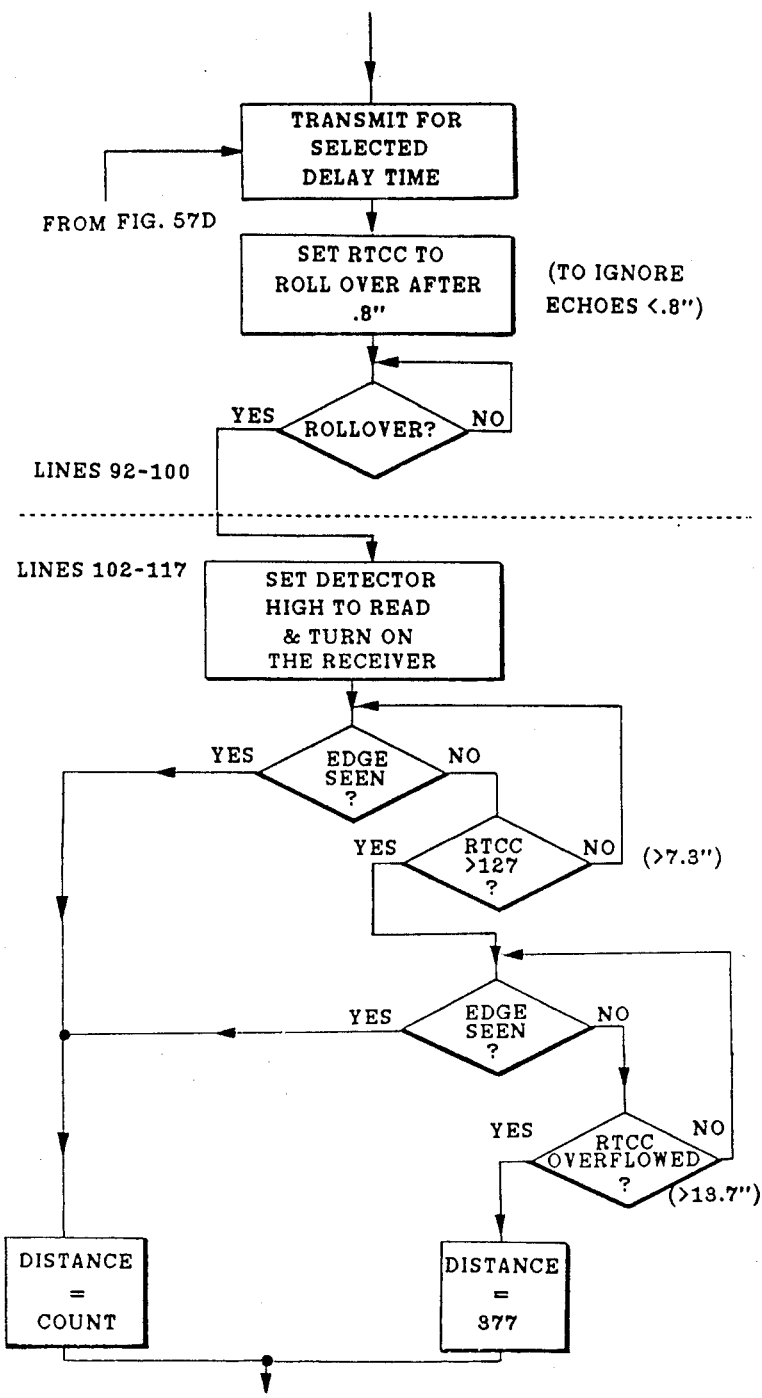
FIGS. 57A-57Z are flow charts of the software used in the four crystal embodiment.
Figure 57C:
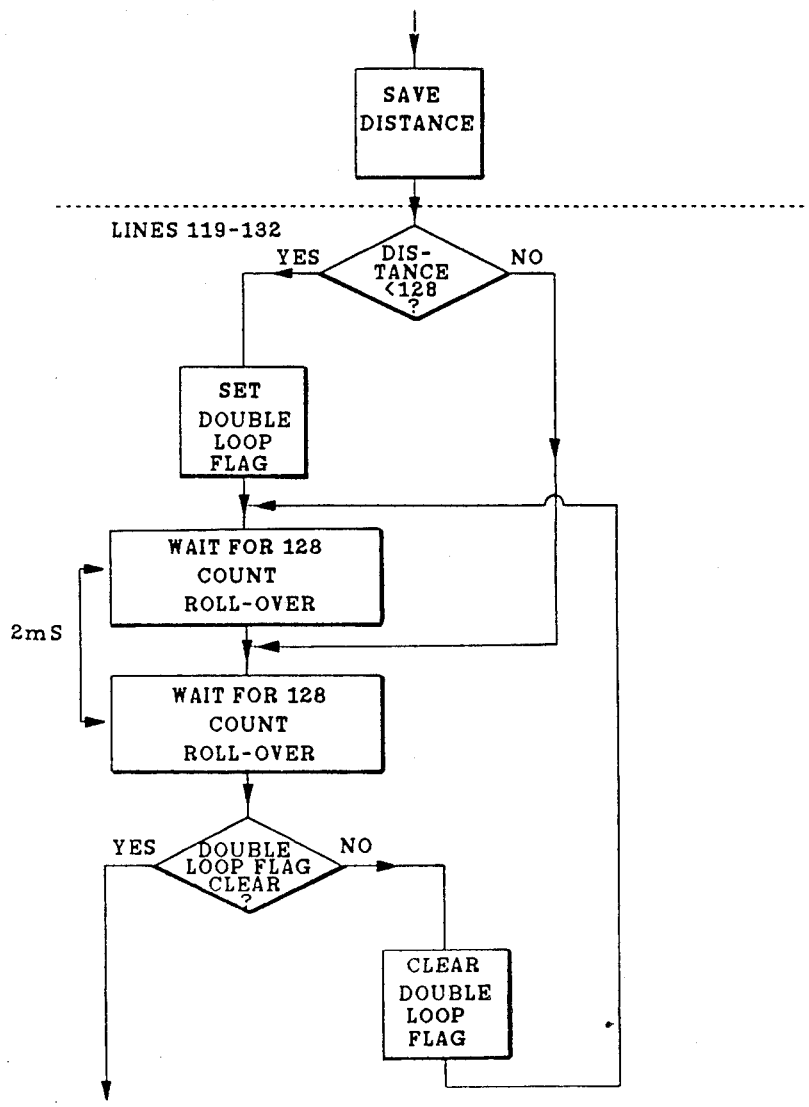
Figure 57D:
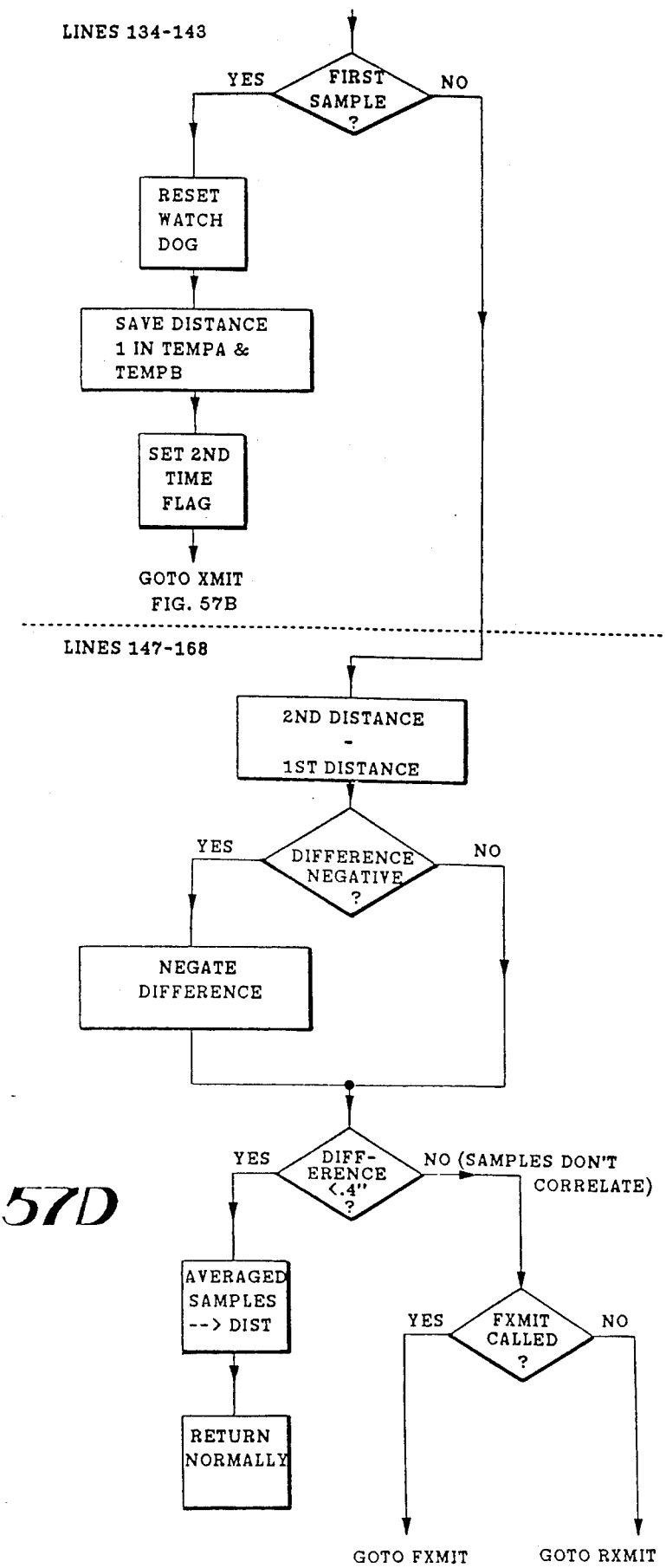
Figure 57E:
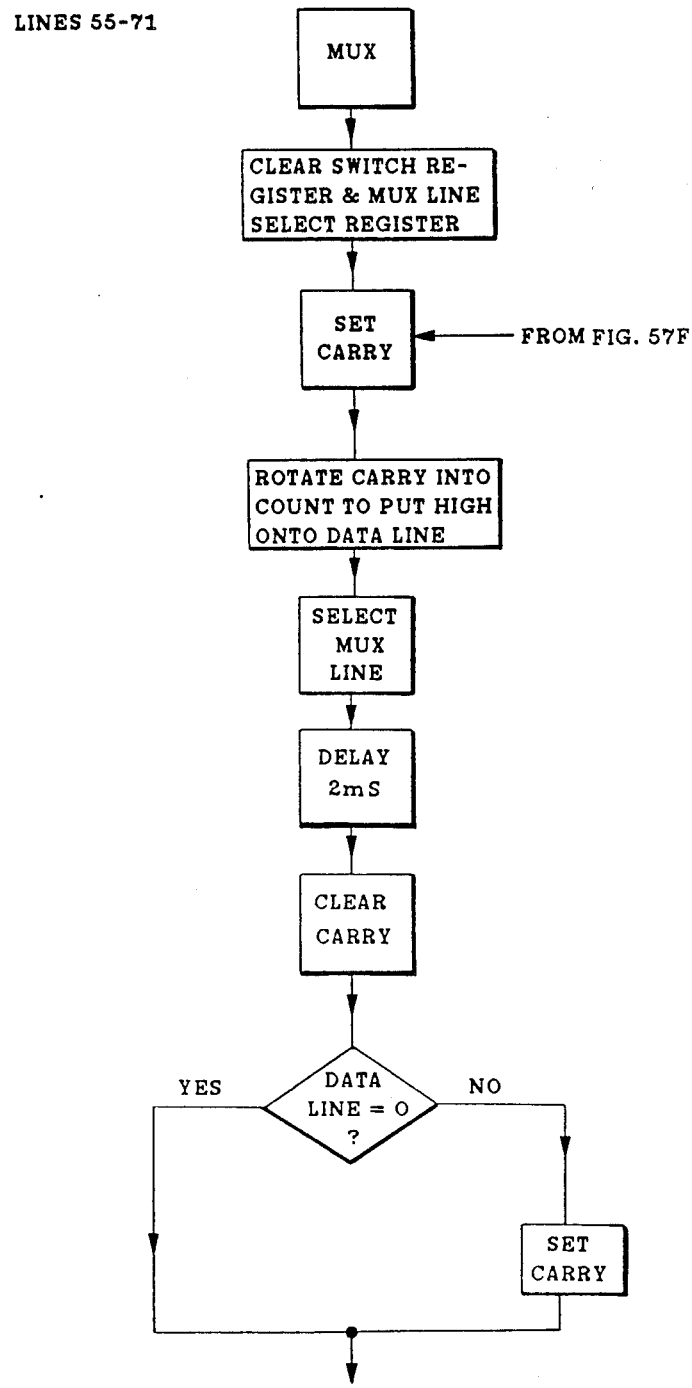
Figure 57F:
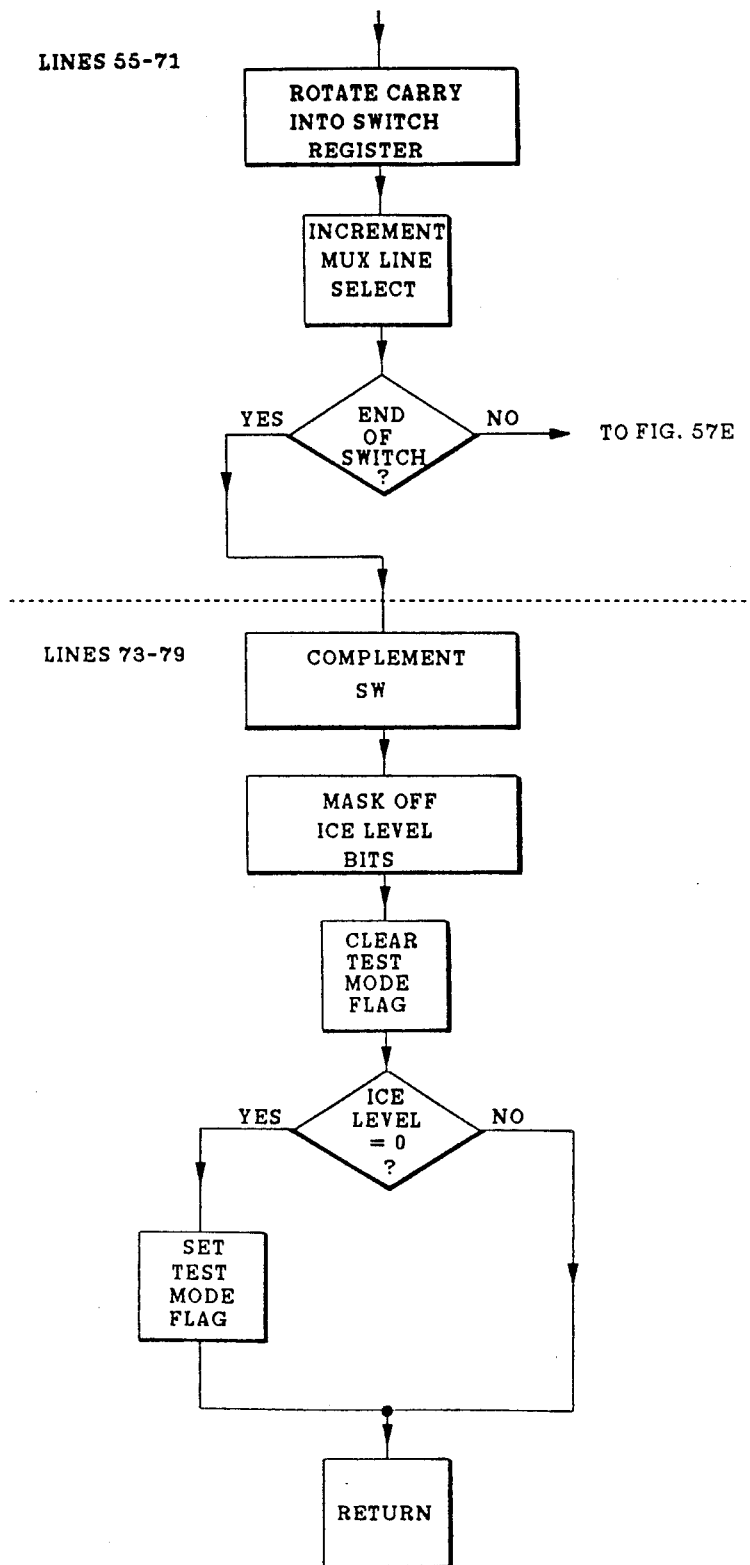
Figure 57G:
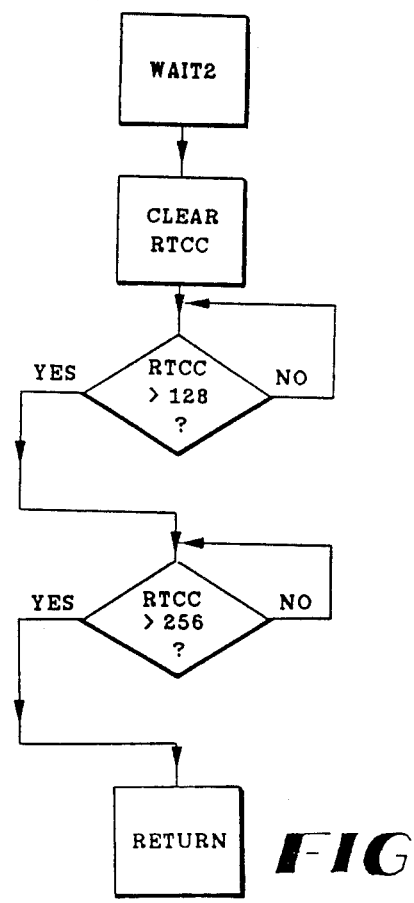
Figure 57H:
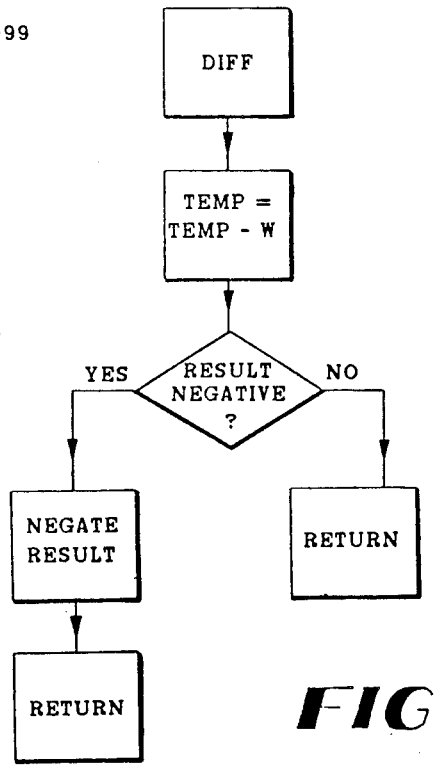
Figure 57I:
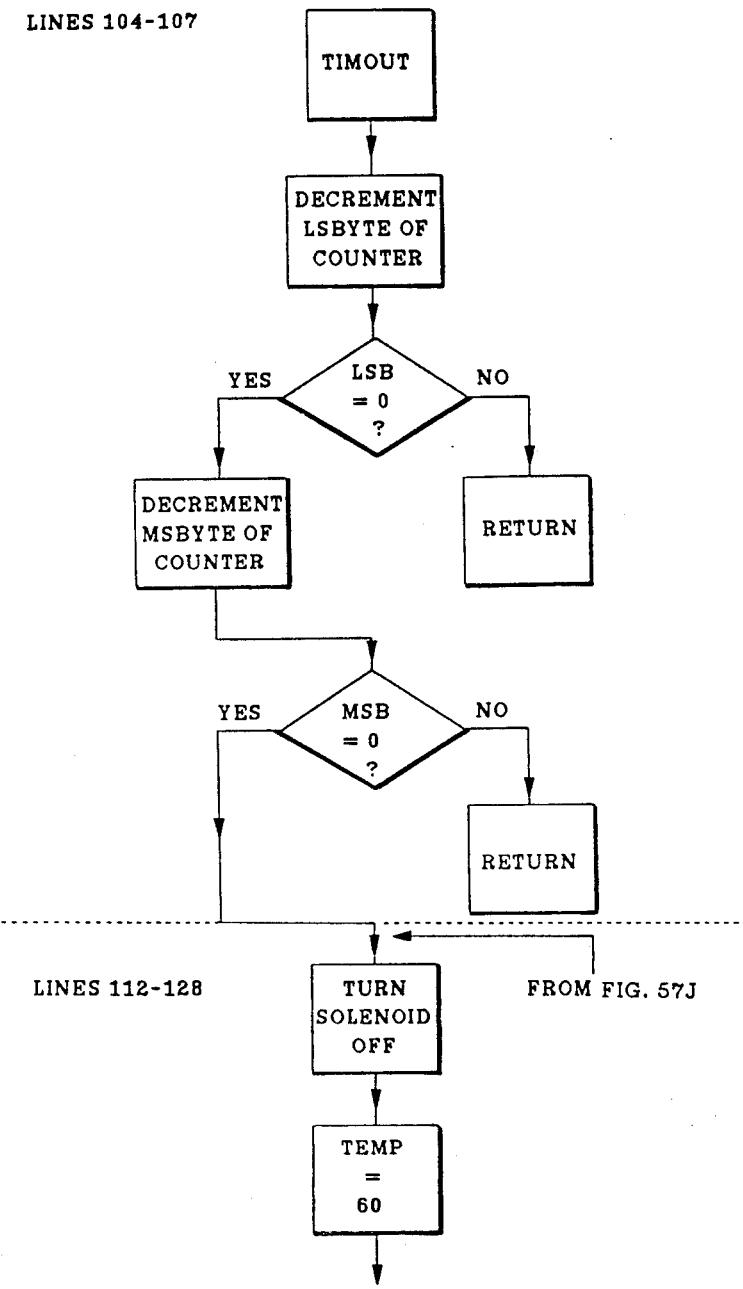
Figure 57J:
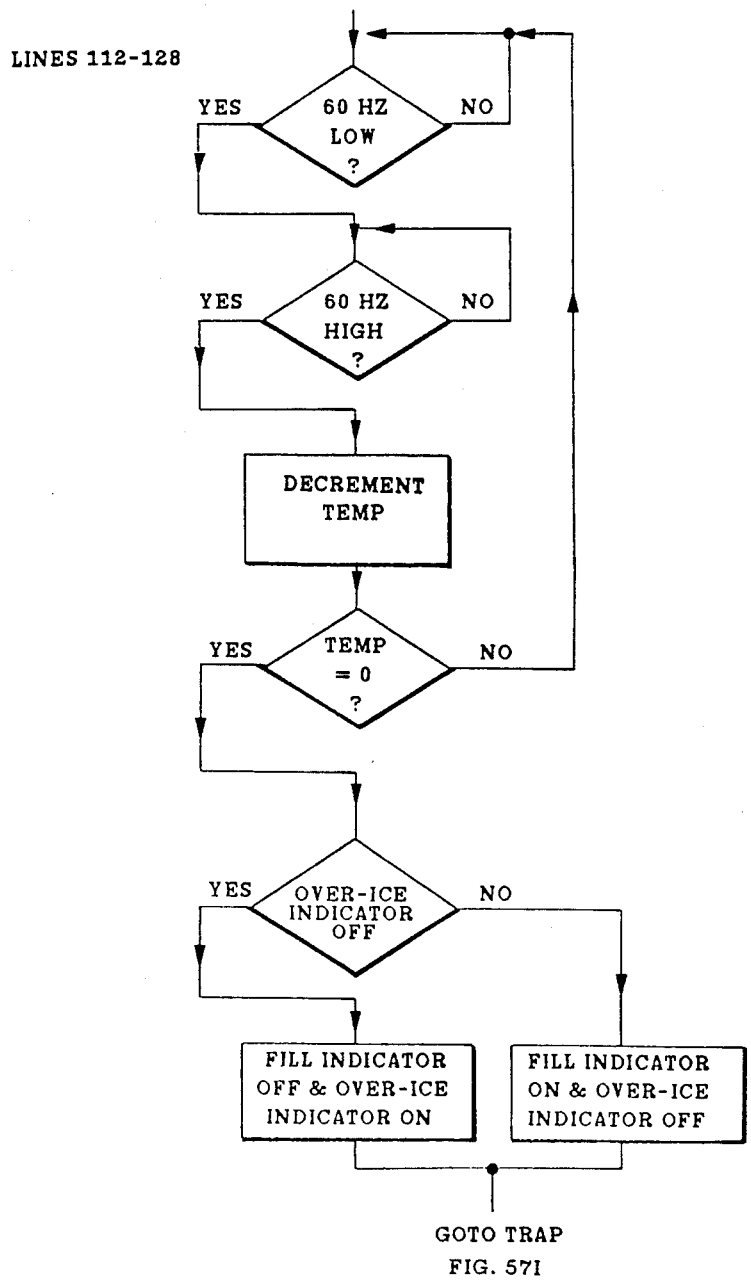
Figure 57K:
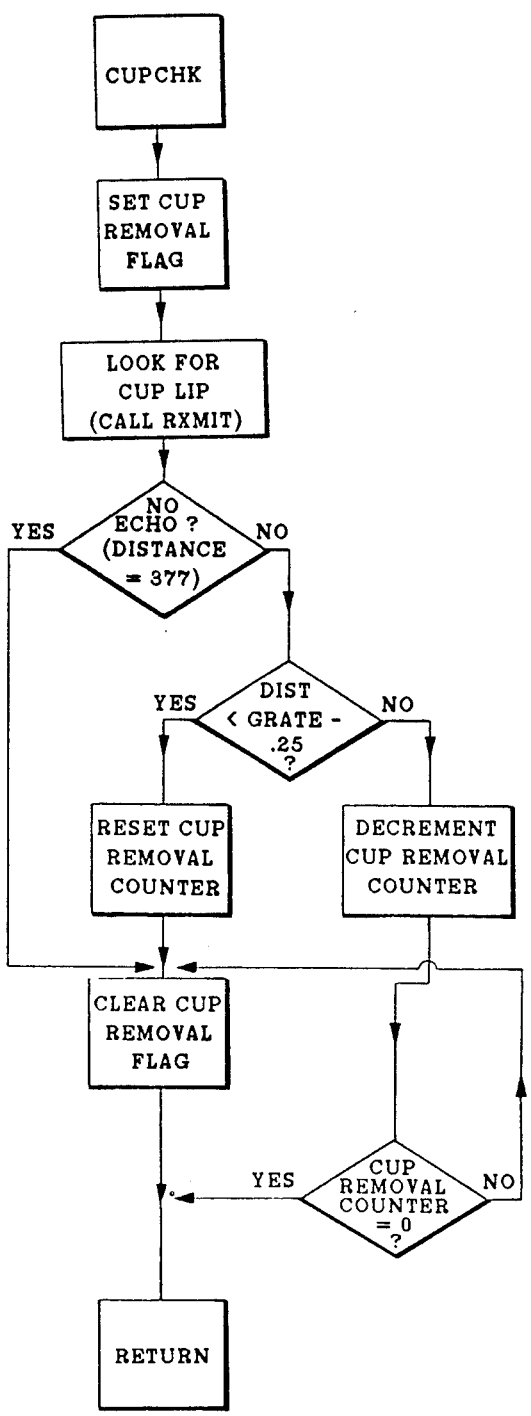
Figure 57L:
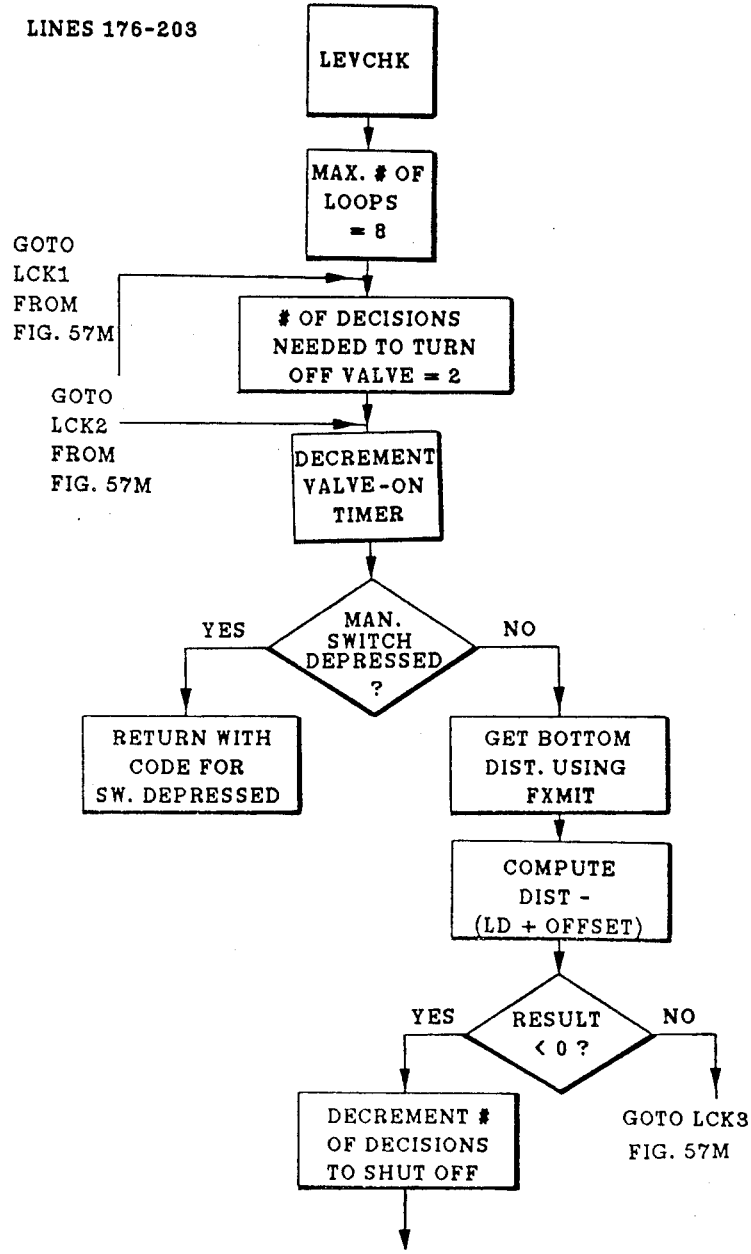
Figure 57M:
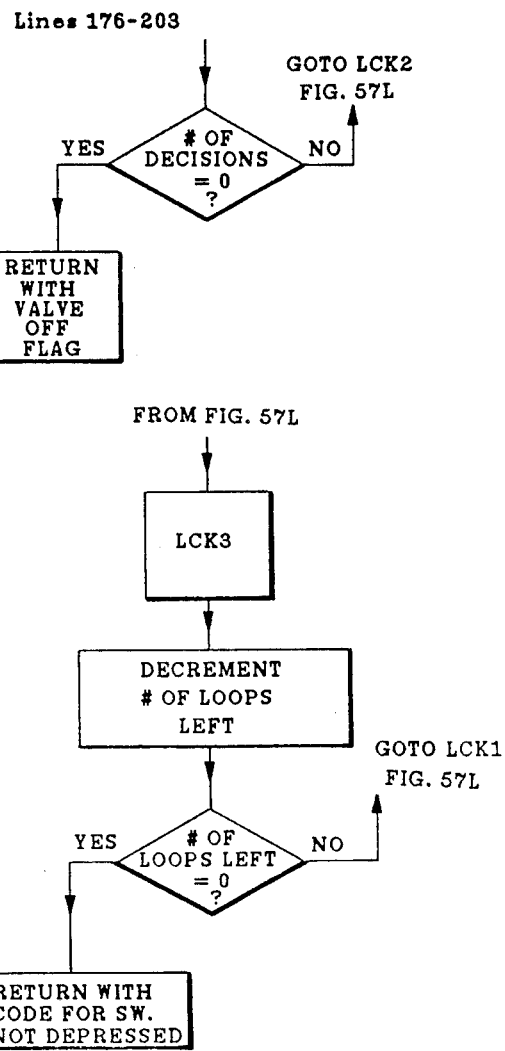
Figure 57N:
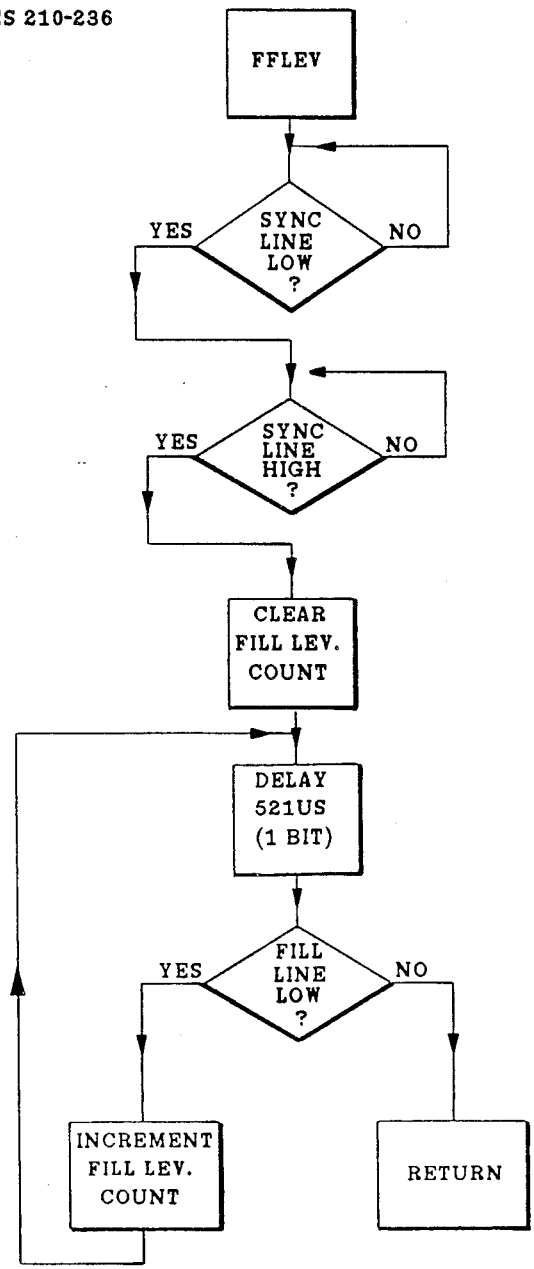
Figure 57O:
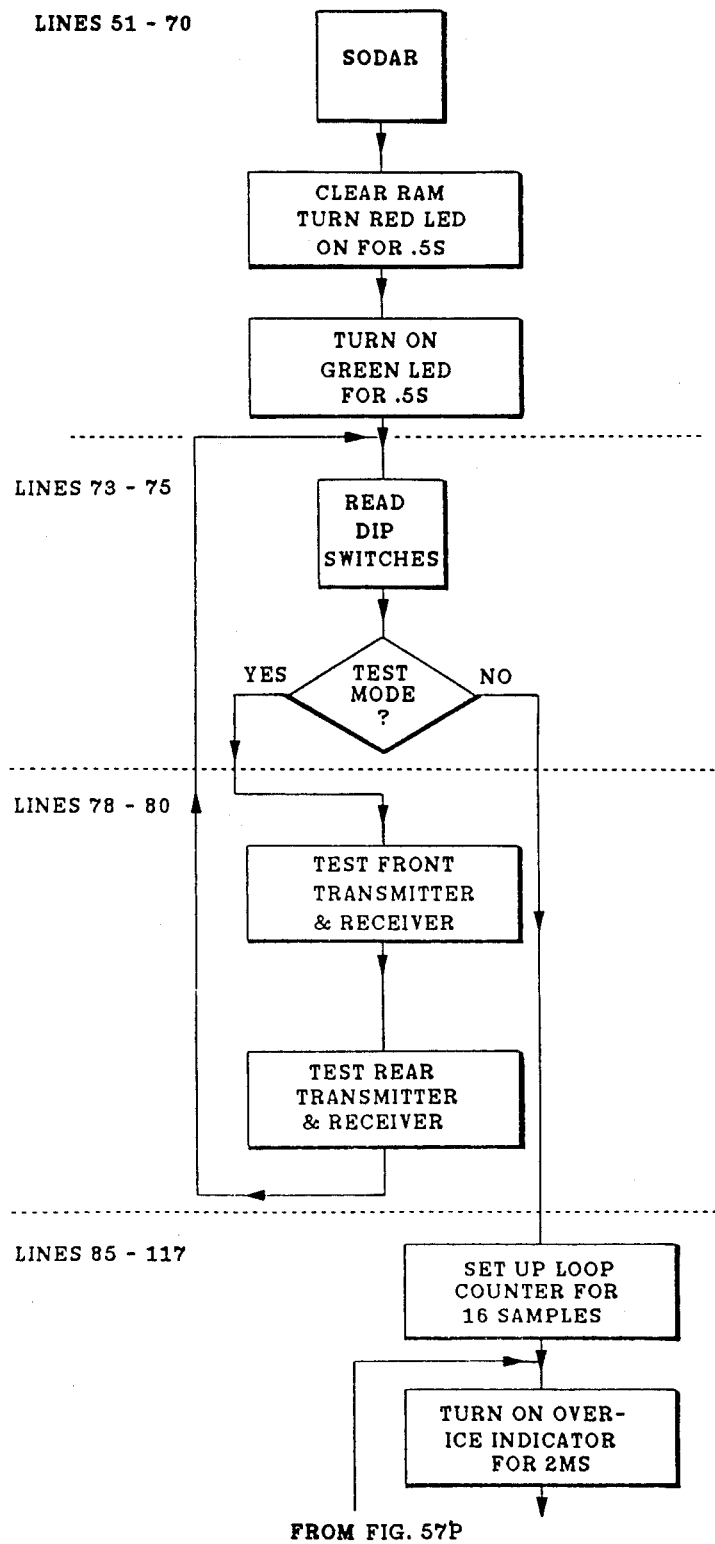
Figure 57P:
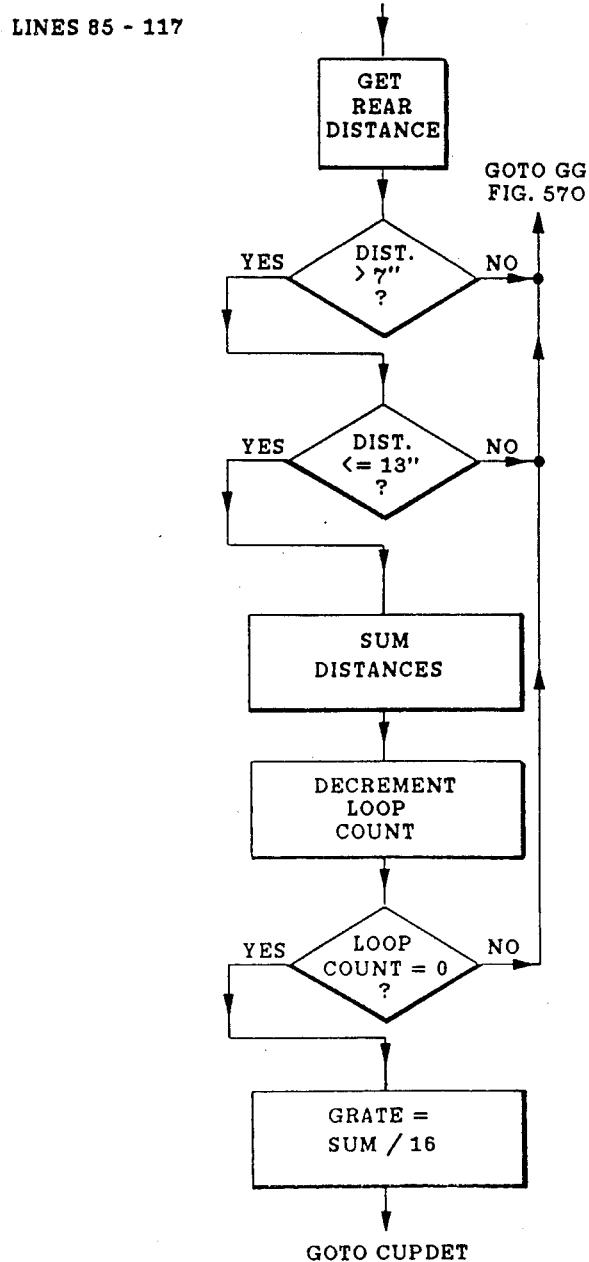
Figure 57Q:
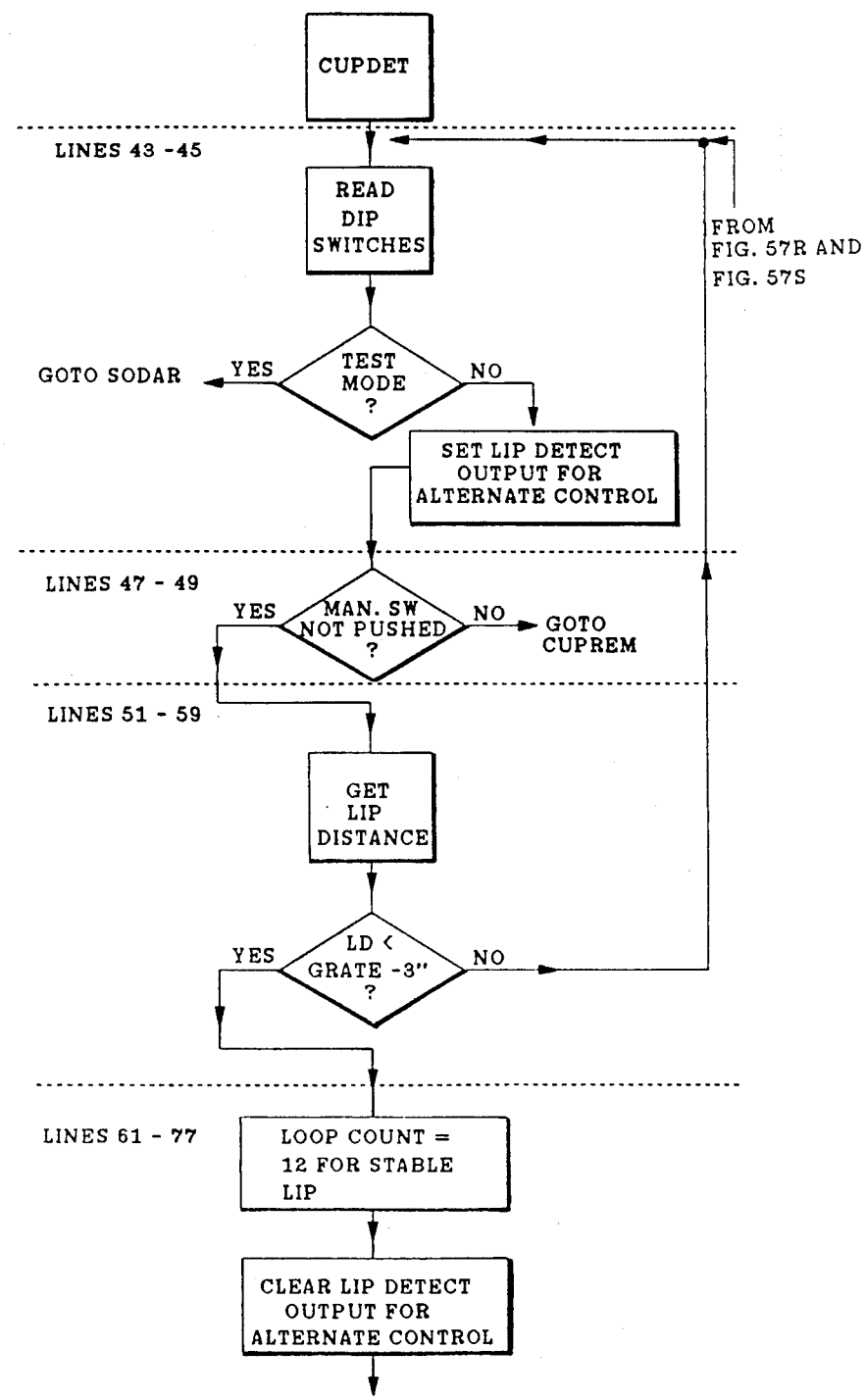
Figure 57R:
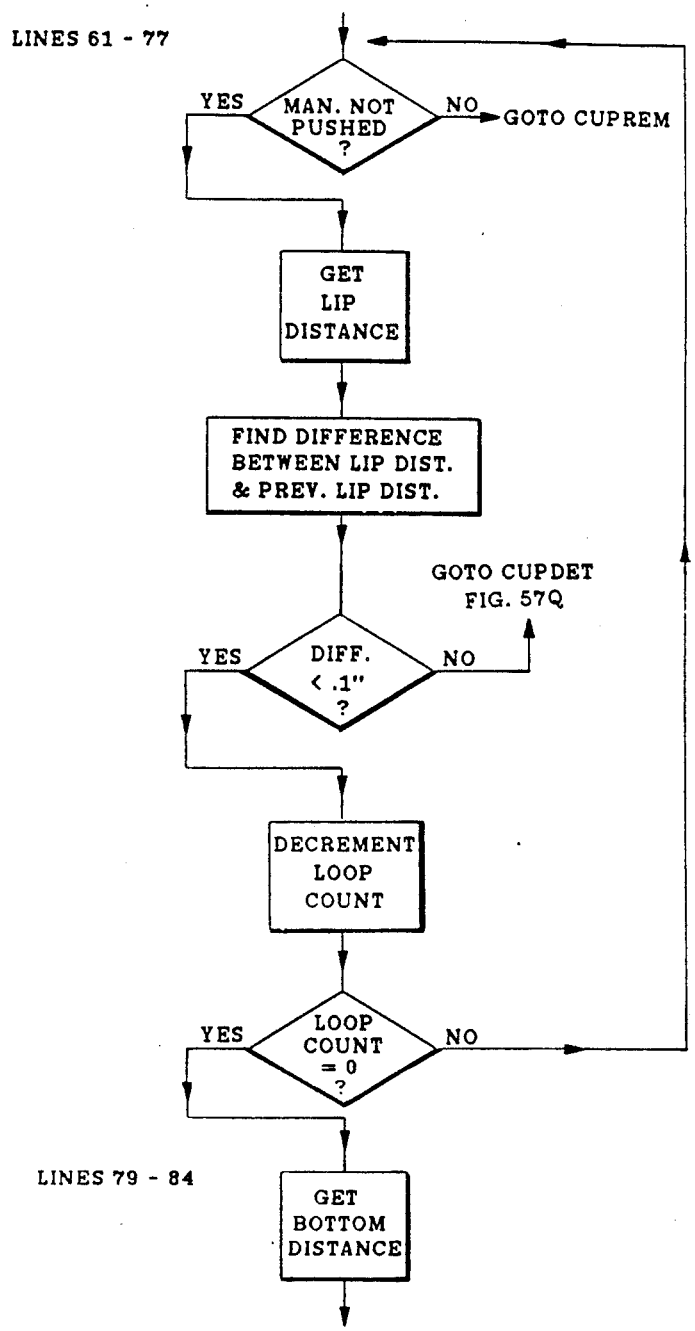
Figure 57S:
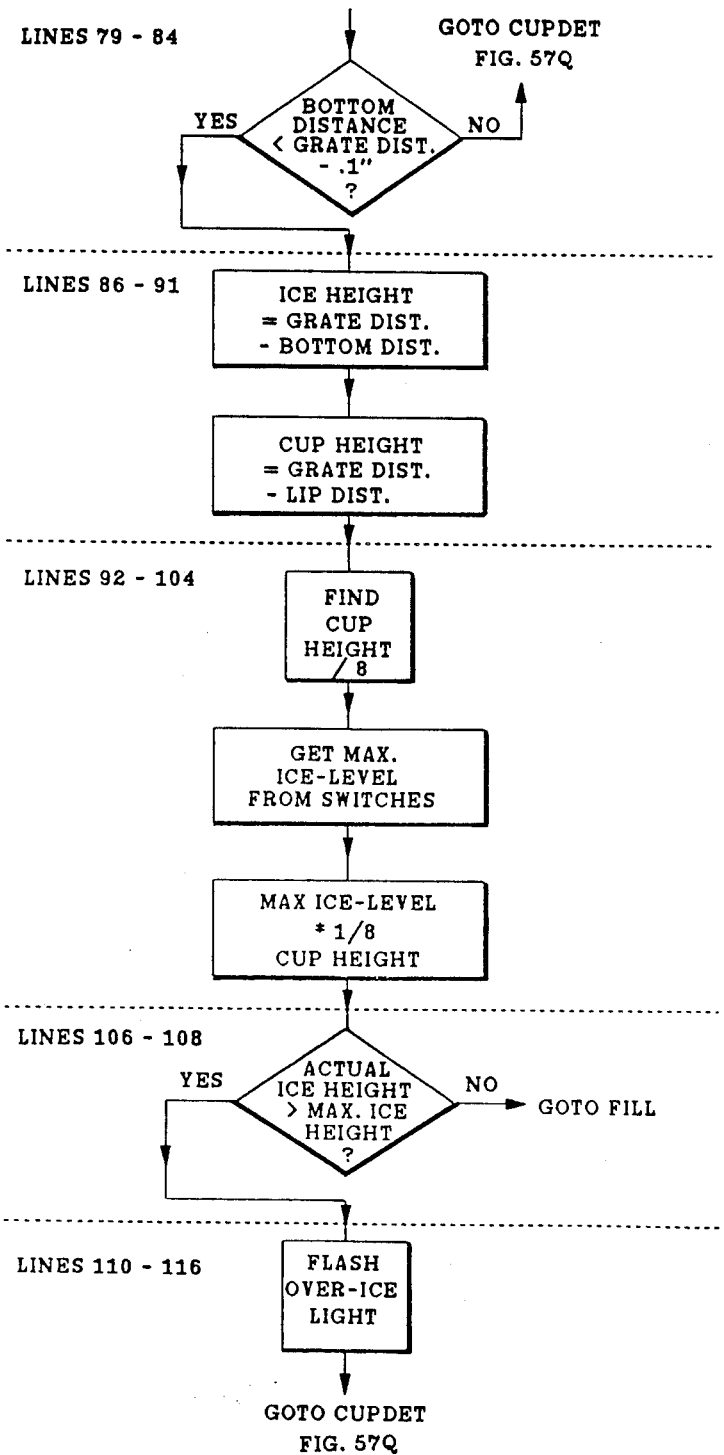
Figure 57T:
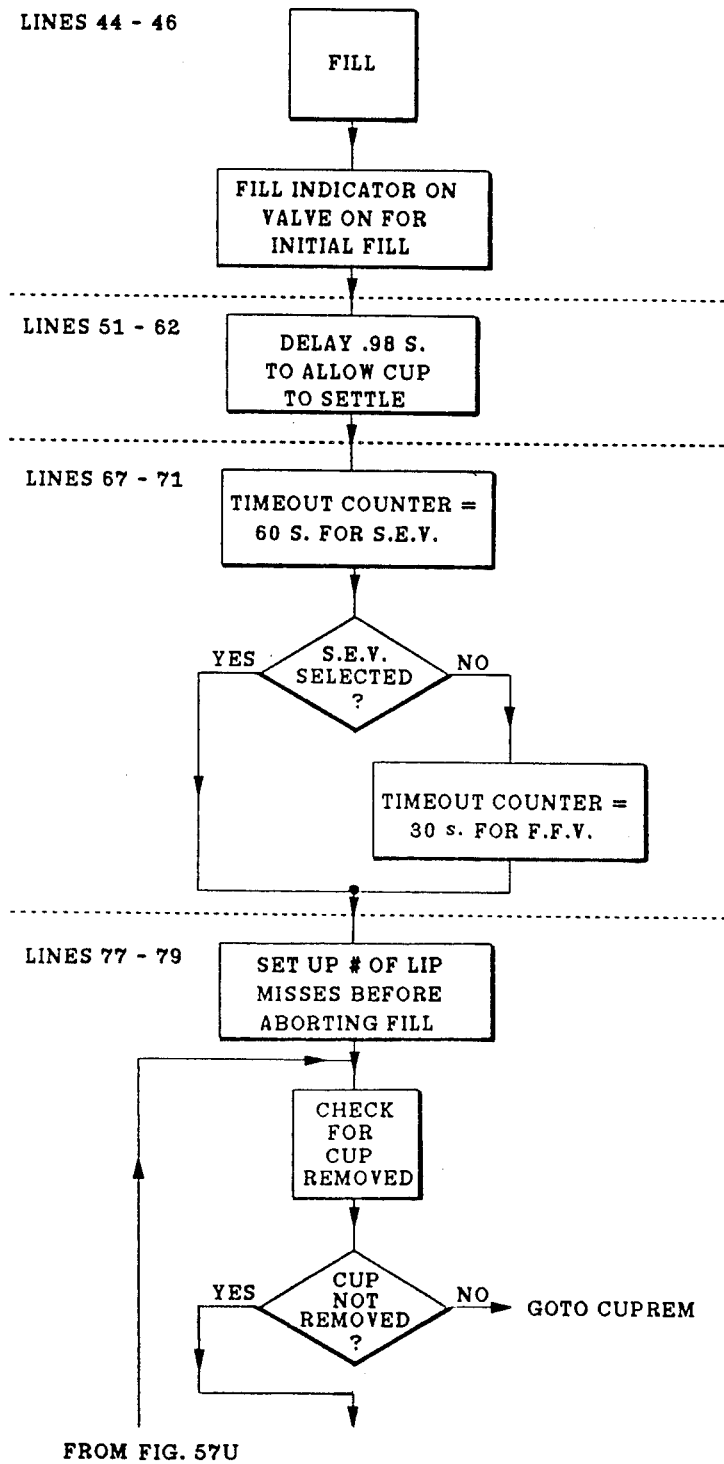
Figure 57U:
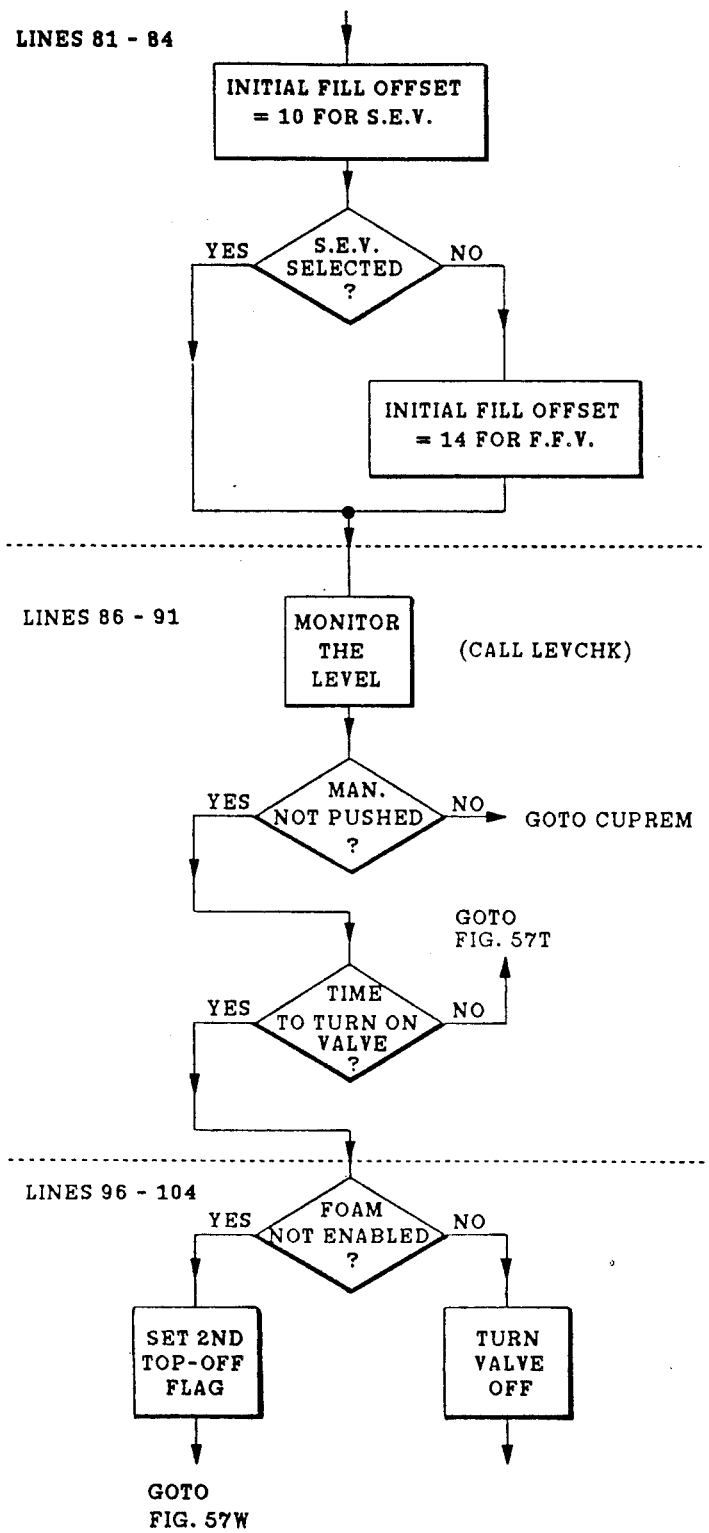
Figure 57V:
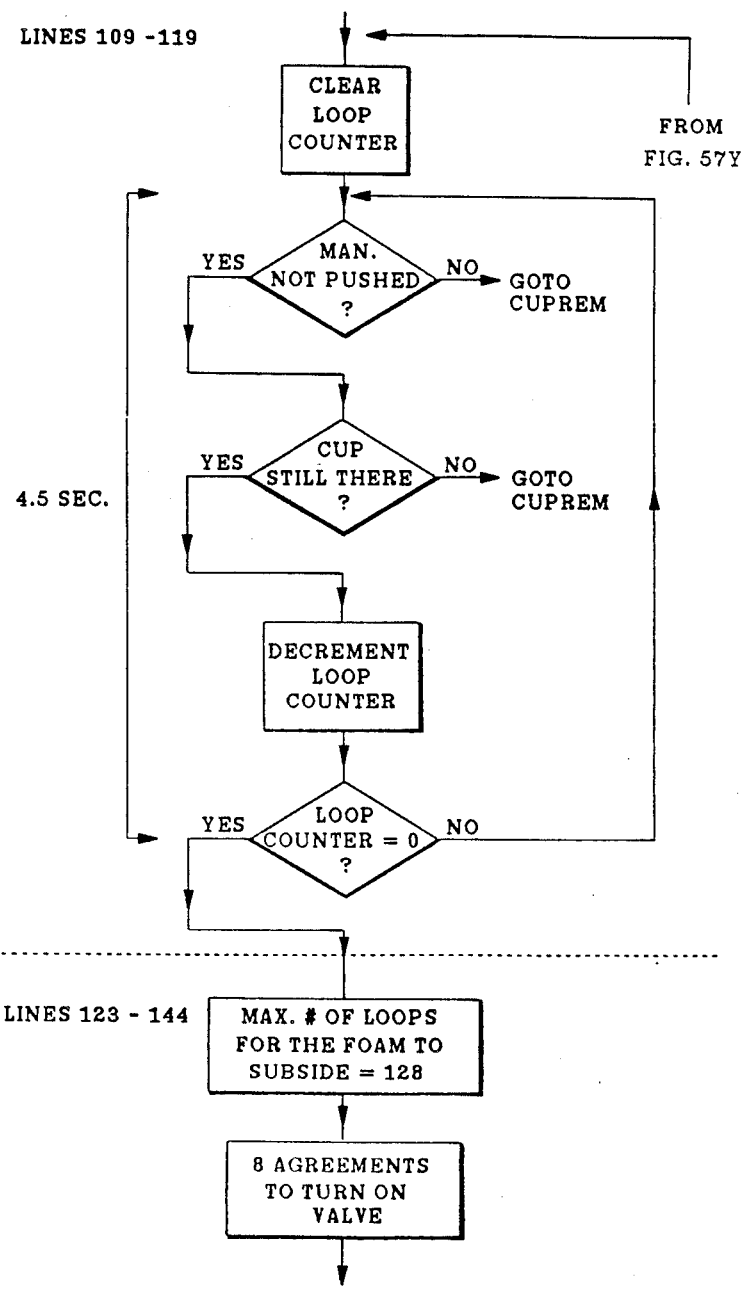
Figure 57W:
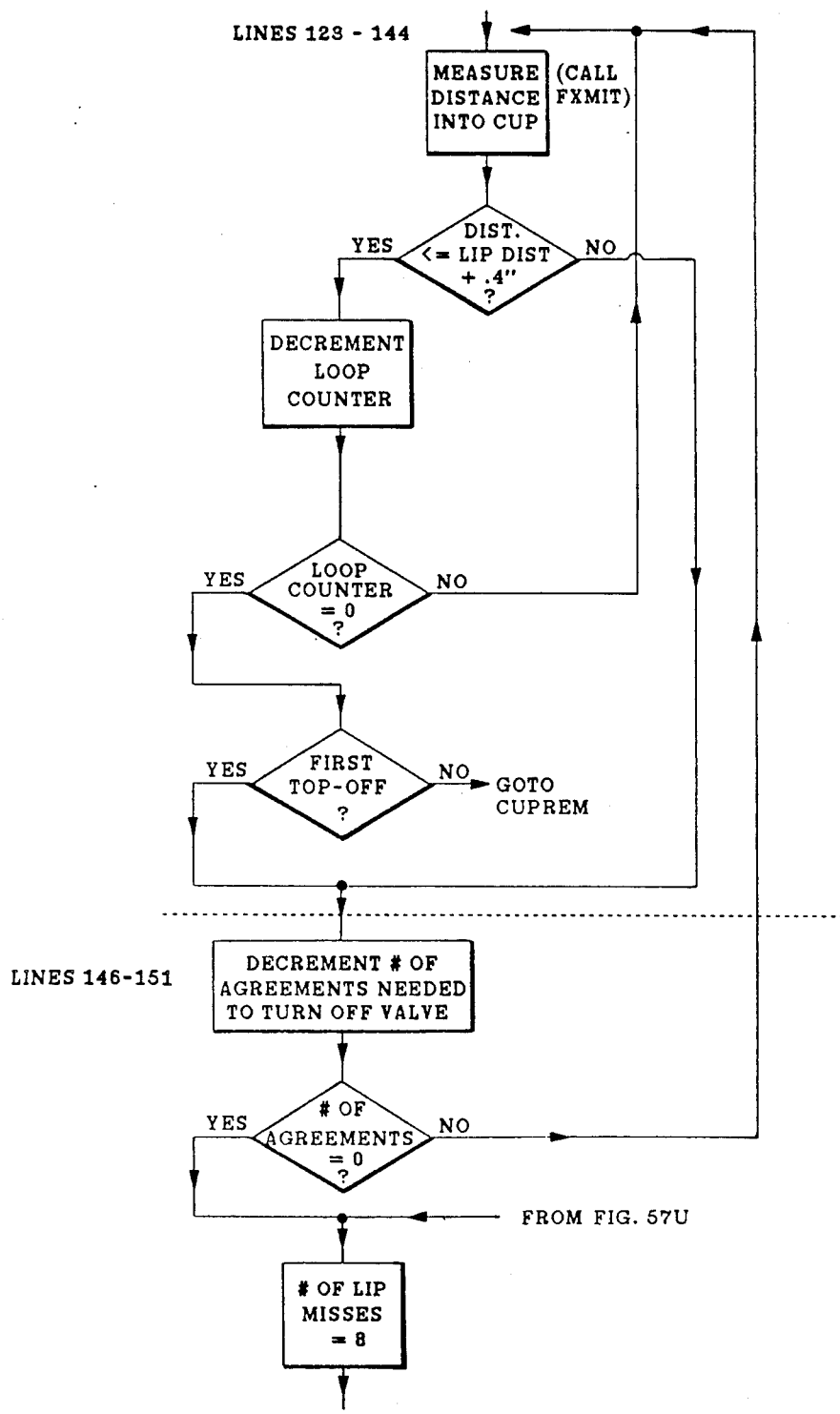
Figure 57Z:
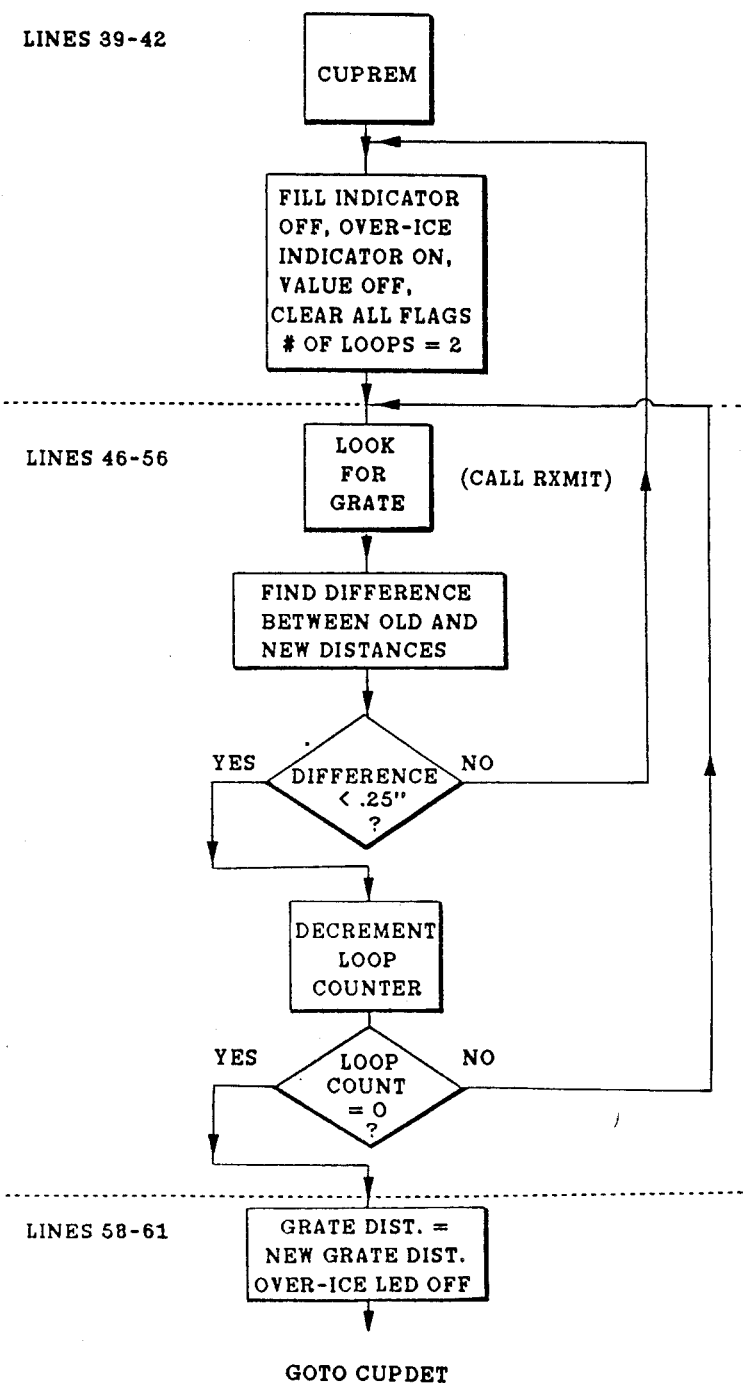

Briefly, FIGS. 47 and 48 show the transducer assembly as attached to a typical beverage dispenser valve, FIGS. 49 and 50 are electrical block diagrams of the electronics package, FIGS. 51–56 are electric schematic diagrams of the circuit components, and FIGS. 57A–57Z are flow charts of the software.

It is believed that it will be helpful to first describe some of the main differences between this third and preferred embodiment, and the previously described two embodiments. This third embodiment employs four crystals instead of two crystals. The four crystals are divided into pairs with each having a receiver and a transmitter. The front pair of crystals are used to detect the presence of a cup bottom or ice level. While the drink is pouring, the front crystals monitor the liquid level in the cup. Lenses and channelizer tubes are used on the front crystals to focus the ultrasonic beam and to minimize side lobes. Without the channelizer tubes, side lobes are more pronounced which cause echoes to be detected from the nozzle and from the front lip of the cup. Either of these echoes would prevent this system from pouring. By adding the channelizer tubes, the side lobes are minimized, allowing more latitude in cup placement.

The rear pair of crystals are used to detect the presence of a cup lip and to determine the distance to the grate. While a drink is pouring, the rear crystals periodically check for the presence of a cup. If the cup is removed, the rear crystals will detect the grate which causes this system to turn off the valve. The previously described embodiments had only one transmitter circuit to drive the one transmitter crystal. This new embodiment has two transmitter circuits, one for each transmitter crystal. By having two transmitters, the transmit periods can be different for the front and rear crystals. In the previously described embodiments, a flyback transmitter is used. This new embodiment uses a push-pull type transmitter. The push-pull type transmitter can deliver more transmit power to the crystals. The transducer housing has been modified in this new embodiment to accommodate the two new crystals and the channelizer tubes on the front crystals. The channelizer tubes can be removed for cleaning. The fill height is no longer fixed in this new embodiment. A potentiometer is provided to allow the target fill height to be adjusted.

Now that certain differences have been described, it is believed that a brief overview will be helpful before describing this embodiment in detail. The automatic filling system of this embodiment of the invention first determines the distance to the grate by transmitting a 100 microsecond plus from the rear transmitter. If sixteen measurements indicate the grate distance is between 7" and 13" then the average grate valve from the sixteen measurements is stored in RAM.

The next step is for the system to detect a cup. The system uses a 100 microsecond pulse, transmitted from the rear transmitter to look for a cup lip. A valid cup lip is any object detected by the rear crystals which is at least 3" above the grate. Twelve consecutive lip measurements within ±0.1" are required before the system goes on to the bottom detect routine.

To determine the presence of a cup bottom, this system uses a 25 microsecond pulse transmitted from the front transmitter. A valid cup bottom is any object detected by the front crystals which is at least 0.1" above the grate and is below the maximum ice level selected by dip switches on the circuit board. Once a valid bottom is detected, this system goes to the Fill Routine.

The Fill Routine turns on the valve. While the drink is pouring, this system monitors the presence of a cup lip using the rear crystals, and it monitors the level within the cup using the front crystals. When the liquid level in the cup has reached 0.5" of the lip and the dip switch on the circuit board is set for "foamy products", this system stops the valve and waits for the foam to subside. Up to two topoffs can occur if necessary. A topoff is initiated when the liquid level drops below 0.4" of the cup lip. If the dip switch on the circuit board is set for "non-foamy products", this system allows the valve to continue dispensing until the liquid level is equal to the preset target level.

This system has a fail safe timer which will override the normal control scheme and shut-off a fast flow valve (3 oz/sec) after 30 seconds or a standard flow valve (1.5 oz/sec) after 60 seconds.

The rear transmitter-receiver pair looks at just the grate and the lip, while the front transmitter-receiver pair looks at just the liquid level. The front beam is concentrated like a spotlight, while the rear beam is fan-shaped, i.e. it is narrow side to side but wide front to rear. The front beam has to go through a mist which requires more power, and the spotlight shape provides a beam of concentrated power over a smaller area. Since most losses are caused by the speeding of a beam, however, more power is used by the rear fan-shaped beam. The two pairs of transmitters and receivers of the present invention allow the system to look at two different areas at the same time and with differently shaped beams.

With reference now to the drawings, FIG. 47 shows a valve assembly 412, which can be any known valve assembly, for use on the dispenser 10 of FIG. 1. The automatic filling system of this preferred embodiment includes a transducer assembly 420 located on the bottom surface 422 of the valve assembly and behind the nozzle 424, and an electronics package.

The transducer assembly is shown in FIGS. 47 and 48, and includes a cup bottom and liquid level transmitter crystal 430, a cup bottom and liquid level receiver crystal 432, a lip and grate transmitter crystal 434, and a lip and grate receiver crystal 436.

FIG. 48 is a cross-sectional side view of the transducer assembly 420 through the crystals 432 and 436. The assembly 420 is basically the same as described above regarding the first two embodiments, and includes a plastic housing 440 filled with urethane foam 442. The crystals 430, 432, 434, and 436 are each positioned inside of a brass tube (such as tubes 444 and 446), and each have a plastic lens (such as lenses 433 and 437).

The electronics package will now be described first with reference to the electric block diagrams of FIGS. 49 and 50, and the schematic circuit diagrams of FIGS. 51–56, and then the software will be described with reference to the flow diagram of FIGS. 57A–57Z and the source code (Appendix A).

Referring to FIGS. 49–56, the electronics package is constructed of two double sided printed circuit boards approximately 2.5 by 3.7 inches housed in an ABS plastic enclosure. The block diagrams of FIGS. 49 and 50 of the system are related to the schematics of FIGS. 51–56 as follows:

1. The power supply 500, shown in FIGS. 49 and 51, uses 24 volts from the 50 VAC/transformer in the dispenser 10 of FIG. 1. The 24 volts AC is filtered by two 100 microhenry inductors and 0.1 microfarad capacitor to attenuate high frequency spikes on the 24 VAC line. The AC voltage is then rectified and filtered to supply an unregulated voltage "V" which has a nominal value of 25 Volts. A 39 Volt Zener, D3 is reverse biased across this voltage to provide surge protection. The 25 Volt supply is regulated down to 15 Volts for the receiver subsystem by a 78L15 3 terminal regulator. The 25 volt supply is also dropped to 20 volts with a Zener regulator for the transmitter supply. A stepdown switching power supply is utilized to provide the +5 volts for the microcomputer and logic. The supply uses an MC34063 control circuit and a 660 microhenry inductor to regulate the 25 VDC down to 5 VDC with an efficiency of about 80 percent.

2. The usual switch in the valve assembly 412 that energizes the two solenoids (the syrup end the carbonated water solenoids) is removed and replaced by a switch shown in FIG. 51. This is solid state switch (triac), ST04HA-2, which can be controlled either by the microcomputer through the optically coupled triac driver MOC3011, or by depressing the manual override switch described in paragraph number 12 below.

3. The Front end Rear receiver crystals 432 and 436 are made from a PZT 4 ceramic material but could be made from other variations available on the market. They are used as two separate receiver crystals that are switched electronically to allow the electronics to see the grate and cup lip from the rear crystal 436 and the cup bottom and fluid level from the front crystal 432. These crystals are coupled to the air with an acrylic plastic lens which also serves to shape the beam of the ultrasonic sound. The rear lens are angled toward the center of the valve 3.5 degrees and have a straight radius of 2 degrees as shown in FIG. 58. The lenses are attached to the crystals using a cement that has the same density as an acrylic lens so as not to reflect the sound waves back into the crystal. The crystals and lenses are then mounted in a polyurethane foam molded section that is inserted in a brass housing for electrical and accoustical isolation between the lenses. The brass housings, each containing a lens and crystal, are then mounted in another polyurethane foam block which inserts into the ABS transducer housing. The lenses have flanges that when mounted in the foam block properly positions the angles such that when the transmitted signal reflects back to the receiver crystal, the line will collect the most signal from the area to which the sound has been beamed. The front lens, as shown in FIG. 59, has a conical shape on the surface which is angled 3.5 degrees toward the center of the valve and has a 3.5 degree countersink in the face of the lens. The front lens also have a tube 510 approximately 0.5 inches long and ¼ inch in diameter that is also angled toward the center of the valve that channels the sound past the nozzle 424 so that there are no echoes to reflect from the nozzle back to the lens.

Figure 52:
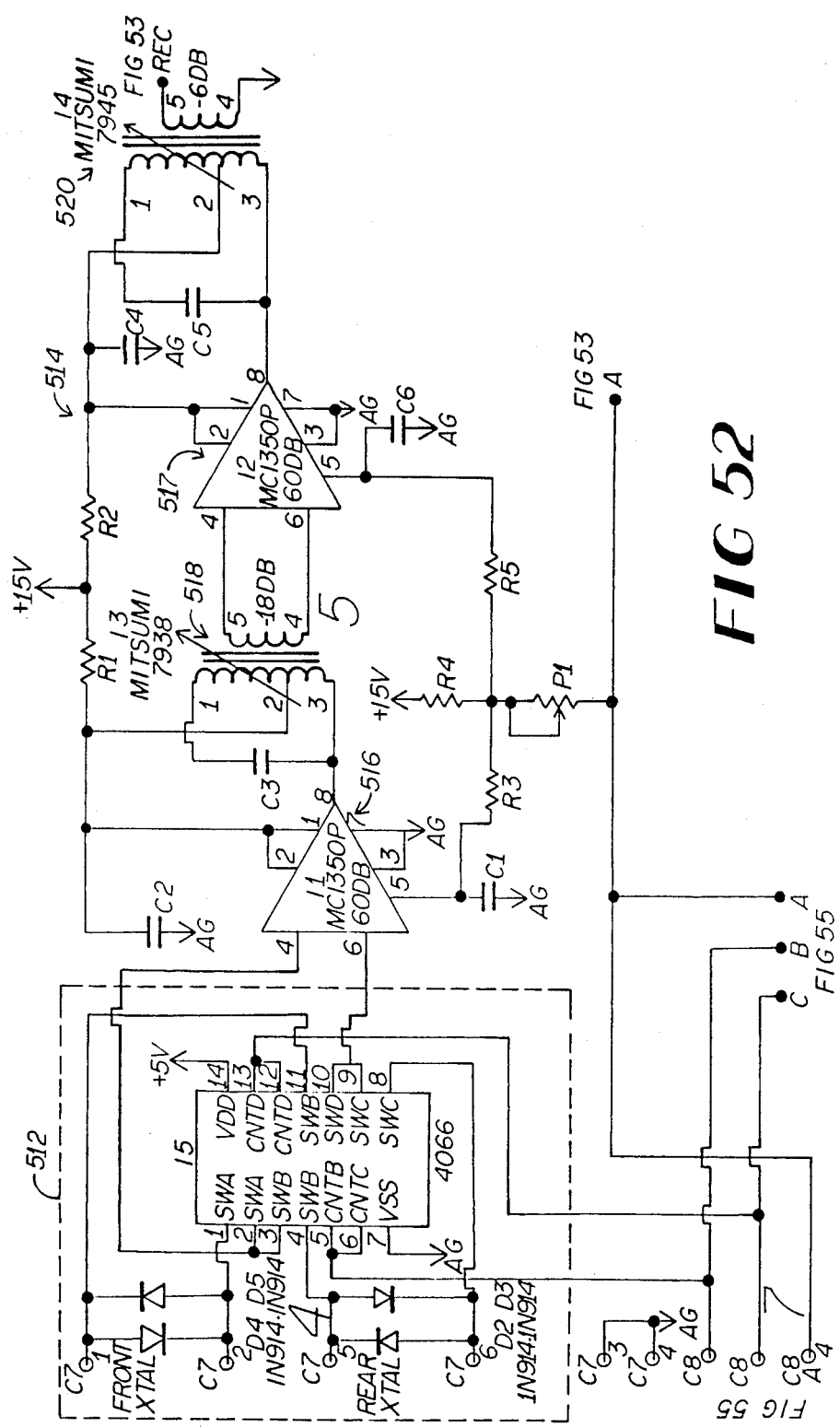
FIG. 52 is an electric schematic of the receiver shown in FIG. 50.

4. The analog multiplexer 512 is shown in FIG. 52, and uses a 4066 quad CMOS analog switch which allows the electrical signals from either of the two receiver crystals 432 or 436 to pass to the tuned amplifier. The analog inputs to the chip are protected from high voltage inputs by the 1N914 diodes. The digital inputs which select the crystal are the "B" and "C" lines directly from the microcomputer.

5. The receiver 514 is shown in FIG. 52 and has a maximum gain of 96 DB and is constructed with 2 MC1350P "I.F." amplifiers 516 and 517 that are connected through a tuned transformer 51B. A second tuned transformer 520 couples the amplified signal to the detector 522 shown in FIG. 53. The tuning transformers are tuned to a narrow band centered at 400 KHZ. The amplifiers have provision for gain control through Pin 5 of the MC1350P. By setting "A" line from the microcomputer high during the excitation phase of the transmission, the gain of the amplifiers is reduced to a minimum. When the excitation phase is over, the gain is returned to maximum. This keeps the amplifiers from saturating during the period of transmitter excitation and minimizes the effect of direct coupling of sound from the transmitter crystal to the receiver crystal.

6. The detector circuit 522 shown in FIG. 53 demodulates the 400 KHZ from the receiver to a DC analog signal, compares the amplitude with a fixed level and outputs a digital level to the microcomputer. The amplitude demodulator is special in that it can not only detect the envelope of the pulse but since it is a DC coupled detector, it has no offset shift due to pulse width variations. By having a balanced detector system, the temperature drift is very low. The level comparator uses one half of an LM393 voltage comparator and a resistive divider. The resistive divider is connected to the "A" line from the microcomputer. As described in paragraph 5 above, the "A" line is set high during the period of transmitter excitation. When line "A" is at 5 volts, the level to which the analog signal is compared to is raised from approximately 2 volts DC to approximately 6 volts DC which insures that no digital signals will reach the microcomputer during the excitation phase of the transmitter.

Figure 53:
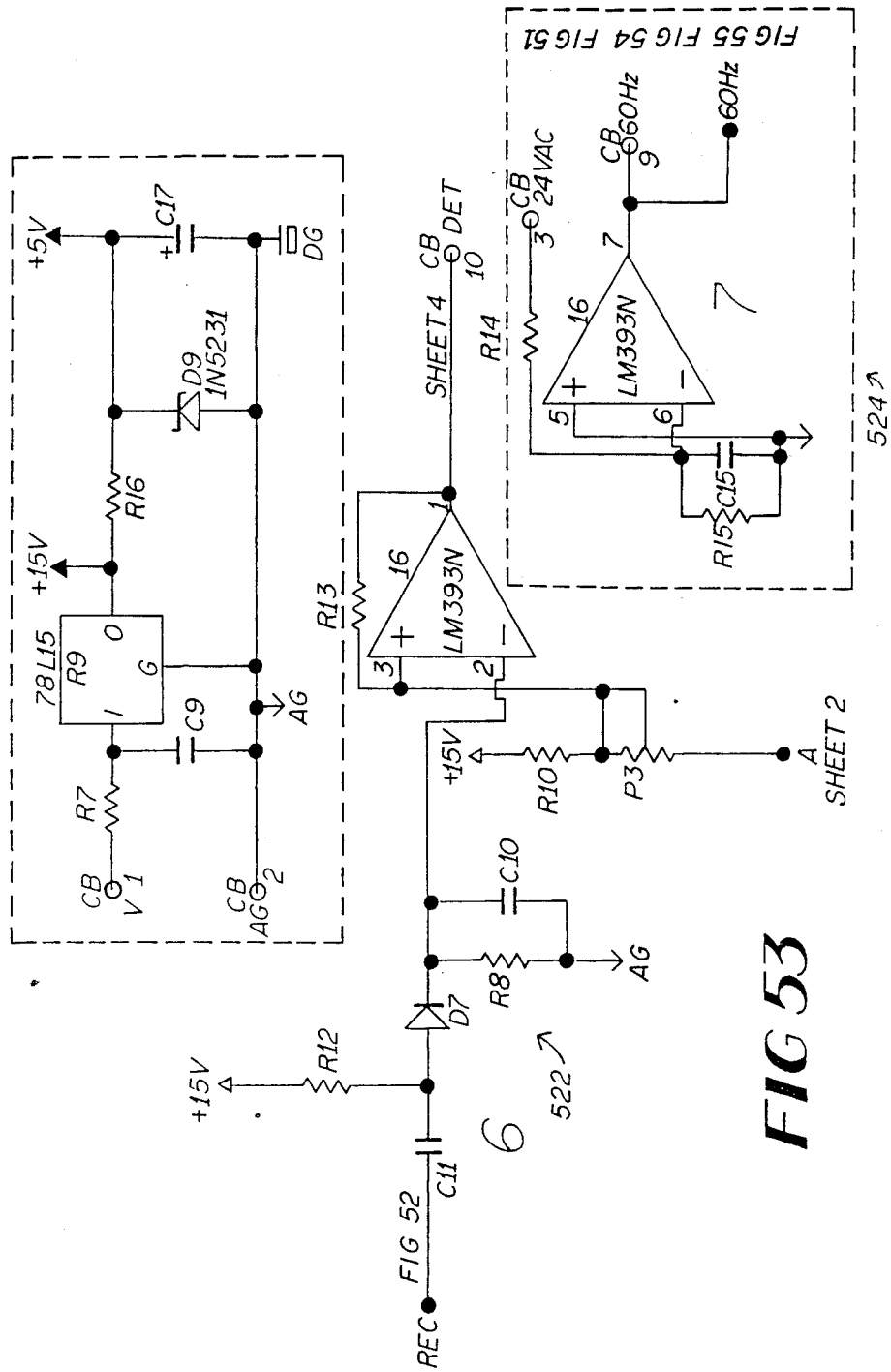
FIG. 53 is an electric schematic of the detector. shown in FIG. 50.

7. The 60 hertz detector 524 shown in FIG. 53 is constructed using one half of an LM393 voltage comparator. 24 VAC is attenuated and compared to ground. The output is a 60 HZ ZERO TO 5 volts square wave. This waveform is the basis for the timing of the transmitters. A selector switch described in paragraph 15 below tells the microcomputer to transmit on either the high portion of the waveform or on the low portion of the waveform. This feature will allow two closely spaced systems to operate without interference.

Figure 54A:
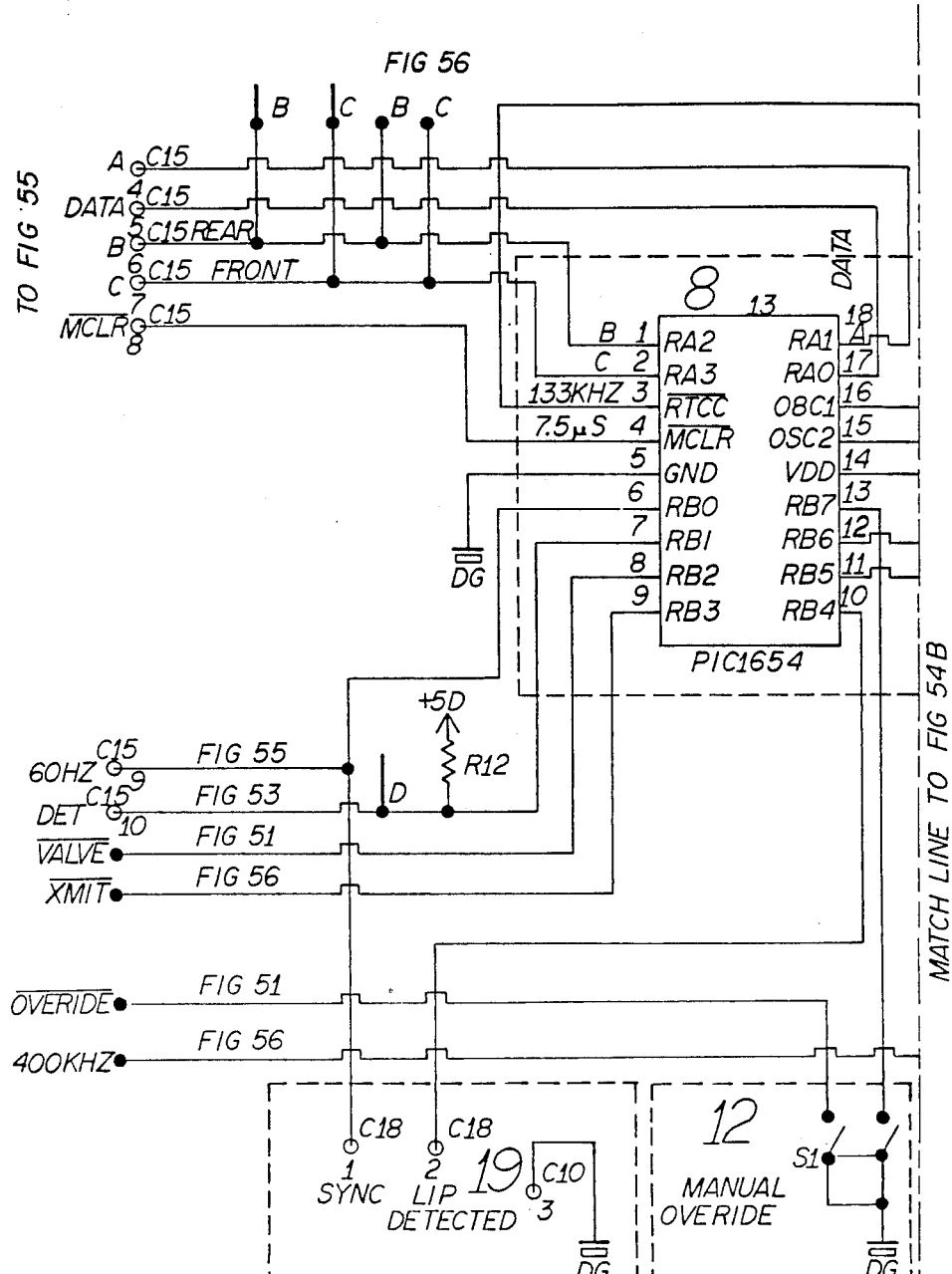
FIG. 54 is an electric schematic of the microcomputer shown in FIG. 49.
Figure 54B:
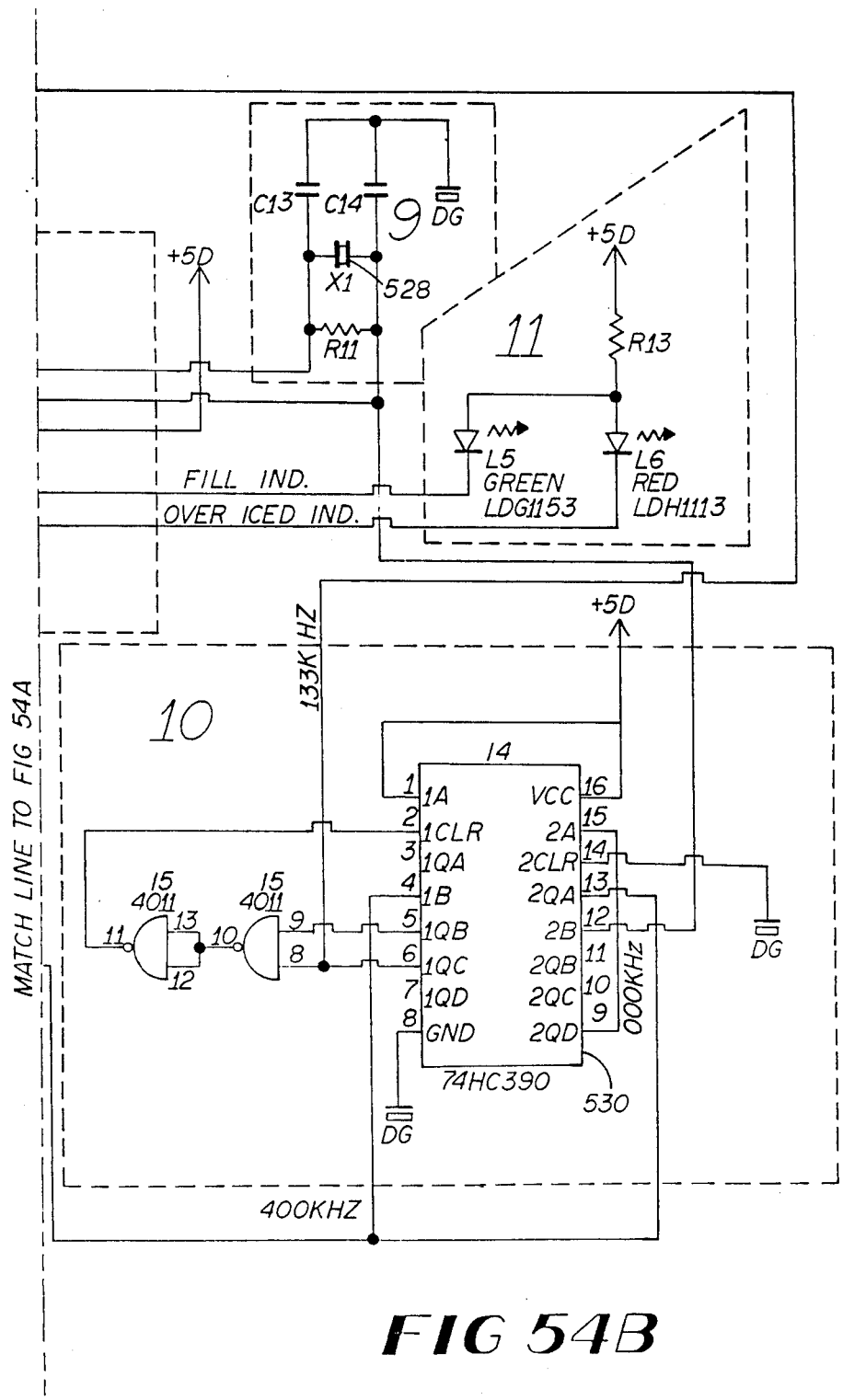

8. The microcomputer 526 shown in FIG. 54 is a General Instrument's PIC-1654 and contains the intelligence and control functions of the entire system. It communicates to the rest of the system through 12 I/O pins. It also contains the oscillator circuit, the master clear circuit, and the real time clock counter input.

9. The 4 Mhz crystal 528 and other passive components form the feedback network for the oscillator in the microcomputer 526 and is shown in FIG. 54.

10. The 74Hc390 counter/divider chip 530 shown in FIG. 54 is used to divide the 4 Mhz into 400 kilohertz and 133 kilohertz. The 400 kilohertz is used in the transmitter as the frequency of transmission and the 133 kilohertz is input to the real time clock counter input of the microcomputer. One period of the 133 kilohertz signal corresponds to the time it takes for sound to travel to and from an object 1/20th of an inch.

11. The front panel indicator lights 532 and 534 shown in FIG. 54 consist of one red LED and one green LED. The green LED is labelled fill and is illuminated during the filling process. The red LED is labelled over-ice/cup remove, and is illuminated when the ice level is detected to be above the allowable ice level (user selected by DIP switches described in paragraph 15 below. The red LED also illuminates at the end of a filling cycle when the cup (not shown) is ready to be removed.

Figure 55:
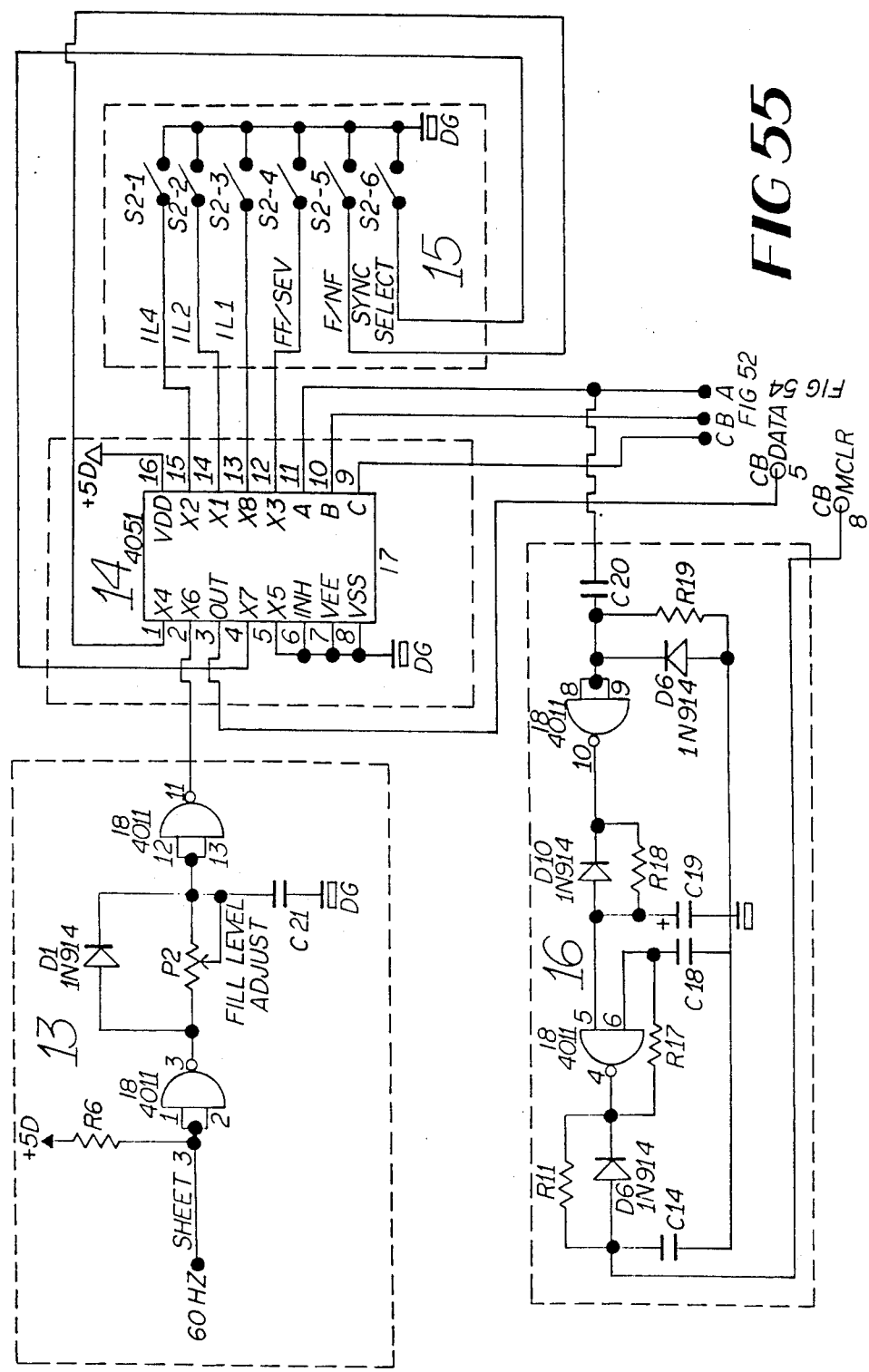
FIG. 55 is an electric schematic of the digital multiplexer watch dog timer shown in FIG. 50.
Figure 56:
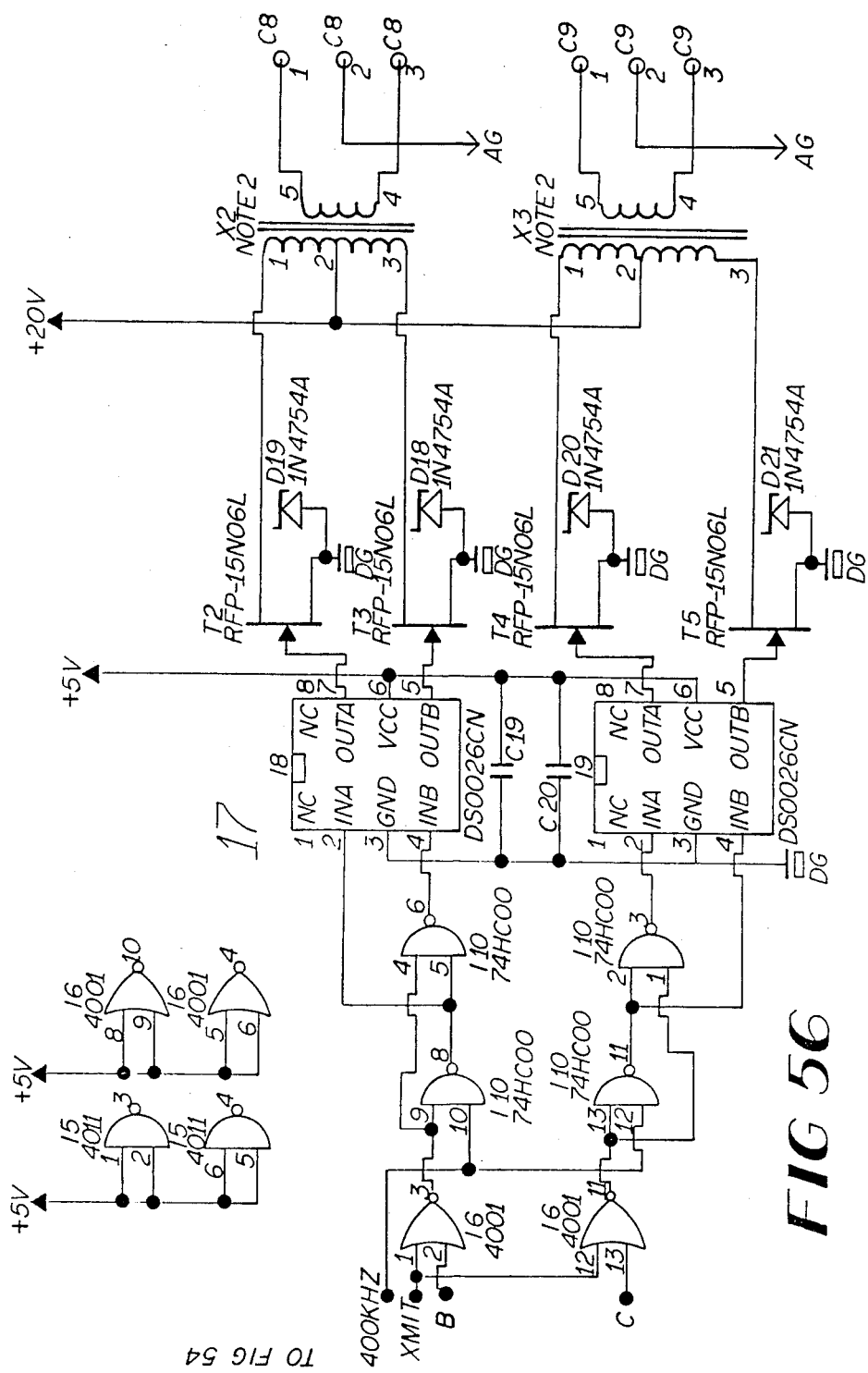
FIG. 56 is an electric schematic of the transmitter shown in FIG. 49.

12. The front panel manual override switch 536 shown in FIG. 55 is a two pole pushbutton switch. One pole is connected directly to the gate circuit of the valve control triac as described in paragraph 2 above which allows the user to directly control the actuation of the two solenoid valves in the valve assembly 412. The other pole is used as an input to the microcomputer 526 and notifies the microcomputer that the user has actuated the valve 412, so the microcomputer knows it is not in control.

13. The final fill level adjustment circuit shown in FIG. 55 allows the user to adjust the final drink level in the cup. The circuit itself is a variable edge delay circuit which uses 2 CMOS logic gates from a 4011 I.C. as buffers and a potentiometer, capacitor, and diode network to delay the rising edge of the 60 hertz square wave input. The output of the final fill level adjustment is input to the Cmos digital multiplexer described in paragraph 14 below.

14. The digital multiplexer shown in FIG. 55 is a Cmos analog switch (4051) which is configured as a single pole 8 position switch. The "A" "B" and "C" lines from the microcomputer 526 select which of the 8 inputs will be connected to the "Data" line of the microcomputer.

15. The six individual switches shown in FIG. 55 and referred to as a dip-switch in this application are to enable the user to configure the controller for proper operation under different operating conditions. Three of the switches are used to set a maximum ice level allowed setting which can be from $\frac{1}{8}$ to $\frac{7}{8}$ of the cup height. When these switches are off, the manufacturing test is enabled. One switch selects between two different flow rates. One switch selects either a foaming drink routine or a non-foaming drink routine. The last switch is the sync select switch that selects which half of the 60 hertz square wave will be used for transmitting and receiving. As described in paragraph 7 above, this feature allows two systems to operate in close proximity.

16. The watch dog timer circuit showing in FIG. 55 provides power on reset for the microcomputer. 526 and monitors the operation, forcing the microcomputer to reset if it detects the "A" line not changing "states" for as long as 8 seconds. The circuit itself consists of an edge detector, a retriggerable timer, and a gated oscillator. The edge detector differentiates the rising edge of the "A" line from the microcomputer. The "A" line in normal operation will have approximately 120 rising edges per second. The output of the differentiator is buffered with a Cmos logic gate (4011) whose output retriggers the retriggerable timer. If the differentiator does not receive rising edges from the "A" line, then the retriggerable timer times out Within 8 seconds. When the retriggerable timer times out it enables the gate on the gated oscillator, which tries to reset the microcomputer until the "A" line again starts changing "states."

17. The transmitter logic shown in FIG. 56 and the power amp is the circuitry which inputs the 5 volt logic levels from the microcomputer and outputs the approximately 1000 volt peak 400 kilohertz. The transmitter logic allows the microcomputer to have direct control over the pulse link of 400 kilohertz to be transmitted and which crystal is going to be used to transmit. The two CMOS Nor-gates (4001) with the B line and C line and the transmit line as input allows the microcomputer to select which crystal is going to transmit. The output of the Nor-gate is input for two Nan-gates (74hc00) along with the 400 kilohertz square wave. The output of the two Nan-gates 400 kilohertz modulated pulses which are buffered by the buffered chip (ds0026cn) which provides the drive for the power mosfets (RFP-15N06L). The zener diodes across the power amp protect the power amp from reverse voltage and overvoltage. Each pair of power amps drives a ferrite transformer in a class B push-pull configuration. The output winding is directly attached to the ceramic piezzo crystals.

18. The transmitter crystal is the same configuration as the receiver crystal except that they are mounted on the opposite side, but the crystals and lenses are interchangeable with the front receiver or the rear receiver respectively. The removable section from the front lens housing that contains the tubes is removable for easy cleaning of the lens itself. The front crystal lens is shown in FIG. 59.

19. The alternate control connector shown in FIG. 54 allows more than one control to operate a single valve. The lip detected output is normally high and when the microcomputer detects a lip, the lip detected output would go low to notify the other control that it may be ready to initiate a fill operation. The sync input would normally be a high impedance input that would not affect operation. When the sync input is changed to a low impedance, the 60 hertz square wave that the micro is using to synchronize transmissions would be held low, inhibiting transmissions until the high impedance state returns, allowing the 60 hertz square wave to again synchronize transmission. This feature along with additional Logic will allow more than one transducer assembly and electronics package to control a single valve.

The software used in this preferred embodiment of the invention will now be described with reference to the flow chart in FIGS. 57A-57Z and the source code in Appendix A. To aid in this description the flow chart is divided by dashed lines into areas with certain numerals assigned thereto, which numerals correspond to the numbered lines in the source code (Appendix A).

The single chip microcomputer 526 is a General Instrument PIC 1654. Some notable characteristics of the microcomputer are:
A. 512 program steps
B. 32 bytes of RAM
C. All instructions execute in 2 or 4 microseconds
D. All sub routines must begin in lower half of memory.
E It has an eight bit clock counter.
F. When master clear is pulled low and then released high, the program counter is set to the last program location (511).
G. The architecture includes a two level stack.

The program consists of 4 main program routines and 8 subroutines.

The 4 main routines are entitled SODA, CUPDET, FILL, AND CUPREM.

In the accompanying program listings, each of the main program routines have a separate listing. Each routine and subroutine have their separate set of line numbers starting with 1.

The subroutines are all contained in 2 program listings. The transmitter and receiver subroutine is entitled SODAR 86 TRANSMITTER.

The other 7 subroutines are contained in the listing entitled MISCELLANEOUS SUBROUTINES. The accompanying source code (Appendix A) is sequenced in the same manner as this description.

1. Lines 1 through 29 contain the register definitions for the transmit subroutine.

The transmit subroutine has 2 entry points, FXMIT. and RXMIT. The FXMIT entry point selects the front crystals and a 25 microsecond transmit pulse width. The RXMIT entry point selects the rear crystal and a 100 microsecond transmit pulse width. Line numbers 34 through 43 contain these entry points and prepare the hardware for transmission.

Line 44 tests the position of the sync switch to determine whether to transmit during the high or low portion of the 60 hertz square wave.

Line 48 through 63 looks for the low to high transition of the 60 hertz sync input.

Lines 66 through 79 have the same function but look for the high to low transition.

Lines 82 through 89 transmit either a 25 microsecond or 100 microsecond pulse width of 400 kilohertz depending on the entry point.

Lines 92 through 100 allow the microcomputer to ignore any echoes less than 0.8 from the crystal face.

Lines 102 through 117 capture the elapsed time until the leading edge of the first echo appears.

Lines 119 through 132 guarantee that the microcomputer will not transmit again until 4 milliseconds after the first transmit.

Line 134 through 143 check to see if the distance received was the first sample or the second sample. If it is the first sample, then it stores the distance in a temporary register and goes back to line 82 to transmit again for the second sample.

Lines 147 through 168 compares the two distances. If the distances vary by more than 0.4, then two more samples are obtained by going back to the entry point of either subroutine FXMIT or RXMIT. If the samples do agree within 0.4 of an inch, then they are averaged and the program returns to the calling routine.

The following subroutines are contained in miscellaneous subroutines listings.

2. The MUX subroutine controls the digital multiplexer through the A, B, and C lines and reads the selected input on the Data line.

Lines 1 through 49 contain register definitions and program label definitions.

Lines 55 through 71 read the positions of the dip switch into a register called SW.

Lines 73 through 79 check the ice level switches for an "all off" condition which is the position for the manufacturing test.

3. The WAIT 2 subroutine, lines 83 through 88, delays for 2 milliseconds and then returns to the calling routine.
4. The subroutine DIFF, lines 94 through 99, calculates the absolute value of the difference of two numbers.
5. The TIMOUT subroutine lines checks to see if the valve assembly 412 has been longer than 60 seconds for standard flow valve or 30 seconds for a fast flow valve. If it has, then the valve is turned off and the FILL and OVER ICE indicator alternate flashing.

Lines 104 through 107 decrement the TIMOUT counter and check for zero.

Lines 112 through 128 turn the solenoid off and alternately flash the OVER ICE indicator and the FILL indicator.

6. The CUPCHK subroutine checks during the filling process to see that the cup has not been removed.

Lines 132 through 153 use the rear transmitter to look for the grate. If the distance is within ¼ inch of the grate distance, then the "Cup Removed" flag is returned to the calling subroutine.

Lines 156 through 172 are not being used at this time. The LEVCHK subroutine monitors the liquid/foam level during the filling process. The calling routine sends the distance below the lip distance that the valve should turn off.

7. Lines 176 through 203 uses the distance returned from the FXMIT subroutine to decide whether to send a flag back to the calling routine to turn the valve off.
8. The FFLEV subroutine is called to read the variable final fill level.

Lines 210 through 236 measure the time between the rising edge of the 60 hertz waveform and the rising edge of the final fill level waveform through the digital multiplexer.

9. This time is scaled for a 0 to 2 inch offset. The main routine "Coke SODAR Project" performs initialization of the microcomputer, checks for the manufacturing test mode, and then obtains the initial grate distance before going to the cup detection routine.

Lines 1 through 35 contain register and program label definition.

Line 48 is the start vector which contains the first instruction executed when the system is reset.

Lies 51 through 64 is one second power up delay which allows the power supplies to stabilize before transmission begins.

Lines 66 through 70 clears all of the RAM registers.

Lines 73 through 75 read the configuration switches and check for the test mode.

Lines 78 through 80 are the manufacturing test routine.

Lines 85 through 117 obtain the initial grate value. The RXMIT subroutine is used to obtain distances. The distances are checked for being between 7 inches and 13 inches from the crystal. Any distance not between 7 and 13 inches from the crystal. Any distance not between 7 and 13 inches flashes the OVERICE indicator and ignores valve. 16 acceptable samples of the grate are averaged and then the program exits to the cup detection routine.

10. The CUPDET routine is the cup detection routine. This routine has a specific set of criteria that must be satisfied before the routine exits to the FILL routine. First the routine uses the RXMIT subroutine to look at the lip signal. The lip signal must be stable and within the distance of a legitimate lip signal. Then the routine uses the FXMIT subroutine to look inside the cup at the cup bottom or the ice level is present. The routine then recalls the maximum ice level from the dip switches and calculates the maximum ice level for that particular cup. If the ice level is greater than the maximum ice level allowed then the maximum ice level allowed then the OVERICE indicator flashes and the CUPDET routine begins again. If the actual ice level is less than the maximum ice selected by the dipswitch, then the routine exits to the FILL routine.

Lines 1 through 38 contain register and program label definitions.

Lines 43 through 45 read the dip switches by calling the subroutine MUX and tests for the manufacturing test mode. If the test mode is input, then the program branches back to the beginning of the SODAR initialization routine.

Lines 47 through 49 check for the manual override switch being pressed. If the switch is pressed then the program branches to the cup removal routine.

Lines 51 through 77 use the RXMIT subroutine to look for a stable lip in the following sequence:

Lines 51 through 59 check to see that the lip is at least 3 inches above the grate.

Lines 61 through 77 make sure that the lip distance is stable by having to see 12 samples in a row that are within 0.1 inch of each other.

Lines 79 through 84 use the subroutine FXMIT to look down into the cup to get the cup bottom distance or ice level. This also determines that the bottom of the cup is at least 0.1 inches above the grate.

Lines 86 through 91 calculate the cup height by subtracting the lip distance from the grate distance.

Lines 92 through 104 divide the cup height by 8 and multiplies the dividend by the maximum ice level switch inputs.

Lines 106 through 108 determine whether the actual ice height is greater than the maximum ice height selected by the dip switches. If the actual ice height is greater than selected, then lines 110 through 116 flash the red OVERICE indicator and branch to the beginning of the cup detection routine. If the actual ice height is less than the maximum ice height, then the routine exits to the FILL routine.

11. The FILL routine handles either foamy product or non foamy product and a fast flow or standard flow. These options are set in the dip switch. The FILL routine first turns the FILL indicator and the solenoid valves in the valve assembly 412 on. It then waits for one second before monitoring the liquid level. The level is then monitored using the LEVCHK subroutine until the initial FILL level for that particular type of valve assembly is reached. The routine then checks to see whether foamy or non foamy product is enabled. If non foamy is selected the valve is not turned off and the final topoff begins. If foamy product is enabled, then the valve is turned off and the program waits for 5 seconds before monitoring the foam level. When the foam level drops below 0.4 below the Lip, the first of two possible topoffs begin, separated by additional time to allow the foam to subside. When the final fill level is reached the program exits to the cup removal routine. Periodically during the entire fill routine the CUPCHK subroutine is called to ensure that the cup has not been removed.

Lines 1 through 40 contain register and program label definitions.

Lines 44 through 46 turn both the fill indicator and the valve on.

Lines 51 through 62 provide a 1 second delay while monitoring the manual pushbutton switch. This allows for initial splash and cup movement without aborting the fill.

Lines 67 through 71 set up the respective maximum "valve on" times for the standard (SEV) or fast flow valve.

Lines 74 through 91 provide the control for the initial fill in the following sequence:

Lines 77 through 79 use the subroutine CUPCHK to check for the cup having been removed. If the cup has been removed, the program branches to the cup removal routine.

Lines 81 through 84 select the distance below the lip for the initial fill.

Lines 86 through 91 use the LEVCHK subroutine to check if the manual switch has been depressed or if the liquid level is at or above the initial fill level.

Lines 96 through 104 first check the configuration switch to see if foamy product is enabled. If foamy product is not enabled, the final top off flag is set and the program branches to the top of routine. If foamy product is enabled, the valve is turned off.

Lines 109 through 119 are used in the first and second top off and provide a delay of 4.5 seconds, allowing the foam to finish rising and begin to fall. The routine checks for the manual switch being depressed. If the manual switch is depressed the program branches to the cup removal routine.

Lines 123 through 144 are also used in the first and the second top off routine. This routine uses the FXMIT subroutine to monitor the foam level in the cup. There are 3 possible exits from this routine.

(a) Before and after the first top off if the foam level falls below 0.4 inches below the lip the routine branches to the top off routine.
  (b) Before the first top off begins, if approximately 10 seconds passes and the foam level is not below 0.4 inches below the lip, then the program branches to the top off routine.
  (c) If after the first top off routine, approximately 10 seconds has passed and the foam level has not fallen below 0.4 inches below the lip, then the program branches to the cup removal routine.

Lines 146 through 167 are the top off routines for the first and second top off in the following sequence:

Lines 146 through 151 use the CUPCHK subroutine to ensure that the cup has not been removed. If the cup has been removed the program branches to the cup removal routine.

Lines 146 through 167 are the top off routines for the first and second top off in the following sequence:

Lines 146 through 151 use the CUPCHK subroutine to ensure that the cup has not been removed. If the cup has been removed the program branches to the cup removal routine.

Line 153 calls the Final Fill Level (FFLEV) subroutine which returns with the "Final Fill Level" distance below the lip.

Lines 155 through 161 monitor the liquid level in the cup. The LEVCHK subroutine is called and the return flags are checked to see if the manual switch has been depressed or if the fill level is at or above the final fill level.

Lines 163 through 167 turn the valve off when the liquid level reaches or exceeds the final fill level. If only one top off has occurred, the program branches back to line 109 to wait for the foam to fall. If the second top off has taken place the program branches to the cup removal routine.

12. The Cup Removal Routine (CUPREM) waits until the cup has been removed and then branches back to the cup detection routine. Lines 1 through 35 contain register and program label definitions.

Lines 39 through 42 turn the Fill indicator off turn the OVERICE/"Cup Remove" indicator on, turn the valve off, and clears all the flags.

Lines 46 through 56 check to see if the cup has been removed. This routine calls the RXMIT subroutine and checks for a distance within a quarter inch of the stored grate distance. If the measured distance is within a quarter inch of the stored grate distance.

Lines 58 through 61 store the measured distance as the new grate distance, turns the "OVERICE/Cup Remove" indicator off, and branches to the cup detection routine. Acquiring a new grate signal allows for minor shifting of the grate during operation.

FIGS. 58 and 59 show the rear and front transducer lenses, respectively, which have been described above. Referring to FIG. 58, the rear lens 540 has a diameter of 0.54 inch and a height of 0.21 inch. FIG. 58A is an edge view, FIG. 58B is a front view, FIG. 58C is a side view, and FIG. 58D is a rear view. The front surface is cylindrical and has a radius of curvature of 2.0 inch. The rear lens is tilted at an angle of 3.5° toward the centerline of the nozzle.

The front lens 542 is shown in FIG. 59 and is also tilted at an angle of 3.5° toward the centerline of the nozzle. FIGS. 59, A, B, C and D are edge, front, side and rear views, respectively. The front surface of the lens 542 has a conical shape formed by a 3.5 degree countersink in the face thereof. Each of the lenses 540 and 542 has a notch 541 and 543, respectively, for orientation purposes.

It is noted that all of the three embodiments of this invention employ a transmitter crystal that is separate from the receiver crystal (hereby defined as a bi-static system).

The difference between a bi-static system and a single crystal transducer used in ultrasonic applications is that the single crystal acts as a transmitter and a receiver. The bi-static system uses a single crystal for a transmitter and a different crystal for a receiver. The characteristics of the two systems are that You can normally get usable signals in the near field range (close to the transducer assembly) from a bi-static system.

The transmitter crystal contines to ring for several cycles after it is turned off, which is merely the "coasting down" of the mechanical motion generated by the current applied to the transducer crystal. The separate receiver crystal in a bi-static system does not experience that jolt from transmitting (unless it is not preperly insulated, electrically and acoustically, from the transmitter). Therefore, it can receive a signal in the near range field much sooner than can a single crystal transducer. Some systems operate at a frequency of around 1 megahertz, which means that they are very limited as to the distance they can transmit an the air because a 1 megahertz ultrasonic signal dissipated very fast through absorption by much smaller particulates in the air than say a 400 kilohertz. Another problem with using 1 megahertz, is that it takes a tremendous amount of power to drive a 1 megahertz ultrasonic signal more than a very few inches.

While the preferred embodiments of this invention have been described above in detail, it is to be understood that variations and modifications can be made therein without departing from the spirit and scope of the present invention as set forth in the appended claims. For example, other materials can be used for the crystals and the lenses and other numbers of crystals can be used and other arrangements and locations can be used for the two crystals of the transducer assembly. In addition, a different ultrasonic transmitter and receiver can be used in place of the crystals, if desired, such as various ultrasonic foil devices. While two specific control circuits have been described in detail, other control circuits and other components thereof can be used. While a microcomputer has been described and is preferred, the control circuit can alternatively use a microprocessor connected to a remote RAM and ROM, for example. While the transducer assembly and the control module are shown attached to the dispenser valve assembly, this is not essential; they can be attached to the dispenser and just connected electrically to the valve assembly.

What is claimed:

1. A transducer assembly for use in the automatic filling of a container with a beverage comprising:
   (a) a housing;
   (b) a front pair of separate transmitter and receiver crystals mounted spaced-apart in said housing, each crystal having a lower surface and having a lens connected to the lower surface of the crystal and with the lower surface of each lens being adjacent the bottom of said housing and being exposed to atmosphere;
   (c) a rear pair of separate transmitter and receiver crystals mounted spaced-apart in said housing, each crystal having a lower surface and having a lens connected to the lower surface of the crystal and with the lower surface of each lens being adjacent the bottom of said housing and being exposed to atmosphere;
   (d) four separate non-ferrous metal tubes being located spaced-apart within said housing in a vertical orientation therein;
   (e) each of said crystals of said front pair of crystals and of said rear pair of crystals being located within but not touching one of said four separate non-ferrous metal tubes; and
   (f) polyurethane foam substantially filling the remaining space within said housing and within each of said tubes and holding each of said tubes and each of said crystals in place therein.

2. The transducer assembly as recited in claim 1 wherein said tubes are identical and parallel to each other.

3. The transducer assembly as recited in claim 1 wherein said housing has four side walls and a bottom wall and an open top and said bottom wall has four circular openings therein and wherein each of said lenses is positioned in a respective one of said openings.

* * * * *